(12) United States Patent
Solan et al.

(10) Patent No.: US 7,741,240 B2
(45) Date of Patent: Jun. 22, 2010

(54) TRANSITION METAL COMPOUNDS FOR OLEFIN POLYMERIZATION AND OLIGOMERIZATION

(75) Inventors: Gregory A. Solan, Leicestershire (GB); Jeremie D. A. Pellettier, St Andrews (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 550 days.

(21) Appl. No.: 11/596,554

(22) PCT Filed: May 23, 2005

(86) PCT No.: PCT/EP2005/005653

§ 371 (c)(1),
(2), (4) Date: Jul. 30, 2007

(87) PCT Pub. No.: WO2005/118605

PCT Pub. Date: Dec. 15, 2005

(65) Prior Publication Data
US 2008/0033125 A1  Feb. 7, 2008

(30) Foreign Application Priority Data
May 26, 2004 (GB) ................................. 0411742.0

(51) Int. Cl.
B01J 31/22 (2006.01)
C08F 4/70 (2006.01)
C07F 15/00 (2006.01)

(52) U.S. Cl. ...................... 502/167; 501/103; 526/134; 526/161; 526/165; 526/169; 526/171; 526/172; 556/32; 556/137; 556/138

(58) Field of Classification Search ............... 556/32, 556/137, 138; 502/103, 167; 526/134, 161, 526/165, 169, 171, 172
See application file for complete search history.

(56) References Cited

U.S. PATENT DOCUMENTS 6,841,693 B1  1/2005  Watanabe et al.

FOREIGN PATENT DOCUMENTS

| CN | 1352202 | 6/2002 |
|---|---|---|
| CN | 1465603 | 1/2004 |
| EP | 1099714 | 5/2001 |
| WO | WO 03/102005 | 12/2003 |

OTHER PUBLICATIONS

Mi, et al, "*Homo- and Copolymerization of Norbornene and Styrene with Pd—and Ni-Based Novel Bridged Dinuclear Diimine Complexes and MAO Macromol.*" Chem. Phys., Wiley-VCH Verlag, Weinheim, XP008049748, 2003, vol. 204, Nr. 5/6, pp. 868-876.

(Continued)

Primary Examiner—Caixia Lu
(74) Attorney, Agent, or Firm—Catherine L. Bell

(57) ABSTRACT

This invention relates to new transition metal catalyst compounds represented by the formula (I):

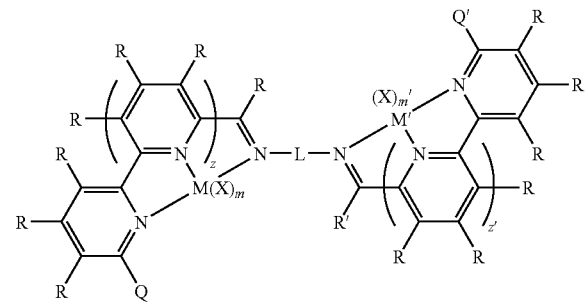

where:
M and M' are, independently, a group 8, 9, 10 or 11 transition metal, preferably Ni, Co, Pd, Cu or Fe;
each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;
R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;
each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;
m and m' are, independently, 0, 1, 2, or 3;
z and z' are, independently, 0, 1, 2, or 3;
N is nitrogen;
Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;
Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and
L is a hydrocarbyl, substituted hydrocarbyl, halocarbyl, substituted halocarbyl, silylcarbyl, substituted silylcarbyl, germylcarbyl, or substituted germylcarbyl substituent.

63 Claims, 3 Drawing Sheets

OTHER PUBLICATIONS

Lopez-Manchado et al., Effect of Interface on the Morphology and Properties of Composites Comprising Poly(propylene) and Short Organic Fibers, Die Angewandte Makromolekulate Chemie, 1999, vol. 265, No. 4595, pp. 20-24.

H. Suzuki, K. Nakarmura and M. Takeshima, *Bull Chem. Soc. Jpn.*, 1971, 44, 2248.

J. H. Oskam, H.H. Fox, K.B. Yap, D. H. McConville, R. O'Dell, B.J. Lichtenstein and R.R. Schrock, *J. Organomet, Chem.*, 1993, 459, 185.

P. Bamfield and P.m. Quan, *Synthesis*, 1978, 537.

C.A. Hunter, *J.Am Chem. Soc.*, 1992, 114, 5303.

J. Uenishi, T. Tanaka, K. Nishiwaki, S. Wakabayashi, S. Oae and H. Tsukube, *J. Org. Chem.*, 1993, 58, 4382.

J. Uenishi, T. Hiraoka, S. Hata, K. Nishiwaki and O. Yonemitxu, *J. Org. Chem.*, 1998, 63, 2481.

Journal of Physical Chemistry, 93(23), 7961-6 CODEN: JPCHAX; ISSN: 0022-3654, 1989.

Journal of Coordination Chemistry, 4(2), 113-23 CODEN: JCCMBQ; ISSN: 0095-8972, 1974.

US 7,741,240 B2

TRANSITION METAL COMPOUNDS FOR OLEFIN POLYMERIZATION AND OLIGOMERIZATION

PRIORITY CLAIM

This application is the national phase entry into the United States Patent Office of international application number PCT/EP2005/005653 filed May 23, 2005, which claims priority to Great Britain Patent Application Number 0411742.0 filed May 26, 2004.

FIELD

This invention relates to new transition metal compounds useful as polymerization and or oligomerization catalysts.

BACKGROUND

As is well known, various processes and catalysts exist for the oligomerization, homopolymerization or copolymerization of olefins.

New polymerization catalysts are of great interest in the industry because they offer many new opportunities for providing new processes and products to the markets in a cheaper and more efficient manner. The following invention relates to new polymerization technology based upon new transition metal catalyst compounds.

Additional references of interest include:
1 H. Suzuki, K. Nakamura and M. Takeshima, *Bull. Chem. Soc. Jpn.*, 1971, 44, 2248.
2 J. H. Oskam, H. H. Fox, K. B. Yap, D. H. McConville, R. O'Dell, B. J. Lichtenstein and R. R. Schrock, *J. Organomet. Chem.*, 1993, 459, 185.
3 P. Bamfield and P. M. Quan, *Synthesis*, 1978, 537.
4 C. A. Hunter, *J. Am. Chem. Soc.*, 1992, 114, 5303.
5 J. Uenishi, T. Tanaka, K. Nishiwaki, S. Wakabayashi, S. Oae and H. Tsukube, *J. Org. Chem.*, 1993, 58, 4382.
6 J. Uenishi, T. Hiraoka, S. Hata, K. Nishiwaki and O. Yonemitsu, *J. Org. Chem.*, 1998, 63, 2481.

SUMMARY OF THE INVENTION

This invention relates to new transition metal catalyst compounds represented by the formula (I):

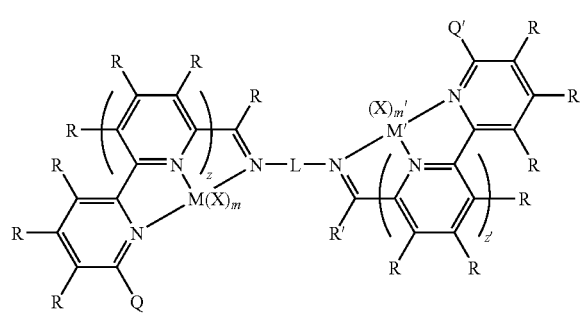

where:

M and M' are, independently, a group 8, 9, 10 or 11 transition metal, preferably Ni, Co or Fe;

each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;

R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;

each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;

m and m' are, independently, 0, 1, 2, or 3;

z and z' are, independently, 0, 1, 2, or 3;

N is nitrogen;

Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and L is a hydrocarbyl, substituted hydrocarbyl, halocarbyl, substituted halocarbyl, silylcarbyl, substituted silylcarbyl, germylcarbyl, or substituted germylcarbyl substituent.

This invention further relates to a catalyst system comprised of the above transition metal compounds combined with an activator and to a process to polymerize unsaturated monomers using such catalyst system.

DEFINITIONS

Figure 1:
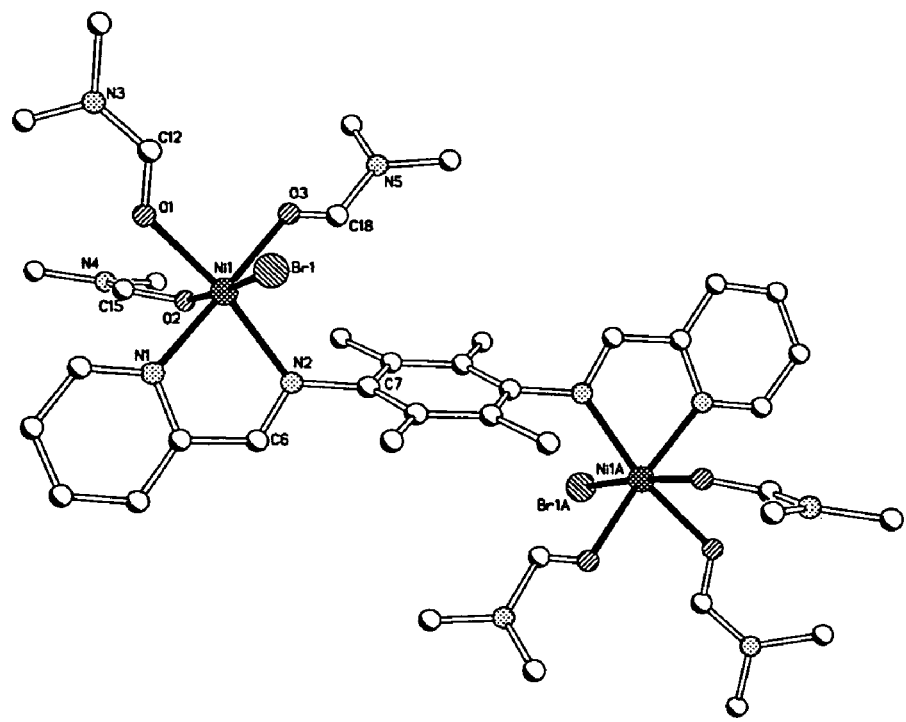
FIG. 1 is a representation of the molecular structure of 27a' (example 38).

As used herein, the numbering scheme for the Periodic Table Groups is the new notation as set out in CHEMICAL AND ENGINEERING NEWS, 63(5), 27 (1985).

As used herein, Me is methyl, t-Bu and $^tBu$ are tertiary butyl, iPr and $^iPr$ are isopropyl, Cy is cyclohexyl, and Ph is phenyl.

The terms "hydrocarbyl radical," "hydrocarbyl" and hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, —B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include NR*$_2$, OR*, SeR*, TeR*, PR*$_2$, AsR*$_2$, SbR*$_2$, SR*, BR*$_2$, SnR*$_3$, PbR*$_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

A "ring carbon atom" is a carbon atom that is part of a cyclic ring structure. By this definition, an indenyl ligand has nine ring carbon atoms.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

In the context of this document, "homopolymerization" would produce a polymer made from one monomer. For example, homopolymerization of propylene would produce homopolypropylene. Homopolymerization of ethylene would produce homopolyethylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst precursor and transition metal compound or complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE INVENTION

In a preferred embodiment, this invention relates to transition metal compounds represented by formula I, where $z=0$ and $z'=0$ as represented by the formulae ($I_0$):

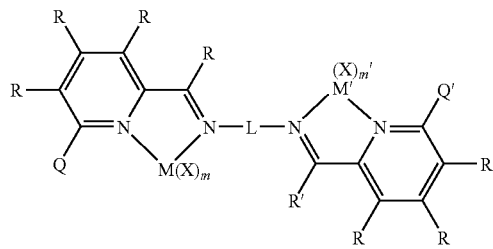

where M, M', X, m, m', R, R', Q, Q', N, and L are as defined above.

In a preferred embodiment, this invention relates to transition metal compounds represented by formula I, where $z=0$ and $z'=1$ as represented by the formulae ($I_1$):

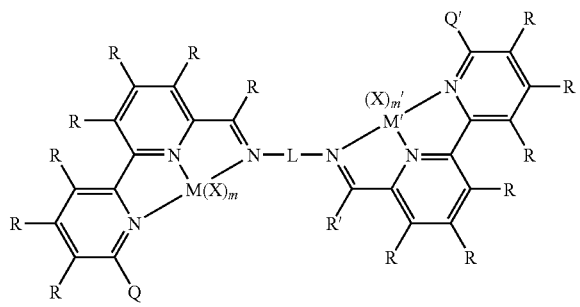

where M, M', X, m, m', R, R', Q, Q', N, and L are as defined above.

In a preferred embodiment, this invention relates to transition metal compounds represented by formula I, where $z=2$ and $z'=2$ as represented by the formulae ($I_2$):

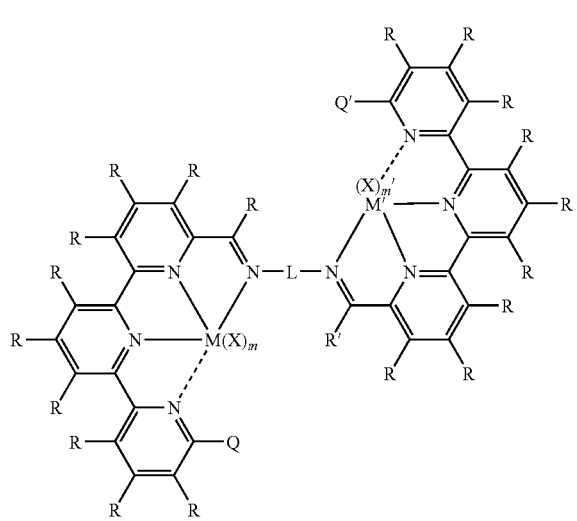

where M, M', X, m, m', R, R'Q, Q', N, and L are as defined above.

In a preferred embodiment, this invention relates to transition metal compounds represented by formula I, where $z=3$ and $z'=3$ as represented by the formulae ($I_3$):

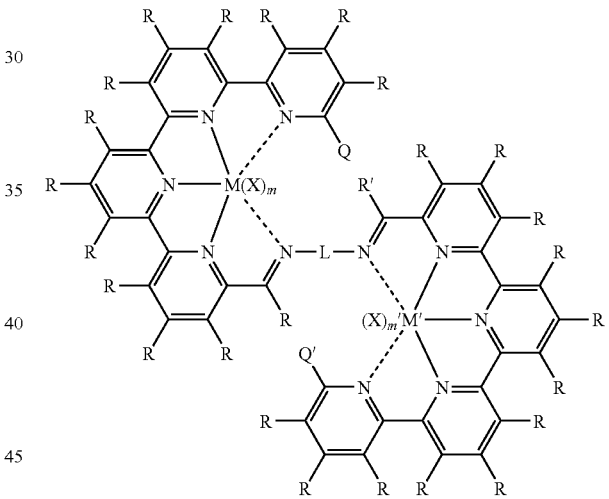

where M, M', X, m, m', R, R', Q, Q', N, and L are as defined above.

In another embodiment, z and z' are different. For example, z may be zero and z' may be one as represented by formulae

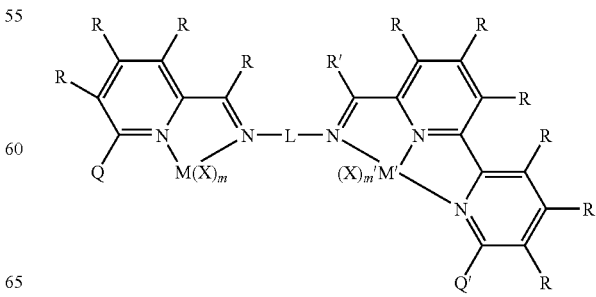

where M, M', X, m, m', R, R', Q, Q', N, and L are as defined above. II:

In a preferred embodiment, z=0 and z'=1, 2, or 3. In a preferred embodiment, z=1 and z'=1, 2, or 3. In a preferred embodiment, z=2 and z'=1, 2, or 3. In a preferred embodiment, z=3 and z'=1, 2, or 3. In a preferred embodiment, z'=0 and z=1, 2, or 3. In a preferred embodiment, z'=1 and z=1, 2, or 3. In a preferred embodiment, z'=2 and z=1, 2, or 3. In a preferred embodiment, z'=3 and z=1, 2, or 3.

In a preferred embodiment this invention relates to transition metal compounds represented by formulae I, $I_0$, $I_1$, $I_2$, $I_3$, and II above where:

1) each R group is, independently, selected from the group consisting of C1 to C20 hydrocarbyls, C1 to C20 substituted phenyls, and all isomers thereof, preferably ethyl, methyl, propyl, butyl, pentyl, hexyl, septyl, octyl, nonyl, decyl, undecyl, dodecyl, phenyl, methylphenyl; and/or 2) each R' group is, independently, selected from the group consisting of C1 to C20 hydrocarbyls, C1 to C20 substituted phenyls, and all isomers thereof, preferably ethyl, methyl, propyl, butyl, pentyl, hexyl, septyl, octyl, nonyl, decyl, undecyl, dodecyl, phenyl, methylphenyl; and/or 2) each Q and Q' is, independently, selected from the group consisting of C1 to C20 hydrocarbyls, C1 to C20 substituted phenyls, and all isomers thereof, preferably ethyl, methyl, propyl, butyl, pentyl, hexyl, septyl, octyl, nonyl, decyl, undecyl, dodecyl, phenyl, methylphenyl; and/or 3) each X is, independently, selected from the group consisting of chlorine, bromine, fluorine, methyl, ethyl, propyl, isopropyl, butyl, t-butyl, pentyl, hexyl, phenyl, and methylphenyl; and/or 4) M is Fe, Co, Pd, Cu or Ni, preferably Fe, Co or Ni; and/or 5) M' is Fe, Co, Pd, Cu or Ni, preferably Fe, Co or Ni; and/or 6) L is a substituted or unsubstituted aryl group.

In one embodiment, the substituted or unsubstituted aryl group (L) is selected from the group consisting of:

1) a monoaryl unit unsubstituted, partially substituted or fully substituted with a number of R substituents on various positions on the ring, where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (3):

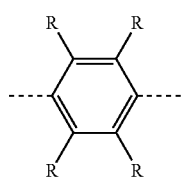

(3)

where the dashed lines indicate the bonds to the nitrogen atoms in formulae I, $I_0$, $I_1$, $I_2$, $I_3$, and II above;

2) a fused aryl unit selected from the group consisting of the C10 to C22 fused aromatic hydrocarbyl units, unsubstituted, partially substituted or fully substituted with a number of R substituents on various positions of the ring, where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (4):

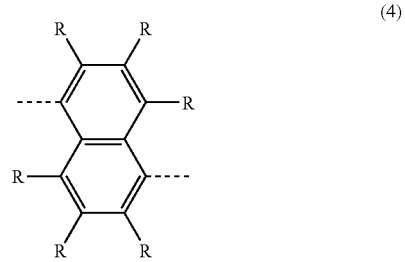

(4)

where the dashed lines indicate the bonds to the nitrogen atoms in formulae I, $I_0$, $I_1$, $I_2$, $I_3$, and II above;

3) two aryl units bridged by a substituted or unsubstituted alkyl group, selected from the group consisting of C1 to C30 hydrocarbyls, and all isomers thereof, preferably ethyl, methyl, propyl, butyl, pentyl, hexyl, septyl, octyl, nonyl, decyl, undecyl, dodecyl, and further where a number of R substituents are on various positions of the aryl rings or on the alkyl bridge, where each R group is, independently, selected from the group consisting of hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (5):

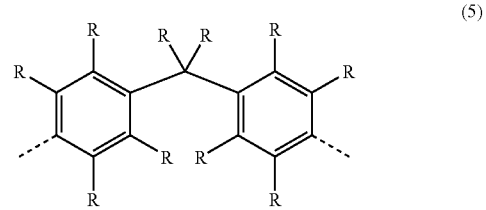

(5)

where the dashed lines indicate the bonds to the nitrogen atoms in formulae I, $I_0$, $I_1$, $I_2$, $I_3$, and II above;

4) two aryl units bridged by an unsaturated hydrocarbon group (which may be substituted or unsubstituted), selected from the group consisting of C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, further where a number of R substituents are on various positions of the aryl rings or on the hydrocarbon bridge, where each R group is, independently, selected from the group consisting of hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (6):

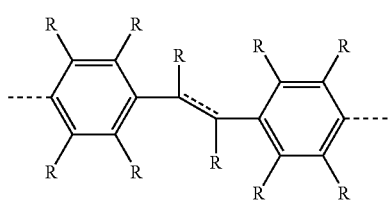
(6)

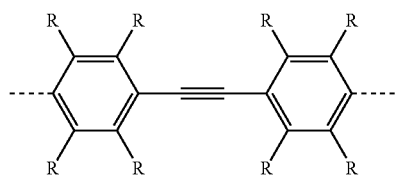

where the dashed lines indicate the bonds to the nitrogen atoms in formulae I, $I_0$, $I_1$, $I_2$, $I_3$, and II above;

5) two aryl rings bridged by a fused aryl unit selected from the fused aryl units having ten or more carbon atoms, unsubstituted, partially substituted or fully substituted with a number of R substituents on various positions of the rings, where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (7):

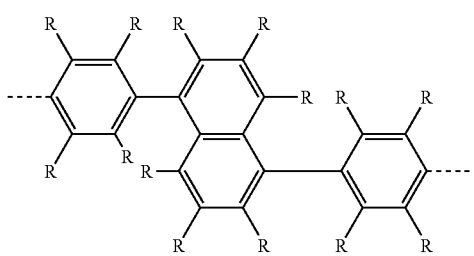
(7)

where the dashed lines indicate the bonds to the nitrogen atoms in formulae I, $I_0$, $I_1$, $I_2$, $I_3$, and II above;

6) two aryl rings bridged by a polyaryl unit in which the polyaryl unit is selected from the group consisting of one or more aromatic rings, unsubstituted, partially substituted or fully substituted with a number of R substituents on various positions of the rings, where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (8):

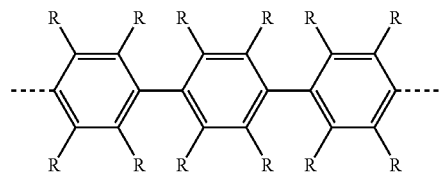
(8)

where the dashed lines indicate the bonds to the nitrogen atoms in formulae I, $I_0$, $I_1$, $I_2$, $I_3$, and II above;

7) two aryl rings bridged by a methylene unit in which the methylene unit contains one or two R groups selected from hydrogen, halogen, C1 to C30 hydrocarbyls, C1 to C30 substituted phenyls, and all isomers thereof, (preferably ethyl, methyl, propyl, butyl, pentyl, hexyl, septyl, octyl, nonyl, decyl, undecyl, dodecyl, phenyl, methylphenyl), preferably substituted phenyl with one or more functionalized groups selected from the group consisting of halide, carbonyl, nitro, hydroxyl, amine, thiolate, carboxylic acid, ester, ether, where the R groups on the bridged aryl groups can be selected from a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, substituted phenyl, a preferred example includes aryl groups represented by the formula (9):

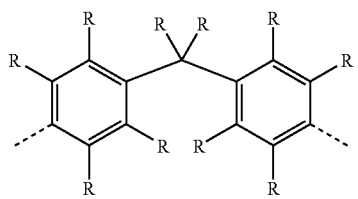
(9)

where the dashed lines indicate the bonds to the nitrogen atoms in formulae I, $I_0$, $I_1$, $I_2$, $I_3$, and II above;

8) two diaryl units bridged by a heteroatom X (X=O, NR, PR, S, BR, AlR, $SiR_2$) in which a number of R substituents may be on various positions on the heteroatom, where each R group is, independently, selected from the group consisting of hydrogen, a halogen, or C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (10):

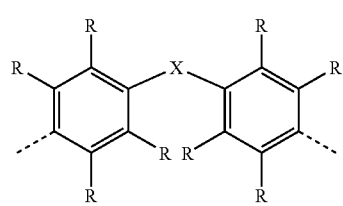
(10)

where the dashed lines indicate the bonds to the nitrogen atoms in formulae I, $I_0$, $I_1$, $I_2$, $I_3$, and II above;

9) two aryl units bridged by a heteroatom or hetroatom-containing fragment X (X=O, NR, PR, S, BR, AlR, SiR$_2$) and one or more hydrocarbon sections, selected from the group consisting of C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, where a number of R substituents are on various positions of the aryl rings, the hydrocarbon bridge or the hetereoatom, and where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (11):

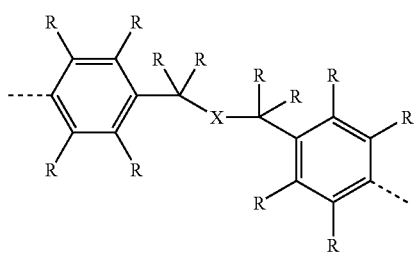

where the dashed lines indicate the bonds to the nitrogen atoms in formulae I, I$_0$, I$_1$, I$_2$, I$_3$, and II above;

10) two aryl units bridged by one or more 5-, 6- or 7-membered heterocyclic rings containing one or more heteroatoms X (X=O, NR, BR), where the internal rings can be unsubstituted, partially substituted or fully substituted and saturated, partially unsaturated or aromatic, and where a number of R substituents are on various position of the aryl rings, the hydrocarbon bridge or the hetereoatom, and where each R group is, independently, selected from the group consisting of a hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (12):

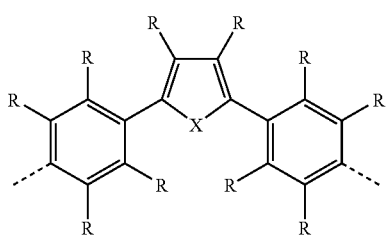

where the dashed lines indicate the bonds to the nitrogen atoms in formulae I, I$_0$, I$_1$, I$_2$, I$_3$, and II above;

11) two aryl units bridged by a metallocene (comprising two cyclopentadienyl groups and a metal (M) from Group 4 to Group 9 of the Periodic Table, preferably Fe) section in which the aromatic rings can be unsubstituted, partially substituted or fully substituted with a number of R substituents on various position of the aryl or the cyclopentadienyl and where each R group is, independently, selected from the group consisting of hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (13):

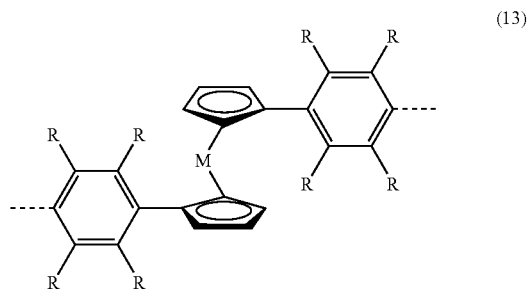

where the dashed lines indicate the bonds to the nitrogen atoms in formulae I, I$_0$, I$_1$, I$_2$, I$_3$, and II above; and 12) two aryl units bridged by an α-diimine, a iminopyridine, a bis(imino)pyridine or a polypyridine group coordinated to a metal dihalide where the metal (M) is selected from Group 8 to Group 11 of the Periodic Table, where the imino carbons or the pyridine rings can be unsubstituted, partially substituted or fully substituted with a number of R substituents on various positions of the aryl, where each R group is, independently, selected from the group consisting of hydrogen, a halogen, C1 to C30 hydrocarbyls, C1 to C30 substituted phenyls, and all isomers thereof, preferably ethyl, methyl, propyl, butyl, pentyl, hexyl, septyl, octyl, nonyl, decyl, undecyl, dodecyl, phenyl, methylphenyl, a preferred example includes aryl groups represented by the formula (14):

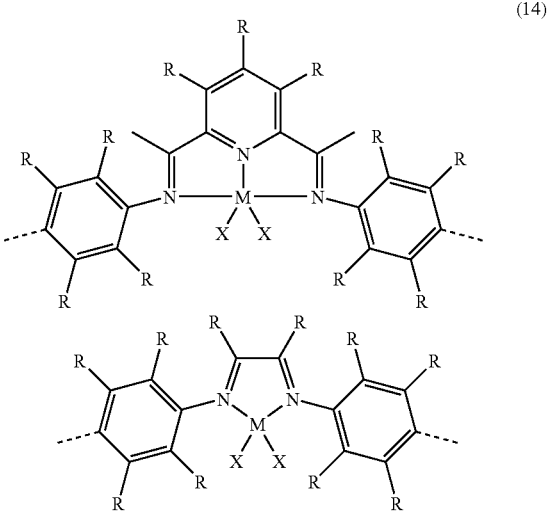

where the dashed lines indicate the bonds to the nitrogen atoms in formulae I, I$_0$, I$_1$, I$_2$, I$_3$, and II above.

In another embodiment, z and z' are the same. In another embodiment, m and m' are the same. In another embodiment, M and M' are the same. In another embodiment, Q and Q' are the same. In another embodiment, z and z' are the same; m and m' are the same; M and M' are the same; and Q and Q' are the same. In another embodiment, z and z' are the same; and/or m and m' are the same; and/or M and M' are the same; and/or Q and Q' are the same.

In another embodiment, z and z' are different. In another embodiment, m and m' are different. In another embodiment, M and M' are different. In another embodiment, Q and Q' are different. In another embodiment, z and z' are different; m and n' are different; M and M' are different; and Q and Q' are different. In another embodiment, z and z' different; and/or m and m' different; and/or M and M' are different; and/or Q and Q' different.

In a preferred embodiment, each R is independently selected from the group consisting of methyl, ethyl, propyl, isopropyl, butyl, pentyl, hexyl, septyl, octyl, nonyl, decyl, undecyl, phenyl, and methylphenyl.

In a preferred embodiment, R' is selected from the group consisting of methyl, ethyl, propyl, isopropyl, butyl, pentyl, hexyl, septyl, octyl, nonyl, decyl, undecyl, phenyl, and methylphenyl.

In a preferred embodiment, each Q and Q' is independently selected from the group consisting of methyl, ethyl, propyl, isopropyl, butyl, pentyl, hexyl, septyl, octyl, nonyl, decyl, undecyl, phenyl, and methylphenyl.

In a preferred embodiment, each X and X' is independently selected from the group consisting of chlorine, bromine, sluorine, iodine, methyl, ethyl porpyl, isopropyl, butyl, t-butyl, pentyl, hexyl, and phenyl.

In a preferred embodiment, M and M' is independently is selected from the group consisting of iron, cobalt, nickel, palladium, and copper.

In a preferred embodiment, R, R', Q, Q', X, X', M, M' and L are each independently selected from Table 1 below.

TABLE 1

| R, R', Q and Q' | X | M | L |
|---|---|---|---|
| ethyl | chlorine | Iron | phenyl |
| methyl | bromine | Cobalt | 2,5-dimethylphenyl |
| propyl | fluorine | Nickel | 2,3,5,6-tetramethylphenyl |
| isopropyl | iodine | Palladium | naphtalenyl |
| butyl | methyl | Copper | anthracenyl |
| pentyl | ethyll | | phenantracenyl |
| hexyl | propyl | | chrysenelyl |
| septyl | isopropyl | | triphenylenyl |
| octyl | butyl | | diphenylmethylenyl |
| nonyl | t-butyl | | Di-(3-methylphenyl)-methan |
| decyl | pentyl | | Di-(3,5-dimethylphenyl)-methan |
| undecyl | hexyl | | Di-(3,5-diisopropylylphenyl)-methan |
| phenyl | phenyl | | (3-methylphenyl)(3,5-diisopropylylphenyl)-methan |
| methylephenyl | | | (3,5-dimethylphenyl)(3,5-diisopropylylphenyl)-methan |
| | | | 1,1'-(1,2-ethanediyl)bis-benzene |
| | | | 3,5,3',5'-tetramethyl-1,1'-(1,2-ethanediyl)bis-benzene |
| | | | 3,5,3',5'-tetraisopropyl-1,1'-(1,2-ethanediyl)bis-benzene |
| | | | 1,1'-(1,3-propanediyl)bis-benzene |
| | | | 3,5,3',5'-tetramethyl-1,1'-(1,2-ethanediyl)bis-benzene |
| | | | 3,5,3',5'-tetraisopropyl-1,1'-(1,3-propanediyl)bis-benzene |
| | | | 1,1'-(1,2-ethenediyl)bis-benzene |
| | | | 3,5,3',5'-tetramethyl-(1,2-ethenediyl)bis-benzene |
| | | | 3,5,3',5'-tetraisopropyl-(1,2-ethenediyl)bis-benzene |
| | | | 1,1'-(1,2-ethynediyl)bis-benzene |
| | | | 3,5,3',5'-tetramethyl-1,1'-(1,2-ethynediyl)bis-benzene |
| | | | 3,5,3',5'-tetraisopropyl-1,1'-(1,2-ethynediyl)bis-benzene |
| | | | 1,6-diphenyl-naphthalene |
| | | | 1,6-di-(3,5-dimethylphenyl)-naphthalene |
| | | | 1,6-di-(3,5-diisopropylphenyl)-naphthalene |
| | | | 3,6-diphenyl-phenanthrene |
| | | | 3,6-di-(3,5-dimethylphenyl)-phenanthrene |
| | | | 3,6-di-(3,5-diisopropyl)-phenanthrene |
| | | | 1,1'-biphenyl |
| | | | 3,5,3',5'-tetramethyl-1,1'-biphenyl |
| | | | 3,5,3',5'-tetraisopropyl-1,1'-biphenyl |
| | | | [1,1';4',1"]terphenyl |
| | | | 2,3,5",6"-tetramethyl-[1,1';4',1"]terphenyl |
| | | | 2,3,5",6"-tetraisopropyl-[1,1';4',1"]terphenyl |
| | | | 2,3,5,6,2',3',5',6',2",3",5",6"-dodecamethyl-[1,1';4',1"]terphenyl |
| | | | [1,4';1',1";4",1'"]quaterphenyl |
| | | | 2,3,5'",6'"-tetradecamethyl-[1,4';1',1";4",1'"]quaterphenyl |
| | | | 2,3,5'",6'"-tetraisopropyl- |

TABLE 1-continued

| R, R', Q and Q' | X | M | L |
|---|---|---|---|
| | | | [1,4';1'',1'';4'',1''']quaterphenyl 2,3,5,6,2',3',5',6',2'',3'',5'',6'',2''',3''',5''',6'''-hexadecamethyl-[1,4';1'',1'';4'',1''']quaterphenyl 3,5,3'''',5''''-tetra-tert-butyl-[1,1';4',1'';4'',1''';4''',1'''']quinquephenyl (4-fluoro-phenyl)-diphenyl-methane (4-fluoro-phenyl)-di-(3,5-dimethylphenyl)-methane (4-fluoro-phenyl)-di-(3,5-diisopropylphenyl)-methane (4-chloro-phenyl)-diphenyl-methane (4-chloro-phenyl)-di-(3,5-dimethylphenyl)-methane (4-chloro-phenyl)-di-(3,5-diisopropylphenyl)-methane (4-bromo-phenyl)-diphenyl-methane (4-bromo-phenyl)-di-(3,5-dimethylphenyl)-methane (4-bromo-phenyl)-di-(3,5-diisopropylphenyl)-methane 4-[diphenyl-methyl]-benzaldehyde 4-[bis-(3,5-dimethyl-phenyl)-methyl]-benzaldehyde 4-[bis-(3,5-diisopropyl-phenyl)-methyl]-benzaldehyde 4-[diphenyl-methyl]-phenol 4-[bis-(3,5-dimethyl-phenyl)-methyl]-phenol 4-[bis-(3,5-diisopropyl-phenyl)-methyl]-phenol 4-[diphenyl-methyl]-thiophenol 4-[bis-(3,5-dimethyl-phenyl)-methyl]-thiophenol 4-[bis-(3,5-diisopropyl-phenyl)-methyl]-thiophenol 4-[diphenyl-methyl]-benzoic acid 4-[bis-(3,5-dimethyl-phenyl)-methyl]-benzoic acid 4-[bis-(3,5-diisopropyl-phenyl)-methyl]-benzoic acid 4-[diphenyl-methyl]-nitro-benzene 4-[bis-(3,5-dimethyl-phenyl)-methyl]-nitro-benzene 4-[bis-(3,5-diisopropyl-phenyl)-methyl]-nitro-benzene 4-[diphenyl-methyl]-benzenamine 4-[bis-(3,5-dimethyl-phenyl)-methyl]-benzenamine 4-[bis-(3,5-diisopropyl-phenyl)-methyl]-benzenamine diphenyl-ether bis-(3,5-dimethyl-phenyl)-ether bis-(3,5-diisopropyl-phenyl)-ether diphenyl-amine bis-(3,5-dimethyl-phenyl)-amine bis-(3,5-diisopropyl-phenyl)-amine diphenyl-phosphine bis-(3,5-dimethyl-phenyl)-phosphine bis-(3,5-diisopropyl-phenyl)-phosphine diphenyl sulfide bis-(3,5-dimethyl-phenyl)-sulfide bis-(3,5-diisopropyl-phenyl)-sulfide methyl-diphenyl-borane methyl-bis-(3,5-dimethyl-phenyl)-borane methyl-bis-(3,5-diisopropyl-phenyl)-borane methyl-diphenyl-aluminium methyl-bis-(3,5-dimethyl-phenyl)-aluminium methyl-bis-(3,5-diisopropyl-phenyl)-aluminium dimethyl-diphenyl-silane dimethyl-bis-(3,5-dimethyl-phenyl)-silane dimethyl-bis-(3,5-diisopropyl-phenyl)-silane |

TABLE 1-continued

| R, R', Q and Q' | X | M | L |
|---|---|---|---|
| | | | 2,5-diphenyl-pyrrole |
| | | | 2,5-bis-(3,5-dimethyl-phenyl)-pyrrole |
| | | | 2,5-bis-(3,5-diisopropyl-phenyl)-pyrrole |
| | | | 2,5-diphenyl-furan |
| | | | 2,5-bis-(3,5-dimethyl-phenyl)-furan |
| | | | 2,5-bis-(3,5-diisopropyl-phenyl)-furan |
| | | | 2,6-diphenyl-pyridine |
| | | | 2,6-bis-(3,5-dimethyl-phenyl)-pyridine |
| | | | 2,6-bis-(3,5-diisopropyl-phenyl)-pyridine |
| | | | diphenylferrocene |
| | | | Bis-(imino)-pyridin-iron-dichloride |
| | | | Bis-(imino)-pyridin-iron-dibromide |
| | | | [2,2';6',2"]terpyridine-iron-dichloride |
| | | | [2,2';6',2"]terpyridine-iron-dibromide |
| | | | Bis-(imino)-pyridin-cobalt-dichloride |
| | | | Bis-(imino)-pyridin-cobalt-dibromide |
| | | | [2,2';6',2"]terpyridine-cobalt-dichloride |
| | | | [2,2';6',2"]terpyridine-cobalt-dibromide |
| | | | ethane-1,2-diylidenediamine-nickel-dichloride |
| | | | ethane-1,2-diylidenediamine-nickel-dibromide |
| | | | ethane-1,2-diylidenediamine-palladium-dichloride |
| | | | ethane-1,2-diylidenediamine-palladium-dibromide |
| | | | ethane-1,2-diylidenediamine-copper-dichloride |
| | | | ethane-1,2-diylidenediamine-copper-dibromide |
| | | | ethane-1,2-dimethyl-1,2-diylidenediamine-nickel-dichloride |
| | | | ethane-1,2-dimethyl-1,2-diylidenediamine-nickel-dibromide |
| | | | ethane-1,2-dimethyl-1,2-diylidenediamine-palladium-dichloride |
| | | | ethane-1,2-dimethyl-1,2-diylidenediamine-palladium-dibromide |
| | | | ethane-1,2-dimethyl-1,2-diylidenediamine-copper-dichloride |
| | | | ethane-1,2-dimethyl-1,2-diylidenediamine-copper-dibromide |

A set of exemplary transition metal catalyst compounds is set out below. These are by way of example only and are not intended to list every compound that is within the scope of the invention. Preferred transition metal catalyst compounds include:

[N,N-bis-(pyridin-2-ylmethylene)-benzene-1,4-diamine]dinickel tetrabromide,

[N,N-bis-(pyridin-2-ylethylidene)-benzene-1,4-diamine]dinickel tetrabromide,

[N-(pyridin-2-ylethylidene)-N-(pyridin-2-ylmethylene)-benzene-1,4-diamine]dinickel tetrabromide,

[N,N-bis-(pyridin-2-ylmethylene)-benzene-1,4-diamine]dinickel tetrachloride,

[N,N-bis-(pyridin-2-ylethylidene)-benzene-1,4-diamine]dinickel tetrachloride,

[N-(pyridin-2-ylethylidene)-N-(pyridin-2-ylmethylene)-benzene-1,4-diamine]dinickel tetrachloride,

[N,N-bis-(pyridin-2-ylmethylene)-benzene-1,4-diamine]dinickel tetramethyl,

[N,N-bis-(pyridin-2-ylethylidene)-benzene-1,4-diamine]dinickel tetramethyl,

[N-(pyridin-2-ylethylidene)-N-pyridin-2-ylmethylene)-benzene-1,4-diamine]dinickel tetramethyl,

[2,5-dimethyl-N,N-bis-(pyridin-2-ylmethylene)-benzene-1,4-diamine]dinickel tetrabromide,

[2,5-dimethyl-N,N-bis-(pyridin-2-ylethylidene)-benzene-1,4-diamine]dinickel tetrabromide,

[2,5-dimethyl-N-(pyridin-2-ylethylidene)-N-(pyridin-2-ylmethylene)-benzene-1,4-diamine]dinickel tetrabromide,

[2,5-dimethyl-N,N-bis-(pyridin-2-ylmethylene)-benzene-1,4-diamine]dinickel tetrachloride,

[2,5-dimethyl-N,N-bis-(pyridin-2-ylethylidene)-benzene-1,4-diamine]dinickel tetrachloride,

[2,5-dimethyl-N-(pyridin-2-ylethylidene)-N-(pyridin-2-ylmethylene)-benzene-1,4-diamine]dinickel tetrachloride,

[2,5-dimethyl-N,N-bis-(pyridin-2-ylmethylene)-benzene-1,4-diamine]dinickel tetramethyl,

[2,5-dimethyl-N,N-bis-(pyridin-2-ylethylidene)-benzene-1,4-diamine]dinickel tetramethyl,

[2,5-dimethyl-N-(pyridin-2-yethylidene)-N-(pyridin-2-ylmethylene)-benzene-1,4-diamine]dinickel tetramethyl,

[2,3,5,6-tetramethyl-N,N-bis-(pyridin-2-ylmethylene)-benzene-1,4-diamine]dinickel tetrabromide,

[2,3,5,6-tetramethyl-N,N-bis-(pyridin-2-ylethylidene)-benzene-1,4-diamine]dinickel tetrabromide,

[2,3,5,6-tetramethyl-N-(pyridin-2-ylethylidene)-N-(pyridin-2-ylmethylene)-benzene-1,4-diamine]dinickel tetrabromide,

[2,3,5,6-tetramethyl-N,N-bis-(pyridin-2-ylmethylene)-benzene-1,4-diamine]dinickel tetrachloride,

[2,3,5,6-tetramethyl-N,N-bis-(pyridin-2-ylethylidene)-benzene-1,4-diamine]dinickel tetrachloride,
[2,3,5,6-tetramethyl-N-(pyridin-2-ylethylidene)-N-(pyridin-2-ylmethylene)-benzene-1,4-diamine]dinickel tetrachloride,
[2,3,5,6-tetramethyl-N,N-bis-(pyridin-2-ylmethylene)-benzene-1,4-diamine]dinickel tetramethyl,
[2,3,5,6-tetramethyl-N,N-bis-(pyridin-2-ylethylidene)-benzene-1,4-diamine]dinickel tetramethyl,
[2,3,5,6-tetramethyl-N-(pyridin-2-ylethylidene)-N-(pyridin-2-ylmethylene)-benzene-1,4-diamine]dinickel tetramethyl,
[N,N-bis-(pyridin-2-ylmethylene)-benzene-1,4-diamine]dipalladium tetrabromide,
[N,N-bis-(pyridin-2-ylethylidene)-benzene-1,4-diamine]dipalladium tetrabromide,
[N-(pyridin-2-ylethylidene)-N-(pyridin-2-ylmethylene)-benzene-1,4-diamine]dipalladium tetrabromide,
[N,N-bis-pyridin-2-ylmethylene)-benzene-1,4-diamine]dipalladium tetrachloride,
[N,N-bis-(pyridin-2-ylethylidene)-benzene-1,4-diamine]dipalladium tetrachloride,
[N-(pyridin-2-ylethylidene)-N-(pyridin-2-ylmethylene)-benzene-1,4-diamine]dipalladium tetrachloride,
[N,N-bis-(pyridin-2-ylmethylene)-benzene-1,4-diamine]dipalladium tetramethyl
[N,N-bis-(pyridin-2-ylethylidene)-benzene-1,4-diamine]dipalladium tetramethyl
[N-(pyridin-2-ylethylidene)-N-(pyridin-2-ylmethylene)-benzene-1,4-diamine]dipalladium tetramethyl
[2,5-dimethyl-N,N-bis-(pyridin-2-ylmethylene)-benzene-1,4-diamine]dipalladium tetrabromide,
[2,5-dimethyl-N,N-bis-(pyridin-2-ylethylidene)-benzene-1,4-diamine]dipalladium tetrabromide,
[2,5-dimethyl-N-(pyridin-2-ylethylidene)-N-(pyridin-2-ylmethylene)-benzene-1,4-diamine]dipalladium tetrabromide,
[2,5-dimethyl-N,N-bis-(pyridin-2-ylmethylene)-benzene-1,4-diamine]dipalladium tetrachloride,
[2,5-dimethyl-N,N-bis-(pyridin-2-ylethylidene)-benzene-1,4-diamine]dipalladium tetrachloride,
[2,5-dimethyl-N-(pyridin-2-ylethylidene)-N-(pyridin-2-ylmethylene)-benzene-1,4-diamine]dipalladium tetrachloride,
[2,5-dimethyl-N,N-bis-(pyridin-2-ylmethylene)-benzene-1,4-diamine]dipalladium tetramethyl,
[2,5-dimethyl-N,N-bis-pyridin-2-ylethylidene)-benzene-1,4-diamine]dipalladium tetramethyl,
[2,5-dimethyl-N-(pyridin-2-ylethylidene)-N-(pyridin-2-ylmethylene)-benzene-1,4-diamine]dipalladium tetramethyl
[2,3,5,6-tetramethyl-N,N-bis-(pyridin-2-ylmethylene)-benzene-1,4-diamine]dipalladium tetrabromide,
[2,3,5,6-tetramethyl-N,N-bis-(pyridin-2-ylethylidene)-benzene-1,4-diamine]dipalladium tetrabromide,
[2,3,5,6-tetramethyl-N-(pyridin-2-ylethylidene)-N-(pyridin-2-ylmethylene)-benzene-1,4-diamine]dipalladium tetrabromide,
[2,3,5,6-tetramethyl-N,N-bis-(pyridin-2-ylmethylene)-benzene-1,4-diamine]dipalladium tetrachloride,
[2,3,5,6-tetramethyl-N,N-bis-(pyridin-2-ylethylidene)-benzene-1,4-diamine]dipalladium tetrachloride,
[2,3,5,6-tetramethyl-N-(pyridin-2-ylethylidene)-N-(pyridin-2-ylmethylene)-benzene-1,4-diamine]dipalladium tetrachloride,
[2,3,5,6-tetramethyl-N,N-bis-(pyridin-2-ylmethylene)-benzene-1,4-diamine]dipalladium tetramethyl,
[2,3,5,6-tetramethyl-N,N-bis-(pyridin-2-ylethylidene)-benzene-1,4-diamine]dipalladium tetramethyl,
[2,3,5,6-tetramethyl-N-(pyridin-2-ylethylidene)-N-(pyridin-2-ylmethylene)-benzene-1,4-diamine]dipalladium tetramethyl,
[N,N-bis-(pyridin-2-ylmethylene)-benzene-1,4-diamine]dicopper tetrabromide,
[N,N-bis-(pyridin-2-ylethylidene)-benzene-1,4-diamine]dicopper tetrabromide,
[N-(pyridin-2-ylethylidene)-N-(pyridin-2-ylmethylene)-benzene-1,4-diamine]dicopper tetrabromide,
[N,N-bis-(pyridin-2-ylmethylene)-benzene-1,4-diamine]dicopper tetrachloride,
[N,N-bis-(pyridin-2-ylethylidene)-benzene-1,4-diamine]dicopper tetrachloride,
[N-(pyridin-2-ylethylidene)-N-(pyridin-2-ylmethylene)-benzene-1,4-diamine]dicopper tetrachloride,
[N,N-bis-(pyridin-2-ylmethylene)-benzene-1,4-diamine]dicopper tetramethyl,
[N,N-bis-(pyridin-2-ylethylidene)-benzene-1,4-diamine]dicopper tetramethyl,
[N-(pyridin-2-ylethylidene)-N-(pyridin-2-ylmethylene)-benzene-1,4-diamine]dicopper tetramethyl,
[2,5-dimethyl-N,N-bis-(pyridin-2-ylmethylene)-benzene-1,4-diamine]dicopper tetrabromide,
[2,5-dimethyl-N,N-bis-(pyridin-2-ylethylidene)-benzene-1,4-diamine]dicopper tetrabromide,
[2,5-dimethyl-N-(pyridin-2-ylethylidene)-N-(pyridin-2-ylmethylene)-benzene-1,4-diamine]dicopper tetrabromide,
[2,5-dimethyl-N,N-bis-(pyridin-2-ylmethylene)-benzene-1,4-diamine]dicopper tetrachloride,
[2,5-dimethyl-N,N-bis-(pyridin-2-ylethylidene)-benzene-1,4-diamine]dicopper tetrachloride,
[2,5-dimethyl-N-(pyridin-2-ylethylidene)-N-(pyridin-2-ylmethylene)-benzene-1,4-diamine]dicopper tetrachloride,
[2,5-dimethyl-N,N-bis-(pyridin-2-ylmethylene)-benzene-1,4-diamine]dicopper tetramethyl,
[2,5-dimethyl-N,N-bis-(pyridin-2-ylethylidene)-benzene-1,4-diamine]dicopper tetramethyl,
[2,5-dimethyl-N-(pyridin-2-ylethylidene)-N-(pyridin-2-ylmethylene)-benzene-1,4-diamine]dicopper tetramethyl,
[2,3,5,6-tetramethyl-N,N-bis-(pyridin-2-ylmethylene)-benzene-1,4-diamine]dicopper tetrabromide,
[2,3,5,6-tetramethyl-N,N-bis-(pyridin-2-ylethylidene)-benzene-1,4-diamine]dicopper tetrabromide,
[2,3,5,6-tetramethyl-N-(pyridin-2-ylethylidene)-N-(pyridin-2-ylmethylene)-benzene-1,4-diamine]dicopper tetrabromide,
[2,3,5,6-tetramethyl-N,N-bis-(pyridin-2-ylmethylene)-benzene-1,4-diamine]dicopper tetrachloride,
[2,3,5,6-tetramethyl-N,N-bis-(pyridin-2-ylethylidene)-benzene-1,4-diamine]dicopper tetrachloride,
[2,3,5,6-tetramethyl-N-(pyridin-2-ylethylidene)-N-(pyridin-2-ylmethylene)-benzene-1,4-diamine]dicopper tetrachloride,
[2,3,5,6-tetramethyl-N,N-bis-(pyridin-2-ylmethylene)-benzene-1,4-diamine]dicopper tetramethyl,
[2,3,5,6-tetramethyl-N,N-bis-(pyridin-2-ylethylidene)-benzene-1,4-diamine]dicopper tetramethyl,
[2,3,5,6-tetramethyl-N-(pyridin-2-ylethylidene)-N-(pyridin-2-ylmethylene)-benzene-1,4-diamine]dicopper tetramethyl,
[N,N-bis-{(6-pyridin-2-yl)pyridin-2-ylmethylene}-benzene-1,4-diamine]diiron tetrabromide,
[N,N-bis-{(6-pyridin-2-yl)pyridin-2-ylethylidene}-benzene-1,4-diamine]diiron tetrabromide,

[N,N-bis-{(6-pyridin-2-yl)pyridin-2-ylmethylene}-benzene-1,4-diamine]diiron tetrachloride,
[N,N-bis-{(6-pyridin-2-yl)pyridin-2-ylethylidene}-benzene-1,4-diamine]diiron tetrachloride,
[N,N-bis-{(6-pyridin-2-yl)pyridin-2-ylmethylene}-benzene-1,4-diamine]diiron tetramethyl
[N,N-bis-{(6-pyridin-2-yl)pyridin-2-ylethylidene}-benzene-1,4-diamine]diiron tetramethyl,
[2,5-dimethyl-N,N-bis-{(6-pyridin-2-yl)pyridin-2-ylmethylene}-benzene-1,4-diamine]diiron tetrabromide,
[2,5-dimethyl-N,N-bis-{(6-pyridin-2-yl)pyridin-2-ylethylidene}-benzene-1,4-diamine]diiron tetrabromide,
[2,5-dimethyl-N,N-bis-{(6-pyridin-2-yl)pyridin-2-ylmethylene}-benzene-1,4-diamine]diiron tetrachloride,
[2,5-dimethyl-N,N-bis-{(6-pyridin-2-yl)pyridin-2-ylethylidene}-benzene-1,4-diamine]diiron tetrachloride,
[2,5-dimethyl-N,N-bis-{(6-pyridin-2-yl)pyridin-2-ylmethylene}-benzene-1,4-diamine]diiron tetramethyl,
[2,5-dimethyl-N,N-bis-{(6-pyridin-2-yl)pyridin-2-ylethylidene}-benzene-1,4-diamine]diiron tetramethyl,
[2,3,5,6-tetramethyl-N,N-bis-{(6-pyridin-2-yl)pyridin-2-ylmethylene}-benzene-1,4-diamine]diiron tetrabromide,
[2,3,5,6-tetramethyl-N,N-bis-{(6-pyridin-2-yl)pyridin-2-ylethylidene}-benzene-1,4-diamine]diiron tetrabromide,
[2,3,5,6-tetramethyl-N,N-bis-{(6-pyridin-2-yl)pyridin-2-ylmethylene}-benzene-1,4-diamine]diiron tetrachloride,
[2,3,5,6-tetramethyl-N,N-bis-{(6-pyridin-2-yl)pyridin-2-ylethylidene}-benzene-1,4-diamine]diiron tetrachloride,
[2,3,5,6-tetramethyl-N,N-bis-{(6-pyridin-2-yl)pyridin-2-ylmethylene}-benzene-1,4-diamine]diiron tetramethyl,
[2,3,5,6-tetramethyl-N,N-bis-{(6-pyridin-2-yl)pyridin-2-ylethylidene}-benzene-1,4-diamine]diiron tetramethyl,
[2,3,5,6-tetramethyl-N,N-bis-{(6-pyridin-2-yl)pyridin-2-ylmethylene}-benzene-1,4-diamine]dicobalt tetrabromide,
[2,3,5,6-tetramethyl-N,N-bis-{(6-pyridin-2-yl)pyridin-2-ylethylidene}-benzene-1,4-diamine]dicobalt tetrabromide,
[2,3,5,6-tetramethyl-N,N-bis-{(6-pyridin-2-yl)pyridin-2-ylmethylene}-benzene-1,4-diamine]dicobalt tetrachloride,
[2,3,5,6-tetramethyl-N,N-bis-{(6-pyridin-2-yl)pyridin-2-ylethylidene}-benzene-1,4-diamine]dicobalt-tetrachloride,
[3,5,3',5'-tetramethyl-N,N-bis-(pyridin-2-ylmethylene)-biphenyl-4,4'-diamine]dinickel tetrabromide,
[3,5,3',5'-tetramethyl-N,N-bis-(pyridin-2-yl-ethylidene)-biphenyl-4,4'-diamine]dinickel tetrabromide,
[3,5,3',5'-tetraisopropyl-N,N,-bis-(pyridin-2-ylmethylene)-biphenyl-4,4'-diamine]dinickel tetrabromide,
[3,5,3',5'-tetraisopropyl-N,N,-bis-(pyridin-2-yl-ethylidene)-biphenyl-4,4'-diamine]dinickel tetrabromide,
[3,5,3',5'-tetramethyl-N,N-bis-(pyridin-2-ylmethylene)-biphenyl-4,4'-diamine]dinickel tetrachloride,
[3,5,3',5'-tetramethyl-N,N-bis-(pyridin-2-yl-ethylidene)-biphenyl-4,4'-diamine]dinickel tetrachloride,
[3,5,3',5'-tetraisopropyl-N,N,-bis-(pyridin-2-ylmethylene)-biphenyl-4,4'-diamine]dinickel tetrachloride,
[3,5,3',5'-tetraisopropyl-N,N,-bis-(pyridin-2-yl-ethylidene)-biphenyl-4,4'-diamine]dinickel tetrachloride,
[3,5,3',5'-tetramethyl-N,N-bis-(pyridin-2-ylmethylene)-biphenyl-4,4'-diamine]dinickel tetramethyl,
[3,5,3',5'-tetramethyl-N,N-bis-(pyridin-2-yl-ethylidene)-biphenyl-4,4'-diamine]dinickel tetramethyl,
[3,5,3',5'-tetraisopropyl-N,N,-bis-(pyridin-2-ylmethylene)-biphenyl-4,4'-diamine]dinickel tetramethyl,
[3,5,3',5'-tetraisopropyl-N,N,-bis-(pyridin-2-yl-ethylidene)-biphenyl-4,4'-diamine]dinickel tetramethyl,
[3,5,3',5'-tetramethyl-N,N-bis-(pyridin-2-ylmethylene)-biphenyl-4,4'-diamine]dipalladium tetrabromide,
[3,5,3',5'-tetramethyl-N,N-bis-(pyridin-2-yl-ethylidene)-biphenyl-4,4'-diamine]dipalladium tetrabromide,
[3,5,3',5'-tetraisopropyl-N,N,-bis-(pyridin-2-ylmethylene)-biphenyl-4,4'-diamine]dipalladium tetrabromide,
[3,5,3',5'-tetraisopropyl-N,N,-bis-(pyridin-2-yl-ethylidene)-biphenyl-4,4'-diamine]dipalladium tetrabromide,
[3,5,3',5'-tetramethyl-N,N-bis-(pyridin-2-ylmethylene)-biphenyl-4,4'-diamine]dipalladium tetrachloride,
[3,5,3',5'-tetramethyl-N,N-bis-(pyridin-2-yl-ethylidene)-biphenyl-4,4'-diamine]dipalladium tetrachloride,
[3,5,3',5'-tetraisopropyl-N,N,-bis-(pyridin-2-ylmethylene)-biphenyl-4,4'-diamine]dipalladium tetrachloride,
[3,5,3',5'-tetraisopropyl-N,N,-bis-(pyridin-2-yl-ethylidene)-biphenyl-4,4'-diamine]dipalladium tetrachloride,
[3,5,3',5'-tetramethyl-N,N-bis-(pyridin-2-ylmethylene)-biphenyl-4,4'-diamine]dipalladium tetramethyl,
[3,5,3',5'-tetramethyl-N,N-bis-(pyridin-2-yl-ethylidene)-biphenyl-4,4'-diamine]dipalladium tetramethyl,
[3,5,3',5'-tetraisopropyl-N,N,-bis-(pyridin-2-ylmethylene)-biphenyl-4,4'-diamine]dipalladium tetramethyl,
[3,5,3',5'-tetraisopropyl-N,N,-bis-(pyridin-2-yl-ethylidene)-biphenyl-4,4'-diamine]dipalladium tetramethyl,
[3,5,3',5'-tetramethyl-N,N-bis-(pyridin-2-ylmethylene)-biphenyl-4,4'-diamine]dicopper tetrabromide,
[3,5,3',5'-tetramethyl-N,N-bis-(pyridin-2-yl-ethylidene)-biphenyl-4,4'-diamine]dicopper tetrabromide,
[3,5,3',5'-tetraisopropyl-N,N,-bis-(pyridin-2-ylmethylene)-biphenyl-4,4'-diamine]dicopper tetrabromide,
[3,5,3',5'-tetraisopropyl-N,N,-bis-(pyridin-2-yl-ethylidene)-biphenyl-4,4'-diamine]dicopper tetrabromide,
[3,5,3',5'-tetramethyl-N,N-bis-(pyridin-2-ylmethylene)-biphenyl-4,4'-diamine]dicopper tetrachloride,
[3,5,3',5'-tetramethyl-N,N-bis-(pyridin-2-yl-ethylidene)-biphenyl-4,4'-diamine]dicopper tetrachloride,
[3,5,3',5'-tetraisopropyl-N,N,-bis-(pyridin-2-ylmethylene)-biphenyl-4,4'-diamine]dicopper tetrachloride,
[3,5,3',5'-tetraisopropyl-N,N,-bis-(pyridin-2-yl-ethylidene)-biphenyl-4,4'-diamine]dicopper tetrachloride,
[3,5,3',5'-tetramethyl-N,N-bis-(pyridin-2-ylmethylene)-biphenyl-4,4'-diamine]dicopper tetramethyl,
[3,5,3',5'-tetramethyl-N,N-bis-(pyridin-2-yl-ethylidene)-biphenyl-4,4'-diamine]dicopper tetramethyl,
[3,5,3',5'-tetraisopropyl-N,N,-bis-(pyridin-2-ylmethylene)-biphenyl-4,4'-diamine]dicopper tetramethyl,
[3,5,3',5'-tetraisopropyl-N,N,-bis-(pyridin-2-yl-ethylidene)-biphenyl-4,4'-diamine]dicopper tetramethyl,
[3,5,3',5'-tetramethyl-N,N-bis-{(6-pyridin-2-yl)pyridin-2-ylmethylene}-biphenyl-4,4'-diamine]diiron tetrabromide,
[3,5,3',5'-tetramethyl-N,N-bis-{(6-pyridin-2-yl)pyridin-2-ylethylidene}-biphenyl-4,4'-diamine]diiron tetrabromide,
[3,5,3',5'-tetraisopropyl-N,N-bis-{(6-pyridin-2-yl)pyridin-2-ylmethylene}-biphenyl-4,4'-diamine]diiron tetrabromide,
[3,5,3',5'-tetraisopropyl-N,N-bis-{(6-pyridin-2-yl)pyridin-2-ylethylidene}-biphenyl-4,4'-diamine]diiron tetrabromide,
[3,5,3',5'-tetramethyl-N,N-bis-{(6-pyridin-2-yl)pyridin-2-ylmethylene}-biphenyl-4,4'-diamine]diiron tetrachloride,
[3,5,3',5'-tetramethyl-N,N-bis-{(6-pyridin-2-yl)pyridin-2-ylethylidene}-biphenyl-4,4'-diamine]diiron tetrachloride,
[3,5,3',5'-tetraisopropyl-N,N-bis-{(6-pyridin-2-yl)pyridin-2-ylmethylene}-biphenyl-4,4'-diamine]diiron tetrachloride,
[3,5,3',5'-tetraisopropyl-N,N-bis-{(6-pyridin-2-yl)pyridin-2-ylethylidene}-biphenyl-4,4'-diamine]diiron tetrachloride,

[3,5,3',5'-tetramethyl-N,N-bis-{(6-pyridin-2-yl)pyridin-2-ylmethylene}-biphenyl-4,4'-diamine]diiron tetramethyl,
[3,5,3',5'-tetramethyl-N,N-bis-{(6-pyridin-2-yl)pyridin-2-ylethylidene}-biphenyl-4,4'-diamine]diiron tetramethyl,
[3,5,3',5'-tetraisopropyl-N,N-bis-{(6-pyridin-2-yl)pyridin-2-ylmethylene}-biphenyl-4,4'-diamine]diiron tetramethyl,
[3,5,3',5'-tetraisopropyl-N,N-bis-{(6-pyridin-2-yl)pyridin-2-ylethylidene}-biphenyl-4,4'-diamine]diiron tetramethyl,
[3,5,3',5'-tetramethyl-N,N-bis-{(6-pyridin-2-yl)pyridin-2-ylmethylene}-biphenyl-4,4'-diamine]dicobalt tetrabromide,
[3,5,3',5'-tetramethyl-N,N-bis-{(6-pyridin-2-yl)pyridin-2-ylethylidene}-biphenyl-4,4'-diamine]dicobalt tetrabromide,
[3,5,3',5'-tetraisopropyl-N,N-bis-{(6-pyridin-2-yl)pyridin-2-ylmethylene}-biphenyl-4,4'-diamine]dicobalt tetrabromide,
[3,5,3',5'-tetraisopropyl-N,N-bis-{(6-pyridin-2-yl)pyridin-2-ylethylidene}-biphenyl-4,4'-diamine]dicobalt tetrabromide,
[3,5,3',5'-tetramethyl-N,N-bis-{(6-pyridin-2-yl)pyridin-2-ylmethylene}-biphenyl-4,4'-diamine]dicobalt tetrachloride,
[3,5,3',5'-tetramethyl-N,N-bis-{(6-pyridin-2-yl)pyridin-2-ylethylidene}-biphenyl-4,4'-diamine]dicobalt tetrachloride,
[3,5,3',5'-tetraisopropyl-N,N-bis-{(6-pyridin-2-yl)pyridin-2-ylmethylene}-biphenyl-4,4'-diamine]dicobalt tetrachloride,
[3,5,3',5'-tetraisopropyl-N,N-bis-{(6-pyridin-2-yl)pyridin-2-ylethylidene}-biphenyl-4,4'-diamine]dicobalt tetrachloride,
[3,5,3',5'-tetramethyl-N,N-bis-{(6-pyridin-2-yl)pyridin-2-ylmethylene}-biphenyl-4,4'-diamine]dicobalt tetramethyl,
[3,5,3',5'-tetramethyl-N,N-bis-{(6-pyridin-2-yl)pyridin-2-ylethylidene}-biphenyl-4,4'-diamine]dicobalt tetramethyl,
[3,5,3',5'-tetraisopropyl-N,N-bis-{(6-pyridin-2-yl)pyridin-2-ylmethylene}-biphenyl-4,4'-diamine]dicobalt tetramethyl,
[3,5,3',5'-tetraisopropyl-N,N-bis-{(6-pyridin-2-yl)pyridin-2-ylethylidene}-biphenyl-4,4'-diamine]dicobalt tetramethyl,
[bis-{4-(pyridin-2-yl-methyleneamino)-3,5-dimethylphenyl}-methane]dinickel tetrabromide,
[bis-{4-(pyridin-2-yl-ethylideneamino)-3,5-dimethylphenyl}-methane]dinickel tetrabromide,
[bis-{4-(pyridin-2-yl-methyleneamino)-3,5-diisopropylphenyl}-methane]dinickel tetrabromide,
[bis-{4-(pyridin-2-yl-ethylideneamino)-3,5-diisopropylphenyl}-methane]dinickel tetrabromide,
[bis-{4-(pyridin-2-yl-methyleneamino)-3,5-dimethylphenyl}-toluene]dinickel tetrabromide,
[bis-{4-(pyridin-2-yl-ethylideneamino)-3,5-dimethylphenyl}-toluene]dinickel tetrabromide,
[bis-{4-(pyridin-2-yl-methyleneamino)-3,5-diisopropylphenyl}-toluene]dinickel tetrabromide,
[bis-{4-(pyridin-2-yl-ethylideneamino)-3,5-diisopropylphenyl}-toluene]dinickel tetrabromide,
[bis-{4-(pyridin-2-yl-methyleneamino)-3,5-dimethylphenyl}-4-bromotoluene]dinickel tetrabromide,
[bis-{4-(pyridin-2-yl-ethylideneamino)-3,5-dimethylphenyl}-4-bromotoluene]dinickel tetrabromide,
[bis-{4-(pyridin-2-yl-methyleneamino)-3,5-diisopropylphenyl}-4-bromotoluene]dinickel tetrabromide,
[bis-{4-(pyridin-2-yl-ethylideneamino)-3,5-diisopropylphenyl}-4-bromotoluene]dinickel tetrabromide,
[bis-{4-(pyridin-2-yl-methyleneamino)-3,5-dimethylphenyl}-4-hydroxytoluene]dinickel tetrabromide,
[bis-{4-(pyridin-2-yl-ethylideneamino)-3,5-dimethylphenyl}-4-hydroxytoluene]dinickel tetrabromide,
[bis-{4-(pyridin-2-yl-methyleneamino)-3,5-diisopropylphenyl}-4-hydroxytoluene]dinickel tetrabromide,
[bis-{4-(pyridin-2-yl-ethylideneamino)-3,5-diisopropylphenyl}-4-hydroxytoluene]dinickel tetrabromide,
[bis-{4-(pyridin-2-yl-methyleneamino)-3,5-dimethylphenyl}-4-nitrotoluene]dinickel tetrabromide,
[bis-{4-(pyridin-2-yl-ethylideneamino)-3,5-dimethylphenyl}-4-nitrotoluene]dinickel tetrabromide,
[bis-{4-(pyridin-2-yl-methyleneamino)-3,5-diisopropylphenyl}-4-nitrotoluene]dinickel tetrabromide,
[bis-{4-(pyridin-2-yl-ethylideneamino)-3,5-diisopropylphenyl}-4-nitrotoluene]dinickel tetrabromide,
[bis-{4-(pyridin-2-yl-methyleneamino)-3,5-dimethylphenyl}-4-isopropyltoluene]dinickel tetrabromide,
[bis-{4-(pyridin-2-yl-ethylideneamino)-3,5-dimethylphenyl}-4-isopropyltoluene]dinickel tetrabromide,
[bis-{4-(pyridin-2-yl-methyleneamino)-3,5-diisopropylphenyl}-4-isopropyltoluene]dinickel tetrabromide,
[bis-{4-(pyridin-2-yl-ethylideneamino)-3,5-diisopropylphenyl}-4-isopropyltoluene]dinickel tetrabromide,
[{4-(pyridin-2-yl-methyleneamino)-3,5-dimethylphenyl}-{4-(pyridin-2-yl-methyleneamino)-3,5-diisopropylphenyl}-methane]dinickel tetrabromide,
[bis-{4-(pyridin-2-yl-methyleneamino)-3,5-dimethylphenyl}-methane]dinickel tetrachloride,
[bis-{4-(pyridin-2-yl-ethylideneamino)-3,5-dimethylphenyl}-methane]dinickel tetrachloride,
[bis{4-(pyridin-2-yl-methyleneamino)-3,5-diisopropylphenyl}-methane]dinickel tetrachloride,
[bis-{4-(pyridin-2-yl-ethylideneamino)-3,5-diisopropylphenyl}-methane]dinickel tetrachloride,
[bis-{4-(pyridin-2-yl-methyleneamino)-3,5-dimethylphenyl}-toluene]dinickel tetrachloride,
[bis-{4-(pyridin-2-yl-ethylideneamino)-3,5-dimethylphenyl}-toluene]dinickel tetrachloride,
[bis-{4-(pyridin-2-yl-methyleneamino)-3,5-diisopropylphenyl}-toluene]dinickel tetrachloride,
[bis-{4-(pyridin-2-yl-ethylideneamino)-3,5-diisopropylphenyl}-toluene]dinickel tetrachloride,
[bis-{4-(pyridin-2-yl-methyleneamino)-3,5-dimethylphenyl}-4-bromotoluene]dinickel tetrachloride,
[bis-{4-(pyridin-2-yl-ethylideneamino)-3,5-dimethylphenyl}-4-bromotoluene]dinickel tetrachloride,
[bis-{4-(pyridin-2-yl-methyleneamino)-3,5-diisopropylphenyl}-4-bromotoluene]dinickel tetrachloride,
[bis-{4-(pyridin-2-yl-ethylideneamino)-3,5-diisopropylphenyl}-4-bromotoluene]dinickel tetrachloride,
[bis-{4-(pyridin-2-yl-methyleneamino)-3,5-dimethylphenyl}-4-hydroxytoluene]dinickel tetrachloride,
[bis-{4-(pyridin-2-yl-ethylideneamino)-3,5-dimethylphenyl}-4-hydroxytoluene]dinickel tetrachloride,
[bis-{4-(pyridin-2-yl-methyleneamino)-3,5-diisopropylphenyl}-4-hydroxytoluene]dinickel tetrachloride,
[bis-{4-(pyridin-2-yl-ethylideneamino)-3,5-diisopropylphenyl}-4-hydroxytoluene]dinickel tetrachloride,
[bis-{4-(pyridin-2-yl-methyleneamino)-3,5-dimethylphenyl}-4-nitrotoluene]dinickel tetrachloride,
[bis-{4-(pyridin-2-yl-ethylideneamino)-3,5-dimethylphenyl}-4-nitrotoluene]dinickel tetrachloride,
[bis-{4-(pyridin-2-yl-methyleneamino)-3,5-diisopropylphenyl}-4-nitrotoluene]dinickel tetrachloride,

[bis-{4-(pyridin-2-yl-ethylideneamino)-3,5-diisopropylphenyl}-4-nitrotoluene]dinickel tetrachloride,
[bis-{4-(pyridin-2-yl-methyleneamino)-3,5-dimethylphenyl}-4-isopropyltoluene]dinickel tetrachloride,
[bis-{4-(pyridin-2-yl-ethylideneamino)-3,5-dimethylphenyl}-4-isopropyltoluene]dinickel tetrachloride,
[bis-{4-(pyridin-2-yl-methyleneamino)-3,5-diisopropylphenyl}-4-isopropyltoluene]dinickel tetrachloride,
[bis-{4-(pyridin-2-yl-ethylideneamino)-3,5-diisopropylphenyl}-4-isopropyltoluene]dinickel tetrachloride,
[{4-(pyridin-2-yl-methyleneamino)-3,5-dimethylphenyl}-{4-(pyridin-2-yl-methyleneamino)-3,5-diisopropylphenyl}-methane]dinickel tetrachloride,
[bis-{4-(pyridin-2-yl-methyleneamino)-3,5-dimethylphenyl}-methane]dinickel tetramethyl,
[bis-{4-(pyridin-2-yl-ethylideneamino)-3,5-dimethylphenyl}-methane]dinickel tetramethyl,
[bis-{4-(pyridin-2-yl-methyleneamino)-3,5-diisopropylphenyl}-methane]dinickel tetramethyl,
[bis-{4-(pyridin-2-yl-ethylideneamino)-3,5-diisopropylphenyl}-methane]dinickel tetramethyl, [bis-{4-(pyridin-2-yl-methyleneamino)-3,5-dimethylphenyl}-toluene]dinickel tetramethyl,
[bis-{4-(pyridin-2-yl-ethylideneamino)-3,5-dimethylphenyl}-toluene]dinickel tetramethyl,
[bis {4-(pyridin-2-yl-methyleneamino)-3,5-diisopropylphenyl}-toluene]dinickel tetramethyl,
[bis-{4-(pyridin-2-yl-ethylideneamino)-3,5-diisopropylphenyl}-toluene]dinickel tetramethyl,
[bis-{4-(pyridin-2-yl-methyleneamino)-3,5-dimethylphenyl}-4-bromotoluene]dinickel tetramethyl,
[bis-{4-(pyridin-2-yl-ethylideneamino)-3,5-dimethylphenyl}-4-bromotoluene]dinickel tetramethyl,
[bis-{4-(pyridin-2-yl-methyleneamino)-3,5-diisopropylphenyl}-4-bromotoluene]dinickel tetramethyl
[bis-{4-(pyridin-2-yl-ethylideneamino)-3,5-diisopropylphenyl}-4-bromotoluene]dinickel tetramethyl,
[bis-{4-(pyridin-2-yl-methyleneamino)-3,5-dimethylphenyl}-4-hydroxytoluene]dinickel tetramethyl,
[bis-{4-(pyridin-2-yl-ethylideneamino)-3,5-dimethylphenyl}-4-hydroxytoluene]dinickel tetramethyl,
[bis-{4-(pyridin-2-yl-methyleneamino)-3,5-diisopropylphenyl}-4-hydroxytoluene]dinickel tetramethyl,
[bis-{4-(pyridin-2-yl-ethylideneamino)-3,5-diisopropylphenyl}-4-hydroxytoluene]dinickel tetramethyl,
[bis-{4-(pyridin-2-yl-methyleneamino)-3,5-dimethylphenyl}-4-nitrotoluene]dinickel tetramethyl,
[bis-{4-(pyridin-2-yl-ethylideneamino)-3,5-dimethylphenyl}-4-nitrotoluene]dinickel tetramethyl,
[bis-{4-(pyridin-2-yl-methyleneamino)-3,5-diisopropylphenyl}-4-nitrotoluene]dinickel tetramethyl,
[bis-{4-(pyridin-2-yl-ethylideneamino)-3,5-diisopropylphenyl}-4-nitrotoluene]dinickel tetramethyl,
[bis-{4-(pyridin-2-yl-methyleneamino)-3,5-dimethylphenyl}-4-isopropyltoluene]dinickel tetramethyl,
[bis-{4-(pyridin-2-yl-ethylideneamino)-3,5-dimethylphenyl}-4-isopropyltoluene]dinickel tetramethyl,
[bis-{4-(pyridin-2-yl-methyleneamino)-3,5-diisopropylphenyl}-4-isopropyltoluene]dinickel tetramethyl,
[bis-{4-(pyridin-2-yl-ethylideneamino)-3,5-diisopropylphenyl}-4-isopropyltoluene]dinickel tetramethyl,
[{4-(pyridin-2-yl-methyleneamino)-3,5-dimethylphenyl}-{4-(pyridin-2-yl-methyleneamino)-3,5-diisopropylphenyl}-methane]dinickel tetramethyl,
[bis-{4-(pyridin-2-yl-methyleneamino)-3,5-dimethylphenyl}-methane]dipalladium tetrabromide,
[bis-{4-(pyridin-2-yl-ethylideneamino)-3,5-dimethylphenyl}-methane]dipalladium tetrabromide,
[bis-{4-(pyridin-2-yl-methyleneamino)-3,5-diisopropylphenyl}-methane]dipalladium tetrabromide,
[bis-{4-(pyridin-2-yl-ethylideneamino)-3,5-diisopropylphenyl}-methane]dipalladium tetrabromide,
[bis-{4-(pyridin-2-yl-methyleneamino)-3,5-dimethylphenyl}-toluene]dipalladium tetrabromide,
[bis-{4-(pyridin-2-yl-ethylideneamino)-3,5-dimethylphenyl}-toluene]dipalladium tetrabromide,
[bis-{4-(pyridin-2-yl-methyleneamino)-3,5-diisopropylphenyl}-toluene]dipalladium tetrabromide,
[bis-{4-(pyridin-2-yl-ethylideneamino)-3,5-diisopropylphenyl}-toluene]dipalladium tetrabromide,
[bis-{4-(pyridin-2-yl-methyleneamino)-3,5-dimethylphenyl}-4-bromotoluene]dipalladium tetrabromide,
[bis{4-(pyridin-2-yl-ethylideneamino)-3,5-dimethylphenyl}-4-bromotoluene]dipalladium tetrabromide,
[bis {4-(pyridin-2-yl-methyleneamino)-3,5-diisopropylphenyl}-4-bromotoluene]dipalladium tetrabromide,
[bis-{4-(pyridin-2-yl-ethylideneamino)-3,5-diisopropylphenyl}-4-bromotoluene]dipalladium tetrabromide,
[bis-{4-(pyridin-2-yl-methyleneamino)-3,5-dimethylphenyl}-4-hydroxytoluene]dipalladium tetrabromide,
[bis-{4-(pyridin-2-yl-ethylideneamino)-3,5-dimethylphenyl}-4-hydroxytoluene]dipalladium tetrabromide,
[bis-{4-(pyridin-2-yl-methyleneamino)-3,5-diisopropylphenyl}-4-hydroxytoluene]dipalladium tetrabromide,
[bis-{4-(pyridin-2-yl-ethylideneamino)-3,5-diisopropylphenyl}-4-hydroxytoluene]dipalladium tetrabromide,
[bis-{4-(pyridin-2-yl-methyleneamino)-3,5-dimethylphenyl}-4-nitrotoluene]dipalladium tetrabromide,
[bis-{4-(pyridin-2-yl-ethylideneamino)-3,5-dimethylphenyl}-4-nitrotoluene]dipalladium tetrabromide,
[bis-{4-(pyridin-2-yl-methyleneamino)-3,5-diisopropylphenyl}-4-nitrotoluene]dipalladium tetrabromide,
[bis-{4-(pyridin-2-yl-ethylideneamino)-3,5-diisopropylphenyl}-4-nitrotoluene]dipalladium tetrabromide,
[bis-{4-(pyridin-2-yl-methyleneamino)-3,5-dimethylphenyl}-4-isopropyltoluene]dipalladium tetrabromide,
[bis-{4-(pyridin-2-yl-ethylideneamino)-3,5-dimethylphenyl}-4-isopropyltoluene]dipalladium tetrabromide,
[bis-{4-(pyridin-2-yl-methyleneamino)-3,5-diisopropylphenyl}-4-isopropyltoluene]dipalladium tetrabromide,
[bis-{4-(pyridin-2-yl-ethylideneamino)-3,5-diisopropylphenyl}-4-isopropyltoluene]dipalladium tetrabromide,
[{4-(pyridin-2-yl-methyleneamino)-3,5-dimethylphenyl}-{4-(pyridin-2-yl-methyleneamino)-3,5-diisopropylphenyl}-methane]dipalladium tetrabromide,
[bis-{4-(pyridin-2-yl-methyleneamino)-3,5-dimethylphenyl}-methane]dipalladium tetrachloride,
[bis-{4-(pyridin-2-yl-ethylideneamino)-3,5-dimethylphenyl}-methane]dipalladium tetrachloride,
[bis-{4-(pyridin-2-yl-methyleneamino)-3,5-diisopropylphenyl}-methane]dipalladium tetrachloride,
[bis-{4-(pyridin-2-yl-ethylideneamino)-3,5-diisopropylphenyl}-methane]dipalladium tetrachloride,
[bis-{4-(pyridin-2-yl-methyleneamino)-3,5-dimethylphenyl}-toluene]dipalladium tetrachloride,
[bis-{4-(pyridin-2-yl-ethylideneamino)-3,5-dimethylphenyl}-toluene]dipalladium tetrachloride,
[bis-{4-(pyridin-2-yl-methyleneamino)-3,5-diisopropylphenyl}-toluene]dipalladium tetrachloride,
[bis-{4-(pyridin-2-yl-ethylideneamino)-3,5-diisopropylphenyl}-toluene]dipalladium tetrachloride,
[bis-{4-(pyridin-2-yl-methyleneamino)-3,5-dimethylphenyl}-4-bromotoluene]dipalladium tetrachloride,

[bis-{4-(pyridin-2-yl-ethylideneamino)-3,5-dimethylphenyl}-4-bromotoluene]dipalladium tetrachloride,
[bis-{4-(pyridin-2-yl-methyleneamino)-3,5-diisopropylphenyl}-4-bromotoluene]dipalladium tetrachloride,
[bis-{4-(pyridin-2-yl-ethylideneamino)-3,5-diisopropylphenyl}-4-bromotoluene]dipalladium tetrachloride,
[bis-{4-(pyridin-2-yl-methyleneamino)-3,5-dimethylphenyl}-4-hydroxytoluene]dipalladium tetrachloride,
[bis-4-(pyridin-2-yl-ethylideneamino)-3,5-dimethylphenyl-4-hydroxytoluene]dipalladium tetrachloride,
[bis-{4-(pyridin-2-yl-methyleneamino)-3,5-diisopropylphenyl}-4-hydroxytoluene]dipalladium tetrachloride,
[bis-{4-(pyridin-2-yl-ethylideneamino)-3,5-diisopropylphenyl}-4-hydroxytoluene]dipalladium tetrachloride,
[bis-{4-(pyridin-2-yl-methyleneamino)-3,5-dimethylphenyl}-4-nitrotoluene]dipalladium tetrachloride,
[bis-{4-(pyridin-2-yl-ethylideneamino)-3,5-dimethylphenyl}-4-nitrotoluene]dipalladium tetrachloride,
[bis-{4-(pyridin-2-yl-methyleneamino)-3,5-diisopropylphenyl}-4-nitrotoluene]dipalladium tetrachloride,
[bis-{4-(pyridin-2-yl-ethylideneamino)-3,5-diisopropylphenyl}-4-nitrotoluene]dipalladium tetrachloride,
[bis-{4-(pyridin-2-yl-methyleneamino)-3,5-dimethylphenyl}-4-isopropyltoluene]dipalladium tetrachloride,
[bis-{4-(pyridin-2-yl-ethylideneamino)-3,5-dimethylphenyl}-4-isopropyltoluene]dipalladium tetrachloride,
[bis-{4-(pyridin-2-yl-methyleneamino)-3,5-diisopropylphenyl}-4-isopropyltoluene]dipalladium tetrachloride,
[bis-{4-(pyridin-2-yl-ethylideneamino)-3,5-diisopropylphenyl}-4-isopropyltoluene]dipalladium tetrachloride,
[{4-(pyridin-2-yl-methyleneamino)-3,5-dimethylphenyl}-{4-(pyridin-2-yl-methyleneamino)-3,5-diisopropylphenyl}-methane]dipalladium tetrachloride,
[bis-{4-(pyridin-2-yl-methyleneamino)-3,5-dimethylphenyl}-methane]dipalladium tetramethyl,
[bis-{4-(pyridin-2-yl-ethylideneamino)-3,5-dimethylphenyl}-methane]dipalladium tetramethyl,
[bis-{4-(pyridin-2-yl-methyleneamino)-3,5-diisopropylphenyl}-methane]dipalladium tetramethyl,
[bis-{4-(pyridin-2-yl-ethylideneamino)-3,5-diisopropylphenyl}-methane]dipalladium tetramethyl,
[bis-{4-(pyridin-2-yl-methyleneamino)-3,5-dimethylphenyl}-toluene]dipalladium tetramethyl,
[bis-{4-(pyridin-2-yl-ethylideneamino)-3,5-dimethylphenyl}-toluene]dipalladium tetramethyl,
[bis-{4-(pyridin-2-yl-methyleneamino)-3,5-diisopropylphenyl}-toluene]dipalladium tetramethyl,
[bis-{4-(pyridin-2-yl-ethylideneamino)-3,5-diisopropylphenyl}-toluene]dipalladium tetramethyl,
[bis-{4-(pyridin-2-yl-methyleneamino)-3,5-dimethylphenyl}-4-bromotoluene]dipalladium tetramethyl,
[bis-{4-(pyridin-2-yl-ethylideneamino)-3,5-dimethylphenyl}-4-bromotoluene]dipalladium tetramethyl,
[bis-{4-(pyridin-2-yl-methyleneamino)-3,5-diisopropylphenyl}-4-bromotoluene]dipalladium tetramethyl,
[bis-{4-(pyridin-2-yl-ethylideneamino)-3,5-diisopropylphenyl}-4-bromotoluene]dipalladium tetramethyl,
[bis-{4-(pyridin-2-yl-methyleneamino)-3,5-dimethylphenyl}-4-hydroxytoluene]dipalladium tetramethyl,
[bis-{4-(pyridin-2-yl-ethylideneamino)-3,5-dimethylphenyl}-4-hydroxytoluene]dipalladium tetramethyl,
[bis-{4-(pyridin-2-yl-methyleneamino)-3,5-diisopropylphenyl}-4-hydroxytoluene]dipalladium tetramethyl,
[bis-{4-(pyridin-2-yl-ethylideneamino)-3,5-diisopropylphenyl}-4-hydroxytoluene]dipalladium tetramethyl,
[bis-{4-(pyridin-2-yl-methyleneamino)-3,5-dimethylphenyl}-4-nitrotoluene]dipalladium tetramethyl,
[bis-{4-(pyridin-2-yl-ethylideneamino)-3,5-dimethylphenyl}-4-nitrotoluene]dipalladium tetramethyl,
[bis-{4-(pyridin-2-yl-methyleneamino)-3,5-diisopropylphenyl}-4-nitrotoluene]dipalladium tetramethyl,
[bis-{4-(pyridin-2-yl-ethylideneamino)-3,5-diisopropylphenyl}-4-nitrotoluene]dipalladium tetramethyl,
[bis-{4-(pyridin-2-yl-methyleneamino)-3,5-dimethylphenyl}-4-isopropyltoluene]dipalladium tetramethyl,
[bis-{4-(pyridin-2-yl-ethylideneamino)-3,5-dimethylphenyl}-4-isopropyltoluene]dipalladium tetramethyl,
[bis-{4-(pyridin-2-yl-methyleneamino)-3,5-diisopropylphenyl}-4-isopropyltoluene]dipalladium tetramethyl,
[bis-{4-(pyridin-2-yl-ethylideneamino)-3,5-diisopropylphenyl}-4-isopropyltoluene]dipalladium tetramethyl,
[{4-(pyridin-2-yl-methyleneamino)-3,5-dimethylphenyl}-{4-(pyridin-2-yl-methyleneamino)-3,5-diisopropylphenyl}-methane]dipalladium tetramethyl,
[bis-{4-(pyridin-2-yl-methyleneamino)-3,5-dimethylphenyl}-methane]dicopper tetrabromide,
[bis-{4-(pyridin-2-yl-ethylideneamino)-3,5-dimethylphenyl}-methane]dicopper tetrabromide,
[bis-{4-(pyridin-2-yl-methyleneamino)-3,5-diisopropylphenyl}-methane]dicopper tetrabromide,
[bis-{4-(pyridin-2-yl-ethylideneamino)-3,5-diisopropylphenyl}-methane]dicopper tetrabromide,
[bis-{4-(pyridin-2-yl-methyleneamino)-3,5-dimethylphenyl}-toluene]dicopper tetrabromide,
[bis-{4-(pyridin-2-yl-ethylideneamino)-3,5-dimethylphenyl}-toluene]dicopper tetrabromide,
[bis-{4-(pyridin-2-yl-methyleneamino)-3,5-diisopropylphenyl}-toluene]dicopper tetrabromide,
[bis{4-(pyridin-2-yl-ethylideneamino)-3,5-diisopropylphenyl}-toluene]dicopper tetrabromide,
[bis-{4-(pyridin-2-yl-methyleneamino)-3,5-dimethylphenyl}-4-bromotoluene]dicopper tetrabromide,
[bis-{4-(pyridin-2-yl-ethylideneamino)-3,5-dimethylphenyl}-4-bromotoluene]dicopper tetrabromide,
[bis-{4-(pyridin-2-yl-methyleneamino)-3,5-diisopropylphenyl}-4-bromotoluene]dicopper tetrabromide,
[bis-{4-(pyridin-2-yl-ethylideneamino)-3,5-diisopropylphenyl}-4-bromotoluene]dicopper tetrabromide,
[bis-{4-(pyridin-2-yl-methyleneamino)-3,5-dimethylphenyl}-4-hydroxytoluene]dicopper tetrabromide,
[bis-{4-(pyridin-2-yl-ethylideneamino)-3,5-dimethylphenyl}-4-hydroxytoluene]dicopper tetrabromide,
[bis-{4-(pyridin-2-yl-methyleneamino)-3,5-diisopropylphenyl}-4-hydroxytoluene]dicopper tetrabromide,
[bis-{4-(pyridin-2-yl-ethylideneamino)-3,5-diisopropylphenyl}-4-hydroxytoluene]dicopper tetrabromide,
[bis-{4-(pyridin-2-yl-methyleneamino)-3,5-dimethylphenyl}-4-nitrotoluene]dicopper tetrabromide,
[bis-{4-(pyridin-2-yl-ethylideneamino)-3,5-dimethylphenyl}-4-nitrotoluene]dicopper tetrabromide,
[bis-{4-(pyridin-2-yl-methyleneamino)-3,5-diisopropylphenyl}-4-nitrotoluene]dicopper tetrabromide,
[bis-{4-(pyridin-2-yl-ethylideneamino)-3,5-diisopropylphenyl}-4-nitrotoluene]dicopper tetrabromide,
[bis-{4-(pyridin-2-yl-methyleneamino)-3,5-dimethylphenyl}-4-isopropyltoluene]dicopper tetrabromide,
[bis-{4-(pyridin-2-yl-ethylideneamino)-3,5-dimethylphenyl}-4-isopropyltoluene]dicopper tetrabromide,
[bis-{4-(pyridin-2-yl-methyleneamino)-3,5-diisopropylphenyl}-4-isopropyltoluene]dicopper tetrabromide,
[bis-{4-(pyridin-2-yl-ethylideneamino)-3,5-diisopropylphenyl}-4-isopropyltoluene]dicopper tetrabromide,

[{4-(pyridin-2-yl-methyleneamino)-3,5-dimethylphenyl}-{4-(pyridin-2-yl-methyleneamino)-3,5-diisopropylphenyl}-methane]dicopper tetrabromide,
[bis-{4-(pyridin-2-yl-methyleneamino)-3,5-dimethylphenyl}-methane]dicopper tetrachloride,
[bis-{4-(pyridin-2-yl-ethylideneamino)-3,5-dimethylphenyl}-methane]dicopper tetrachloride,
[bis-{4-(pyridin-2-yl-methyleneamino)-3,5-diisopropylphenyl}-methane]dicopper tetrachloride,
[bis-{4-(pyridin-2-yl-ethylideneamino)-3,5-diisopropylphenyl}-methane]dicopper tetrachloride,
[bis-{4-(pyridin-2-yl-methyleneamino)-3,5-dimethylphenyl}-toluene]dicopper tetrachloride,
[bis-{4-(pyridin-2-yl-ethylideneamino)-3,5-dimethylphenyl}-toluene]dicopper tetrachloride,
[bis-{4-(pyridin-2-yl-methyleneamino)-3,5-diisopropylphenyl}-toluene]dicopper tetrachloride
[bis-{4-(pyridin-2-yl-ethylideneamino)-3,5-diisopropylphenyl}-toluene]dicopper tetrachloride,
[bis-{4-(pyridin-2-yl-methyleneamino)-3,5-dimethylphenyl}-4-bromotoluene]dicopper tetrachloride,
[bis-{4-(pyridin-2-yl-ethylideneamino)-3,5-dimethylphenyl}-4-bromotoluene]dicopper tetrachloride,
[bis-{4-(pyridin-2-yl-methyleneamino)-3,5-diisopropylphenyl}-4-bromotoluene]dicopper tetrachloride,
[bis-{4-(pyridin-2-yl-ethylideneamino)-3,5-diisopropylphenyl}-4-bromotoluene]dicopper tetrachloride,
[bis-{4-(pyridin-2-yl-methyleneamino)-3,5-dimethylphenyl}-4-hydroxytoluene]dicopper tetrachloride,
[bis-{4-(pyridin-2-yl-ethylideneamino)-3,5-dimethylphenyl}-4-hydroxytoluene]dicopper tetrachloride,
[bis-{4-(pyridin-2-yl-methyleneamino)-3,5-diisopropylphenyl}-4-hydroxytoluene]dicopper tetrachloride,
[bis-{4-(pyridin-2-yl-ethylideneamino)-3,5-diisopropylphenyl}-4-hydroxytoluene]dicopper tetrachloride,
[bis-{4-(pyridin-2-yl-methyleneamino)-3,5-dimethylphenyl}-4-nitrotoluene]dicopper tetrachloride,
[bis-{4-(pyridin-2-yl-ethylideneamino)-3,5-dimethylphenyl}-4-nitrotoluene]dicopper tetrachloride,
[bis-{4-(pyridin-2-yl-methyleneamino)-3,5-diisopropylphenyl}-4-nitrotoluene]dicopper tetrachloride,
[bis-{4-(pyridin-2-yl-ethylideneamino)-3,5-diisopropylphenyl}-4-nitrotoluene]dicopper tetrachloride,
[bis-{4-(pyridin-2-yl-methyleneamino)-3,5-dimethylphenyl}-4-isopropyltoluene]dicopper tetrachloride,
[bis-{4-(pyridin-2-yl-ethylideneamino)-3,5-dimethylphenyl}-4-isopropyltoluene]dicopper tetrachloride,
[bis-{4-(pyridin-2-yl-methyleneamino)-3,5-diisopropylphenyl}-4-isopropyltoluene]dicopper tetrachloride,
[bis-{4-(pyridin-2-yl-ethylideneamino)-3,5-diisopropylphenyl}-4-isopropyltoluene]dicopper tetrachloride,
[{4-(pyridin-2-yl-methyleneamino)-3,5-dimethylphenyl}-{4-(pyridin-2-yl-methyleneamino)-3,5-diisopropylphenyl}-methane]dicopper tetrachloride,
[bis-{4-(pyridin-2-yl-methyleneamino)-3,5-dimethylphenyl}-methane]dicopper tetramethyl,
[bis-{4-(pyridin-2-yl-ethylideneamino)-3,5-dimethylphenyl}-methane]dicopper tetramethyl,
[bis-{4-(pyridin-2-yl-methyleneamino)-3,5-diisopropylphenyl}-methane]dicopper tetramethyl,
[bis-{4-(pyridin-2-yl-ethylideneamino)-3,5-diisopropylphenyl}-methane]dicopper tetramethyl,
[bis-{4-(pyridin-2-yl-methyleneamino)-3,5-dimethylphenyl}-toluene]dicopper tetramethyl,
[bis-{4-(pyridin-2-yl-ethylideneamino)-3,5-dimethylphenyl}-toluene]dicopper tetramethyl,
[bis-{4-(pyridin-2-yl-methyleneamino)-3,5-diisopropylphenyl}-toluene]dicopper tetramethyl,
[bis-{4-(pyridin-2-yl-ethylideneamino)-3,5-diisopropylphenyl}-toluene]dicopper tetramethyl,
[bis-{4-(pyridin-2-yl-methyleneamino)-3,5-dimethylphenyl}-4-bromotoluene]dicopper tetramethyl,
[bis-{4-(pyridin-2-yl-ethylideneamino)-3,5-dimethylphenyl}-4-bromotoluene]dicopper tetramethyl,
[bis-{4-(pyridin-2-yl-methyleneamino)-3,5-diisopropylphenyl}-4-bromotoluene]dicopper tetramethyl,
[bis-{4-(pyridin-2-yl-ethylideneamino)-3,5-diisopropylphenyl}-4-bromotoluene]dicopper tetramethyl,
[bis-{4-(pyridin-2-yl-methyleneamino)-3,5-dimethylphenyl}-4-hydroxytoluene]dicopper tetramethyl,
[bis-{4-(pyridin-2-yl-ethylideneamino)-3,5-dimethylphenyl}-4-hydroxytoluene]dicopper tetramethyl,
[bis-{4-(pyridin-2-yl-methyleneamino)-3,5-diisopropylphenyl}-4-hydroxytoluene]dicopper tetramethyl,
[bis-{4-(pyridin-2-yl-ethylideneamino)-3,5-diisopropylphenyl}-4-hydroxytoluene]dicopper tetramethyl,
[bis-{4-(pyridin-2-yl-methyleneamino)-3,5-dimethylphenyl}-4-nitrotoluene]dicopper tetramethyl,
[bis-{4-(pyridin-2-yl-ethylideneamino)-3,5-dimethylphenyl}-4-nitrotoluene]dicopper tetramethyl,
[bis-{4-(pyridin-2-yl-methyleneamino)-3,5-diisopropylphenyl}-4-nitrotoluene]dicopper tetramethyl,
[bis-{4-(pyridin-2-yl-ethylideneamino)-3,5-diisopropylphenyl}-4-nitrotoluene]dicopper tetramethyl,
[bis-{4-(pyridin-2-yl-methyleneamino)-3,5-dimethylphenyl}-4-isopropyltoluene]dicopper tetramethyl,
[bis-{4-(pyridin-2-yl-ethylideneamino)-3,5-dimethylphenyl}-4-isopropyltoluene]dicopper tetramethyl,
[bis-{4-(pyridin-2-yl-methyleneamino)-3,5-diisopropylphenyl}-4-isopropyltoluene]dicopper tetramethyl,
[bis-{4-(pyridin-2-yl-ethylideneamino)-3,5-diisopropylphenyl}-4-isopropyltoluene]dicopper tetramethyl,
[{4-(pyridin-2-yl-methyleneamino)-3,5-dimethylphenyl}-{4-(pyridin-2-yl-methyleneamino)-3,5-diisopropylphenyl}-methane]dicopper tetramethyl,
[bis-{((6-pyridin-2-yl)pyridin-2-yl-methyleneamino)-3,5-dimethylphenyl}-methane]diiron tetrabromide,
[bis-{((6-pyridin-2-yl)pyridin-2-yl-ethylideneamino)-3,5-dimethylphenyl}-methane]diiron tetrabromide,
[bis-{((6-pyridin-2-yl)pyridin-2-yl-methyleneamino)-3,5-diisopropylphenyl}-methane]diiron tetrabromide,
[bis-{((6-pyridin-2-yl)pyridin-2-yl-ethylideneamino)-3,5-diisopropylphenyl}-methane]diiron tetrabromide,
[bis-{((6-pyridin-2-yl)pyridin-2-yl-methyleneamino)-3,5-dimethylphenyl}-methane]diiron tetrachloride,
[bis-{((6-pyridin-2-yl)pyridin-2-yl-ethylideneamino)-3,5-dimethylphenyl}-methane]diiron tetrachloride,
[bis-{(6-pyridin-2-yl)pyridin-2-yl-methyleneamino)-3,5-diisopropylphenyl}-methane]diiron tetrachloride,
[bis-{(6-pyridin-2-yl)pyridin-2-yl-ethylideneamino)-3,5-diisopropylphenyl}-methane]diiron tetrachloride,
bis-{((6-pyridin-2-yl)pyridin-2-yl-methyleneamino)-3,5-dimethylphenyl}-methane]diiron tetramethyl,
[bis-{((6-pyridin-2-yl)pyridin-2-yl-ethylideneamino)-3,5-dimethylphenyl}-methane]diiron tetramethyl,
[bis-{(6-pyridin-2-yl)pyridin-2-yl-methyleneamino)-3,5-diisopropylphenyl}-methane]diiron tetramethyl,
[bis-{(6-pyridin-2-yl)pyridin-2-yl-ethylideneamino)-3,5-diisopropylphenyl}-methane]diiron tetramethyl,
[bis-{((6-pyridin-2-yl)pyridin-2-yl-methyleneamino)-3,5-dimethylphenyl}-methane]dicobalt tetrabromide,
[bis-{((6-pyridin-2-yl)pyridin-2-yl-ethylideneamino)-3,5-dimethylphenyl}-methane]dicobalt tetrabromide,

[bis-{(6-pyridin-2-yl)pyridin-2-yl-methyleneamino)-3,5-diisopropylphenyl]-methane]dicobalt tetrabromide,
[bis-{(6-pyridin-2-yl)pyridin-2-yl-ethylideneamino)-3,5-diisopropylphenyl}-methane]dicobalt tetrabromide,
[bis-{((6-pyridin-2-yl)pyridin-2-yl-methyleneamino)-3,5-dimethylphenyl}-methane]dicobalt tetrachloride,
[bis-{((6-pyridin-2-yl)pyridin-2-yl-ethylideneamino)-3,5-dimethylphenyl}-methane]dicobalt tetrachloride,
[bis-{(6-pyridin-2-yl)pyridin-2-yl-methyleneamino)-3,5-diisopropylphenyl}-methane]dicobalt tetrachloride,
[bis-{(6-pyridin-2-yl)pyridin-2-yl-ethylideneamino)-3,5-diisopropylphenyl}-methane]dicobalt tetrachloride,
[bis-{((6-pyridin-2-yl)pyridin-2-yl-methyleneamino)-3,5-dimethylphenyl}-methane]dicobalt tetramethyl,
[bis-{((6-pyridin-2-yl)pyridin-2-yl-ethylideneamino)-3,5-dimethylphenyl}-methane]dicobalt tetramethyl,
[bis-{(6-pyridin-2-yl)pyridin-2-yl-methyleneamino)-3,5-diisopropylphenyl}-methane]dicobalt tetramethyl, and
[bis-{(6-pyridin-2-yl)pyridin-2-yl-ethylideneamino)-3,5-diisopropylphenyl}-methane]dicobalt tetramethyl.

Particularly preferred transition metal complexes include:
[2,3,5,6-tetramethyl-N,N-bis-(pyridin-2-ylmethylene)-benzene-1,4-diamine]dinickel tetrachloride,
[2,3,5,6-tetramethyl-N,N-bis-(pyridin-2-ylethylidene)-benzene-1,4-diamine]dinickel tetrachloride,
[2,3,5,6-tetramethyl-N-(pyridin-2-ylethylidene)-N-(pyridin-2-ylmethylene)-benzene-1,4-diamine]dinickel tetrachloride,
[N,N-bis-(pyridin-2-ylmethylene)-benzene-1,4-diamine]dinickel tetramethyl,
[N,N-bis-(pyridin-2-ylethylidene)-benzene-1,4-diamine]dinickel tetramethyl,
[N-(pyridin-2-ylethylidene)-N-(pyridin-2-ylmethylene)-benzene-1,4-diamine]dinickel tetramethyl,
[2,3,5,6-tetramethyl-N,N-bis-{(6-pyridin-2-yl)pyridin-2-yl-methylene}-benzene-1,4-diamine]diiron tetrachloride,
[2,3,5,6-tetramethyl-N,N-bis-{(6-pyridin-2-yl)pyridin-2-yl-ethylidene}-benzene-1,4-diamine]diiron tetrachloride,
[2,3,5,6-tetramethyl-N,N-bis-{(6-pyridin-2-yl)pyridin-2-yl-methylene}-benzene-1,4-diamine]diiron tetramethyl,
[2,3,5,6-tetramethyl-N,N-bis-{(6-pyridin-2-yl)pyridin-2-yl-ethylidene}-benzene-1,4-diamine]diiron tetramethyl,
[2,3,5,6-tetramethyl-N,N-bis-{(6-pyridin-2-yl)pyridin-2-yl-methylene}-benzene-1,4-diamine]dicobalt tetrachloride,
[2,3,5,6-tetramethyl-N,N-bis-{(6-pyridin-2-yl)pyridin-2-yl-ethylidene}-benzene-1,4-diamine]dicobalt tetrachloride,
[2,3,5,6-tetramethyl-N,N-bis-{(6-pyridin-2-yl)pyridin-2-yl-methylene}-benzene-1,4-diamine]dicobalt tetramethyl,
[2,3,5,6-tetramethyl-N,N-bis-{(6-pyridin-2-yl)pyridin-2-yl-ethylidene}-benzene-1,4-diamine]dicobalt tetramethyl,
[3,5,3',5'-tetraisopropyl-N,N,-bis-(pyridin-2-yl-ethylidene)-biphenyl-4,4'-diamine]dinickel tetrabromide,
[3,5,3',5'-tetramethyl-N,N-bis-(pyridin-2-ylmethylene)-biphenyl-4,4'-diamine]dinickel tetrachloride,
[3,5,3',5'-tetramethyl-N,N-bis-(pyridin-2-yl-ethylidene)-biphenyl-4,4'-diamine]dinickel tetrachloride,
[3,5,3',5'-tetraisopropyl-N,N,-bis-(pyridin-2-ylmethylene)-biphenyl-4,4'-diamine]dinickel tetrachloride,
[3,5,3',5'-tetraisopropyl-N,N,-bis-(pyridin-2-yl-ethylidene)-biphenyl-4,4'-diamine]dinickel tetrachloride,
[3,5,3',5'-tetramethyl-N,N-bis-(pyridin-2-ylmethylene)-biphenyl-4,4'-diamine]dinickel tetramethyl,
[3,5,3',5'-tetramethyl-N,N-bis-(pyridin-2-yl-ethylidene)-biphenyl-4,4'-diamine]dinickel tetramethyl,
[3,5,3',5'-tetraisopropyl-N,N,-bis-(pyridin-2-ylmethylene)-biphenyl-4,4'-diamine]dinickel tetramethyl,
[3,5,3',5'-tetraisopropyl-N,N,-bis-(pyridin-2-yl-ethylidene)-biphenyl-4,4'-diamine]dinickel tetramethyl,
[3,5,3',5'-tetramethyl-N,N-bis-{(6-pyridin-2-yl)pyridin-2-ylmethylene}-biphenyl-4,4'-diamine]diiron tetrachloride,
[3,5,3',5'-tetramethyl-N,N-bis-{(6-pyridin-2-yl)pyridin-2-ylethylidene}-biphenyl-4,4'-diamine]diiron tetrachloride,
[3,5,3',5'-tetraisopropyl-N,N-bis-{(6-pyridin-2-yl)pyridin-2-ylmethylene}-biphenyl-4,4'-diamine]diiron tetrachloride,
[3,5,3',5'-tetraisopropyl-N,N-bis-{(6-pyridin-2-yl)pyridin-2-ylethylidene}-biphenyl-4,4'-diamine]diiron tetrachloride,
[3,5,3',5'-tetramethyl-N,N-bis-{(6-pyridin-2-yl)pyridin-2-ylmethylene}-biphenyl-4,4'-diamine]diiron tetramethyl,
[3,5,3',5'-tetramethyl-N,N-bis-{(6-pyridin-2-yl)pyridin-2-ylethylidene}-biphenyl-4,4'-diamine]diiron tetramethyl,
[3,5,3',5'-tetraisopropyl-N,N-bis-{(6-pyridin-2-yl)pyridin-2-ylmethylene}-biphenyl-4,4'-diamine]diiron tetramethyl,
[3,5,3',5'-tetraisopropyl-N,N-bis-{(6-pyridin-2-yl)pyridin-2-ylethylidene}-biphenyl-4,4'-diamine]diiron tetramethyl,
[3,5,3',5'-tetramethyl-N,N-bis-{(6-pyridin-2-yl)pyridin-2-ylmethylene}-biphenyl-4,4'-diamine]dicobalt tetrachloride,
[3,5,3',5'-tetramethyl-N,N-bis-{(6-pyridin-2-yl)pyridin-2-ylethylidene}-biphenyl-4,4'-diamine]dicobalt tetrachloride,
[3,5,3',5'-tetraisopropyl-N,N-bis-{(6-pyridin-2-yl)pyridin-2-ylmethylene}-biphenyl-4,4'-diamine]dicobalt tetrachloride,
[3,5,3',5'-tetraisopropyl-N,N-bis-{(6-pyridin-2-yl)pyridin-2-ylethylidene}-biphenyl-4,4'-diamine]dicobalt tetrachloride,
[3,5,3',5'-tetramethyl-N,N-bis-{(6-pyridin-2-yl)pyridin-2-ylmethylene}-biphenyl-4,4'-diamine]dicobalt tetramethyl,
[3,5,3',5'-tetramethyl-N,N-bis-{(6-pyridin-2-yl)pyridin-2-ylethylidene}-biphenyl-4,4'-diamine]dicobalt tetramethyl,
[3,5,3',5'-tetraisopropyl-N,N-bis-{(6-pyridin-2-yl)pyridin-2-ylmethylene}-biphenyl-4,4'-diamine]dicobalt tetramethyl,
[3,5,3',5'-tetraisopropyl-N,N-bis-{(6-pyridin-2-yl)pyridin-2-ylethylidene}-biphenyl-4,4'-diamine]dicobalt tetramethyl,
[bis-{4-(pyridin-2-yl-methyleneamino)-3,5-dimethylphenyl}-methane]dinickel tetrachloride,
[bis-{4-(pyridin-2-yl-ethylideneamino)-3,5-dimethylphenyl}-methane]dinickel tetrachloride,
[bis-{4-(pyridin-2-yl-methyleneamino)-3,5-diisopropylphenyl}-methane]dinickel tetrachloride,
[bis-{4-(pyridin-2-yl-ethylideneamino)-3,5-diisopropylphenyl}-methane]dinickel tetrachloride,
[bis-{4-(pyridin-2-yl-methyleneamino)-3,5-dimethylphenyl}-toluene]dinickel tetrachloride,
[bis-{4-(pyridin-2-yl-ethylideneamino)-3,5-dimethylphenyl}-toluene]dinickel tetrachloride,
[bis-{4-(pyridin-2-yl-methyleneamino)-3,5-diisopropylphenyl}-toluene]dinickel tetrachloride,
[bis-{4-(pyridin-2-yl-ethylideneamino)-3,5-diisopropylphenyl}-toluene]dinickel tetrachloride,
[bis-{4-(pyridin-2-yl-methyleneamino)-3,5-dimethylphenyl}-4-bromotoluene]dinickel tetrachloride,
[bis-{4-(pyridin-2-yl-ethylideneamino)-3,5-dimethylphenyl}-4-bromotoluene]dinickel tetrachloride,

[bis-{4-(pyridin-2-yl-methyleneamino)-3,5-diisopropylphenyl}-4-bromotoluene]dinickel tetrachloride,
[bis-{4-(pyridin-2-yl-ethylideneamino)-3,5-diisopropylphenyl}-4-bromotoluene]dinickel tetrachloride,
[bis-{4-(pyridin-2-yl-methyleneamino)-3,5-dimethylphenyl}-4-hydroxytoluene]dinickel tetrachloride,
[bis-{4-(pyridin-2-yl-ethylideneamino)-3,5-dimethylphenyl}-4-hydroxytoluene]dinickel tetrachloride,
[bis-{4-(pyridin-2-yl-methyleneamino)-3,5-diisopropylphenyl}-4-hydroxytoluene]dinickel tetrachloride,
[bis-{4-(pyridin-2-yl-ethylideneamino)-3,5-diisopropylphenyl}-4-hydroxytoluene]dinickel tetrachloride,
[bis-{4-(pyridin-2-yl-methyleneamino)-3,5-dimethylphenyl}-4-nitrotoluene]dinickel tetrachloride,
[bis-{4-(pyridin-2-yl-ethylideneamino)-3,5-dimethylphenyl}-4-nitrotoluene]dinickel tetrachloride,
[bis-{4-(pyridin-2-yl-methyleneamino)-3,5-diisopropylphenyl}-4-nitrotoluene]dinickel tetrachloride,
[bis-{4-(pyridin-2-yl-ethylideneamino)-3,5-diisopropylphenyl}-4-nitrotoluene]dinickel tetrachloride,
[bis-{4-(pyridin-2-yl-methyleneamino)-3,5-dimethylphenyl}-4-isopropyltoluene]dinickel tetrachloride,
[bis-{4-(pyridin-2-yl-ethylideneamino)-3,5-dimethylphenyl}-4-isopropyltoluene]dinickel tetrachloride,
[bis-{4-(pyridin-2-yl-methyleneamino)-3,5-diisopropylphenyl}-4-isopropyltoluene]dinickel tetrachloride,
[bis-{4-(pyridin-2-yl-ethylideneamino)-3,5-diisopropylphenyl}-4-isopropyltoluene]dinickel tetrachloride,
[{4-(pyridin-2-yl-methyleneamino)-3,5-dimethylphenyl}-{4-(pyridin-2-yl-methyleneamino)-3,5-diisopropylphenyl}-methane]dinickel tetrachloride,
[bis-{4-(pyridin-2-yl-methyleneamino)-3,5-dimethylphenyl}-methane]dinickel tetramethyl,
[bis-{4-(pyridin-2-yl-ethylideneamino)-3,5-dimethylphenyl}-methane]dinickel tetramethyl,
[bis-{4-(pyridin-2-yl-methyleneamino)-3,5-diisopropylphenyl}-methane]dinickel tetramethyl,
[bis-{4-(pyridin-2-yl-ethylideneamino)-3,5-diisopropylphenyl}-methane]dinickel tetramethyl,
[bis-{4-(pyridin-2-yl-methyleneamino)-3,5-dimethylphenyl}-toluene]dinickel tetramethyl,
[bis-{4-(pyridin-2-yl-ethylideneamino)-3,5-dimethylphenyl}-toluene]dinickel tetramethyl,
[bis-{4-(pyridin-2-yl-methyleneamino)-3,5-diisopropylphenyl}-toluene]dinickel tetramethyl,
[bis-{4-(pyridin-2-yl-ethylideneamino)-3,5-diisopropylphenyl}-toluene]dinickel tetramethyl
[bis-{4-(pyridin-2-yl-methyleneamino)-3,5-dimethylphenyl}-4-bromotoluene]dinickel tetramethyl,
[bis-{4-(pyridin-2-yl-ethylideneamino)-3,5-dimethylphenyl}-4-bromotoluene]dinickel tetramethyl
[bis-{4-(pyridin-2-yl-methyleneamino)-3,5-diisopropylphenyl}-4-bromotoluene]dinickel tetramethyl,
[bis-{4-(pyridin-2-yl-ethylideneamino)-3,5-diisopropylphenyl}-4-bromotoluene]dinickel tetramethyl,
[bis-{4-(pyridin-2-yl-methyleneamino)-3,5-dimethylphenyl}-4-hydroxytoluene]dinickel tetramethyl,
[bis-{4-(pyridin-2-yl-ethylideneamino)-3,5-dimethylphenyl}-4-hydroxytoluene]dinickel tetramethyl,
[bis-{4-(pyridin-2-yl-methyleneamino)-3,5-diisopropylphenyl}-4-hydroxytoluene]dinickel tetramethyl,
[bis-{4-(pyridin-2-yl-ethylideneamino)-3,5-diisopropylphenyl}-4-hydroxytoluene]dinickel tetramethyl,
[bis-{4-(pyridin-2-yl-methyleneamino)-3,5-dimethylphenyl}-4-nitrotoluene]dinickel tetramethyl,
[bis-{4-(pyridin-2-yl-ethylideneamino)-3,5-dimethylphenyl}-4-nitrotoluene]dinickel tetramethyl,
[bis-{4-(pyridin-2-yl-methyleneamino)-3,5-diisopropylphenyl}-4-nitrotoluene]dinickel tetramethyl,
[bis-{4-(pyridin-2-yl-ethylideneamino)-3,5-diisopropylphenyl}-4-nitrotoluene]dinickel tetramethyl,
[bis-{4-(pyridin-2-yl-methyleneamino)-3,5-dimethylphenyl}-4-isopropyltoluene]dinickel tetramethyl,
[bis-{4-(pyridin-2-yl-ethylideneamino)-3,5-dimethylphenyl}-4-isopropyltoluene]dinickel tetramethyl,
[bis-{4-(pyridin-2-yl-methyleneamino)-3,5-diisopropylphenyl}-4-isopropyltoluene]dinickel tetramethyl,
[bis-{4-(pyridin-2-yl-ethylideneamino)-3,5-diisopropylphenyl}-4-isopropyltoluene]dinickel tetramethyl,
[{4-(pyridin-2-yl-methyleneamino)-3,5-dimethylphenyl}-{4-(pyridin-2-yl-methyleneamino)-3,5-diisopropylphenyl}-methane]dinickel tetramethyl,
[bis-{((6-pyridin-2-yl)pyridin-2-yl-methyleneamino)-3,5-dimethylphenyl}-methane]diiron tetrachloride,
[bis-{((6-pyridin-2-yl)pyridin-2-yl-ethylideneamino)-3,5-dimethylphenyl}-methane]diiron tetrachloride,
[bis-{(6-pyridin-2-yl)pyridin-2-yl-methyleneamino)-3,5-diisopropylphenyl}-methane]diiron tetrachloride,
[bis-{(6-pyridin-2-yl)pyridin-2-yl-ethylideneamino)-3,5-diisopropylphenyl}-methane]diiron tetrachloride,
bis-{((6-pyridin-2-yl)pyridin-2-yl-methyleneamino)-3,5-dimethylphenyl}-methane]diiron tetramethyl,
[bis-{((6-pyridin-2-yl)pyridin-2-yl-ethylideneamino)-3,5-dimethylphenyl}-methane]diiron tetramethyl,
[bis-{(6-pyridin-2-yl)pyridin-2-yl-methyleneamino)-3,5-diisopropylphenyl}-methane]diiron tetramethyl,
[bis-{(6-pyridin-2-yl)pyridin-2-yl-ethylideneamino)-3,5-diisopropylphenyl}-methane]diiron tetramethyl,
[bis-{((6-pyridin-2-yl)pyridin-2-yl-methyleneamino)-3,5-dimethylphenyl}-methane]dicobalt tetrachloride,
[bis-{((6-pyridin-2-yl)pyridin-2-yl-ethylideneamino)-3,5-dimethylphenyl}-methane]dicobalt tetrachloride,
[bis-{(6-pyridin-2-yl)pyridin-2-yl-methyleneamino)-3,5-diisopropylphenyl}-methane]dicobalt tetrachloride,
[bis-{(6-pyridin-2-yl)pyridin-2-yl-ethylideneamino)-3,5-diisopropylphenyl}-methane]dicobalt tetrachloride,
[bis-{((6-pyridin-2-yl)pyridin-2-yl-methyleneamino)-3,5-dimethylphenyl}-methane]dicobalt tetramethyl,
[bis-{((6-pyridin-2-yl)pyridin-2-yl-ethylideneamino)-3,5-dimethylphenyl}-methane]dicobalt tetramethyl,
[bis-{(6-pyridin-2-yl)pyridin-2-yl-methyleneamino)-3,5-diisopropylphenyl}-methane]dicobalt tetramethyl, and
[bis-{(6-pyridin-2-yl)pyridin-2-yl-ethylideneamino)-3,5-diisopropylphenyl}-methane]dicobalt tetramethyl.

Transition metal complexes of this invention are typically prepared by reaction of the tetradentate or hexdentate ligand with the desired metal halide, preferably a metal dihalide, in an appropriate solvent, preferably n-butanol, and heating the reaction mixture.

Mixed Catalysts

Mixed catalyst systems can also be used, for example, the invention catalyst can be used in conjunction with a "second catalyst" in the same reactor or in a series of reactors where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Invention polymerization catalyst systems can comprise additional olefin polymerization catalysts, sometimes referred to as the "second catalyst". These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937, 299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: monocyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154-3156. U.S. Pat. No. 5,318,935 describes bridged and unbridged, bis-amido catalyst compounds of Group-4 metals capable of alpha-olefins polymerization. Bridged bis(arylamido) Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis (arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention" ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.,* 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.,* 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Activators and Catalyst Activation

The transition metal compounds, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such trimethyl aluminum, tri-isobutyl aluminum, triethyl aluminum, and tri-isopropyl aluminum. Co-activators are typically used in combination with Lewis acid activators and ionic activators when the pre-catalyst is not a dihydrocarbyl or dihydride complex.

The alumoxane component useful as an activator typically is an oligomeric aluminum compound represented by the general formula $(R^x\text{—Al—O})_n$, which is a cyclic compound, or $R^x(R^x\text{—Al—O})_n AlR^x_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3\text{-}3,5\text{-}(CF_3)_2))_4]$, $[Ph_3C][B((C_6H_3\text{-}3,5\text{-}(CF_3)_2))_4]$, $[NH_4][B(C_6H_5)_4]$ or Lewis acidic activators such as $B(C_6F_5)_3$ or $B(C_6H_5)_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri(n-butyl) ammonium tetrakis (pentafluorophenyl)borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as $([B(C_6F_5)_3(X')]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

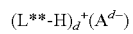

$(L^{}\text{-H})_d^+(A^{d-})$ wherein $L^{}$ is an neutral Lewis base;

H is hydrogen;

$(L^{**}\text{-H})^+$ is a Bronsted acid $A^{d-}$ is a non-coordinating anion having the charge d– d is an integer from 1 to 3.

The cation component, $(L^{}\text{-H})_d^+$ may include Bronsted acids such as protons or protonated Lewis bases or reducible Lewis acids capable of protonating or abstracting a moiety, such as an alkyl or aryl, from the precatalyst after alkylation. The activating cation $(L^{}\text{-H})_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{**}\text{-H})_d^+$ may also be a moiety such as silver, tropylium, carbeniums, ferroceniums and mixtures, preferably carboniums and ferroceniums; most preferably triphenyl carbonium.

The anion component $A^{d-}$ include those having the formula $[M^{k+}Q_n]^{d-}$ wherein k is an integer from 1 to 3; n is an integer from 2-6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (tert-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, trimethylammonium tetrakis(perfluoronaphthyl) borate, triethylammonium tetrakis(perfluoronaphthyl) borate, tripropylammonium tetrakis(perfluoronaphthyl) borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanilinium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(tert-butyl) ammonium tetrakis(3,5-bis(trifluoromethyl)phenyl)borate, N,N-dimethylanilinium tetrakis(3,5-bis(trifluoromethyl) phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, tropillium tetrakis-(2,3,4,6-tetrafluorophenyl)borate, triphenylcarbenium tetrakis-(2,3,4, 6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

Most preferably, the ionic stoichiometric activator ($L^{**}$-$H)_d^+$ ($A^{d-}$) is N,N-dimethylanilinium tetrakis(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst precursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Noncoordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst precursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris(pentafluorophenyl)boron In some embodiments, scavenging compounds are used with stoichiometric activators. Typical aluminum or boron alkyl components useful as scavengers are represented by the general formula $R^xJZ_2$ where J is aluminum or boron, $R^x$ is as previously defined above, and each Z is independently $R^x$ or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

The solubility of invention catalyst precursors allows for the ready preparation of supported catalysts. To prepare uniform supported catalysts, the catalyst precursor preferably dissolves in the chosen solvent. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 $m^2/g$, a pore volume of 0.1-4.0 cc/g and an average particle size of 10-500 μm. Some embodiments select a surface area of 50-500 $m^2/g$, a pore volume of 0.5-3.5 cc/g, or an average particle size of 20-200 μm. Other embodiments select a surface area of 100-400 $m^2/g$, a pore volume of 0.8-3.0 cc/g, and an average particle size of 30-100 μm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1,3-methylpentene-1,3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, C1 to C10 alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5 phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2 dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-1,0-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl) ethyl]-3,5,7,9,11,13,15-heptacyclopentylpentacyclo [9.5.1.1$^{3,9}$.1$^{5,15}$.1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2,-tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)- ethanesulfonyl fluoride, acrylic acid 2,2,3,3,4,4,5,5,6,6,7,7,8,8,8-pentadecafluoro-octyl ester, and 1,1,2,2-tetrafluoro-2-(1,1,2,2,3,3,4,4-octafluoro-dec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4 methylpentene-1,3-methylpentene-1,3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1,3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises:

a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69–6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfP)_4]^-$ or $B(pfP)_3$ (perfluorophenyl=pfp=$C_6F_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068% kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. patent applications 60/431,185 filed Dec. 5, 2002; 60/431,077, filed Dec. 5, 2002; and 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

1. In another embodiment, this invention relates to a transition metal catalyst compound represented by the formula:

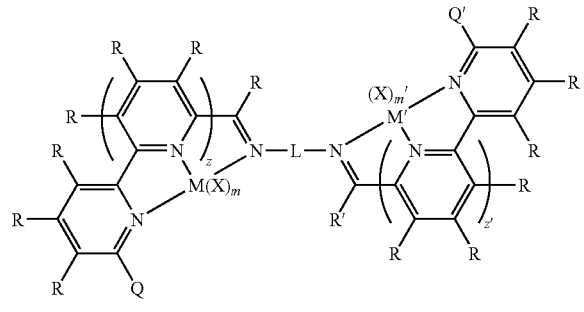

where:

M and M' are, independently, a group 8, 9, 10 or 11 transition metal;

each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;

R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;

each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;

m and m' are, independently, 0, 1, 2, or 3;

z and z' are, independently, 0, 1, 2, or 3;

N is nitrogen;

Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and L is a hydrocarbyl, substituted hydrocarbyl, halocarbyl, substituted halocarbyl, silylcarbyl, substituted silylcarbyl, germylcarbyl, or substituted germylcarbyl substituent.

2. The compound of paragraph 1 wherein M and M' are, independently Ni, Co, Pd, Cu, or Fe.

3. The compound of paragraph 1 or 2 wherein each R group is, independently, selected from the group consisting of C1 to C20 hydrocarbyls, C1 to C20 substituted phenyls, and all isomers thereof.

4. The compound of any of the above paragraphs wherein each R group is, independently, selected from the group consisting of ethyl, methyl, propyl, butyl, pentyl, hexyl, septyl, octyl, nonyl, decyl, undecyl, dodecyl, phenyl, methylphenyl, and all isomers thereof.

5. The compound of any of the above paragraphs wherein R' is selected from the group consisting of C1 to C20 hydrocarbyls, C1 to C20 substituted phenyls, and all isomers thereof.

6. The compound of any of the above paragraphs wherein R' is selected from the group consisting of ethyl, methyl, propyl, butyl, pentyl, hexyl, septyl, octyl, nonyl, decyl, undecyl, dodecyl, phenyl, methylphenyl, and all isomers thereof.

7. The compound of any of the above paragraphs wherein each Q and Q' is, independently, selected from the group consisting of C1 to C20 hydrocarbyls, C1 to C20 substituted phenyls, and all isomers thereof.

8. The compound of any of the above paragraphs wherein each Q and Q' is, independently, selected from the group consisting of ethyl, methyl, propyl, butyl, pentyl, hexyl, septyl, octyl, nonyl, decyl, undecyl, dodecyl, phenyl, methylphenyl, and all isomers thereof.

9. The compound of any of the above paragraphs wherein each X is, independently, selected from the group consisting of chlorine, bromine, fluorine, methyl, ethyl, propyl, isopropyl, butyl, t-butyl, pentyl, hexyl, phenyl, and methylphenyl.

10. The compound of any of the above paragraphs wherein each X is, independently, selected from the group consisting of chlorine, bromine, fluorine, methyl, ethyl, propyl, isopropyl, butyl, t-butyl and pentyl.

11. The compound of any of the above paragraphs wherein L is an aryl group.

12. The compound of any of the above paragraphs wherein z and z' are the same.

13. The compound of any of the above paragraphs wherein z and z' are zero.

14. The compound of any of paragraphs 1-12 wherein z and z' are 1.

15. The compound of any of paragraphs 1-12 wherein z and z' are 2.

16. The compound of any of paragraphs 1-12 wherein z and z' are 3.

17. The compound of any of paragraphs 1-11 wherein z and z' are different.

18. The compound of paragraphs 17 wherein z is zero and z' is 1.

19. The compound of any of the above paragraphs wherein m and m' are the same.

20. The compound of any of the above paragraphs wherein M and M' are the same.

21. The compound of any of the above paragraphs wherein Q and Q' are the same.

22. The compound of any of paragraphs 1-18, 20 or 21 wherein m and m' are different.

23. The compound of any of paragraphs 1-19, 21 or 22 wherein M and M' are different.

24. The compound of any of paragraphs 1-20, 22 or 23 wherein Q and Q' are different.

25. The compound of any of the above paragraphs wherein each R, R', Q and Q' is independently selected from the group consisting of hydrogen, methyl, ethyl, isopropyl, and phenyl.

26. A catalyst system comprising activator and a transition metal catalyst compound of any of paragraphs 1-25.

27. The catalyst system of paragraph 26 wherein the activator is an alumoxane.

28. The catalyst system of paragraph 26 wherein the activator is a non-coordinating anion.

29. The catalyst system of paragraph 26 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(tert-butyl) ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5 bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

30. The catalyst system of paragraph 26 wherein the activator is selected from the group consisting of: N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, and triphenylcarbenium tetra (perfluorophenyl)borate.

31. The catalyst system of paragraph 26 wherein the activator is selected from the group consisting of: methyl alumoxane, modified methyl alumoxane, ethyl alumoxane, iso-butyl alumoxane, triphenyl boron, tris-perfluorophenyl boron, tris-perfluorophenyl aluminum, dimethylanilinium tetrakis perfluorophenyl borate, triphenyl carbonium tetrakis perfluorophenyl borate, dimethylanilinium tetrakis perfluorophenyl aluminate, and trisperfluoronaphthyl boron.

32. A method to polymerize unsaturated monomers comprising contacting one or more monomers with the catalyst system of paragraphs 26-29.

33. The method of paragraph 32 wherein the monomer comprises one or more olefins.

34. The method of paragraph 33 wherein the olefins comprise ethylene.

35. The method of paragraph 33 or 34 wherein the olefins comprises propylene.

36. The method of paragraph 32, 33 or 34 wherein the polymerization occurs in the gas phase.

37. The method of paragraph 32, 33 or 34 wherein the polymerization occurs in the solution phase.

38. The method of paragraph 32, 33 or 34 wherein the polymerization occurs in the slurry phase.

39. The method of paragraphs 32 to 38 wherein the polymerization occurs at a temperature above 70° C. and a pressure above 5 MPa.

40. A polymer produce by the method of any of paragraphs 32-49.

41. An article of manufacture comprising the polymer of paragraph 40.

42. A method to oligomerize a monomer comprising contacting monomer with the catalyst system of any of paragraphs 26-31.

43. An oligomer produce by the method of paragraph 42.

44. An article of manufacture comprising the oligomer of paragraph 43.

EXPERIMENTAL

Synthesis of Pre-Catalysts

In the following formulae Me is methyl, iPr is isopropyl, and Ph is phenyl.

The present invention is illustrated in the following examples.

Preparation of Linker (L)

The electrospray (ES) mass spectra were recorded using a micromass Quattra LC mass spectrometer with dichloromethane or methanol as the matrix [Masslynx software. open-access autosampler injection]. The infrared spectra were recorded with Universal ATR sampling accessories on a Perkin Elmer Spectrum One FTIR instrument. $^1$H and $^{13}$C NMR spectra were recorded at ambient temperature on a Bruker ARX spectrometer 250/300 MHz; chemical shifts (ppm) are referred to the residual protic solvent peaks. The reagents 2,6-dimethylaniline, 2,6-diisopropylaniline, 2,3,5, 6-tetramethyl-benzene-1,4-diamine, formaldehyde (37/40 wt. % solution in water), cetyltrimethylammoniumbromide (CTAB), benzaldehyde, palladium on carbon paste (5%), p-bromobenzaldehyde, p-hydroxybenzaldehyde, p-isopropylbenzaldehyde and p-nitrobenzaldehyde were purchased from Aldrich Chemical Co. and used without further purification. Formic acid (98%) was purchased from Fisons PLC and used without further purification. The compounds, 4-bromo-2,6-dimethylaniline [H. Suzuki, K. Nakamura and M. Takeshima, *Bull. Chem. Soc. Jpn.,* 1971, 44, 2248], 4-bromo-2,6 diisopropylaniline [J. H. Oskam, H. H. Fox, K. B. Yap, D. H. McConville, R. O'Dell, B. J. Lichtenstein and R. R. Schrock, *J. Organomet. Chem.,* 1993, 459, 185] were prepared according to the indicated journal articles.

Example 1

Preparation of 3,3',5,5'-tetramethylbiphenyl-4,4'-diamine (1a)

Compound 1a was prepared using the procedure described in P. Bamfield and P. M. Quan, Synthesis, 1978, 537 using 4-bromo-2,6-dimethylaniline (10.00 g, 50 mmol), CTAB (2.00 g, 5.5 mmol, 0.11 eq.), 5% palladium on charcoal (0.80 g, 50% paste), sodium hydroxide (21.1 ml, 8.0M, 0.169 mol) and sodium formate (2×3.40 g, 100 mmol, 2 eq.) in water (30 ml).

Example 2

Preparation of 3,3',5,5'-tetraisoproplbiphenyl-4,4'-diamine (1b)

A mixture containing 4-bromo-2,6-diisopropylaniline (12.80 g, 50 mmol), CTAB (2.00 g, 5.5 mmol, 0.11 eq.), 5% palladium on charcoal (0.80 g, 50% paste), sodium hydroxide (21.1 ml, 8.0M, 0.169 mol) and sodium formate (3.40 g, 50 mmol, 1 eq.) was mixed in water (30 ml) and heated to reflux for 4 hours. A further quantity of sodium formate (3.40 g, 50 mmol, 1 eq.) was then added to the boiling solution and the reaction mixture stirred vigorously under reflux for a further 20 hours. The reaction mixture was cooled to room temperature, the solid filtered off and the residue washed with copious amounts of chloroform. The organic phase was separated from the aqueous layer and dried over magnesium sulfate. The organic phase was rapidly filtered through silica and the silica washed several times with chloroform. The filtrate was concentrated, distilled under reduced pressure at 150° C. (0.1 mmHg) to remove the remaining 2,6-disopropylaniline to give 1b as a dark reddish solid (0.52 g, 5.2%). Recystallisation of 1b was achieved from hexane.

Compound 1b: ES mass spectrum, m/z 353 [M+H]$^+$; IR (cm$^{-1}$), 3401, 3368 (N—H); $^1$H NMR (CDCl$_3$), δ 1.25 (d, 24H, $^3$J(HH) 7.2, CH(CH$_3$)$_2$), 2.92 (sept, 4H, CH(CH$_3$)$_2$), 3.70 (br, 4H, NH$_2$), 7.11 (s, 4H, Ar—H); $^{13}$C NMR (CDCl$_3$, $^1$H gated decoupled), δ 21.5 (s, CH$_3$), 27.1 (s, CH), 120.7 (s, Ar), 131.6 (s, Ar), 132.1 (s, Ar), 137.8 (s, Ar). Anal. (C$_{25}$H$_{38}$N$_2$) calcd: C, 81.97; H, 10.38; N, 7.65. Found: C, 82.18; H, 10.09; N, 7.79%. In addition, a single crystal X-ray diffraction study of 1b has confirmed the structural type.

Example 3

Preparation of 4,4'-methylenebis(2,6-dimethylaniline) (2a)

A modification of the preparation described in C. A. Hunter, J. Am. Chem. Soc., 1992, 114, 5303, was employed. To a solution of 2,6-dimethylaniline (10.00 g, 0.083 mol) and formaldehyde (4.03 g, 0.054 mol, 0.65 eq.) was added dilute hydrochloric acid (2.2 ml, 0.1 M). The biphasic solution was stirred at 70° C. overnight. The dark reddish solution was left to cool to ambient temperature and diluted with dichloromethane (15 ml). The minimum amount of concentrated hydrochloric acid (2 ml) was introduced and the solution stirred at room temperature for 2 hours before being filtered. The white salt collected was washed thoroughly with dichloromethane and air-dried. The salt was suspended in diethyl ether (70 ml) and stirred with an aqueous solution of saturated sodium hydroxide until the dissolution of the solid. The aqueous phase was extracted with diethyl ether (2×70 ml) and the combined organic phases dried over magnesium sulfate, filtered and concentrated under reduced pressure to give 2a as an orange solid (8.97 g, 86%).

Example 4

Preparation of 4,4'-methylenebis(2,6-diisopropylaniline) (2b)

To a solution of 2,6-diisopropylaniline (5.00 g, 0.028 mol) and formaldehyde (1.38 g, 0.018 mol, 0.65 eq.) was added dilute hydrochloric acid (2.2 ml, 0.1 M). The biphasic solution was stirred at 110° C. overnight. The dark reddish solution was allowed to cool to ambient temperature and diluted with dichloromethane (15 ml). The minimum amount of concentrated hydrochloric acid (2 ml) was added and the solution stirred at room temperature for 2 hours before being filtered. The white salt collected was washed thoroughly with dichloromethane and air-dried. The salt was suspended in diethyl ether (70 ml) and stirred with an aqueous solution of saturated sodium hydroxide until the complete dissolution of the solid. The aqueous phase was extracted with diethyl ether (2×70 ml), the combined organic phases dried over magnesium sulfate and concentrated under reduced pressure to give 2b as a purple oil (2.10 g, 40%).

Compound 2b: ES mass spectrum, m/z 367 [M+H]$^+$; IR (cm$^{-1}$), 3475, 3384 (N—H); $^1$H NMR (CDCl$_3$), δ 1.14 (d, 24H, $^3$J(HH) 6.7, CH(CH$_3$)), 2.82 (sept, 4H, CH(CH$_3$)), 3.46 (br, 4H, NH$_2$), 3.76 (s, 2H, CH$_2$), 6.77 (s, 4H, Ar—H). $^{13}$C NMR (CDCl$_3$, $^1$H gated decoupled), δ 21.5 (s, CH$_3$), 26.9 (s, CH), 40.2 (s, CH$_2$), 122.2 (s, Ar), 130.5 (s, Ar), 131.5 (s, Ar), 136.9 (s, Ar).

Example 5

Preparation of αα-bis(4-amino-3,5-dimethylphenyl)toluene (3a)

A modification of the preparation described in C. A. Hunter, J. Am. Chem. Soc., 1992, 114, 5303, was employed. To a solution of 2,6-dimethylaniline (5.00 g, 0.041 mol) and benzaldehyde (5.65 g, 0.053 mol, 1.3 eq.) was added concentrated hydrochloric acid (5 ml). After stirring for one night at 140° C., the dark green solution was allowed to cool to ambient temperature and diluted with dichloromethane (15 ml). The minimum amount of concentrated hydrochloric acid (2 ml) was introduced and the solution stirred at ambient temperature for 2 hours before being filtered. The yellow salt collected was washed thoroughly with dichloromethane and air dried. The salt was suspended in diethyl ether (70 ml) and stirred with an aqueous solution of saturated sodium hydroxide until the complete dissolution of the solid. The aqueous phase was extracted with diethyl ether (2×70 ml) and the combined organic phases were dried over magnesium sulfate and concentrated under reduced pressure to give 3a as a purple oil (4.11 g, 59%).

Example 6

Preparation of αα-bis(4-amino-3,5-diisopropylphenyl)toluene (3b)

To a solution of 2,6-diisopropylaniline (5.00 g, 0.028 mol) and benzaldehyde (3.82 g, 0.036 mol, 1.3 eq.) was added concentrated hydrochloric acid (5 ml). The biphasic solution was stirred at 140° C. overnight. The resulting dark green solution was allowed to cool to ambient temperature and diluted with dichloromethane (15 ml). The minimum amount of concentrated hydrochloric acid (2 ml) was added and the solution stirred at ambient temperature for 2 hours before being filtered. The yellow salt collected was washed thoroughly with dichloromethane and air dried. The salt was suspended in diethyl ether (70 ml) and stirred with an aqueous solution of saturated sodium hydroxide until the complete dissolution of the solid. The aqueous phase was extracted with diethyl ether (2×70 ml), the combined organic phases dried over magnesium sulfate and concentrated under reduced pressure to give 3b as a pale blue solid (1.52 g, 24%).

Compound 3b: ES mass spectrum, m/z 443 [M+H]$^+$; IR (cm$^{-1}$) 3474, 3442, 3371 (N—H); $^1$H NMR (CDCl$_3$): δ 1.10 (d, 24H, $^3$J(HH) 6.7, CH(C$\underline{H}_3$)), 2.81 (sept, 4H, C$\underline{H}$(CH$_3$)), 3.54 (br, 4H, NH$_2$), 5.20 (s, 1H, C$\underline{H}$Ph), 6.76 (s, 4H, Ar—H), 7.0-7.2 (m, 5H, Ar—H); $^{13}$C NMR (CDCl$_3$, $^1$H gated decoupled), δ 23.0 (s, CH$_3$), 28.4 (s, CH), 57.0 (s, CH), 124.4 (s, Ar), 125.9 (s, Ar), 128.3 (s, Ar), 129.7 (s, Ar), 132.7 (s, Ar), 135.0 (s, Ar), 138.3 (s, Ar), 146.7 (s, Ar).

Example 7

Preparation of αα-bis(4-amino-3,5-diisopropylphenyl)-4-bromotoluene (4)

To a solution of 2,6-diisopropylaniline (5.00 g, 28.7 mmol) and p-bromobenzaldehyde (3.38 g, 18.3 mmol, 0.65 eq.) was added concentrated hydrochloric acid (1 ml). The biphasic solution was stirred at 120° C. overnight. The resulting dark blue solution was allowed to cool to ambient temperature and diluted with chloroform. The minimum amount of concentrated hydrochloric acid was added and the solution stirred at ambient temperature for 2 hours before being filtered. The yellow salt collected was washed thoroughly with chloroform and air dried. The salt was suspended in chloroform (25 ml) and stirred with an aqueous solution of saturated sodium hydroxide until the complete dissolution of the solid. The aqueous phase was extracted with chloroform (2×70 ml), the combined organic phases dried over magnesium sulfate and concentrated under reduced pressure to give 4 as a pale blue solid (1.32 g, 45%).

Compound 4: ES mass spectrum, m/z 522 [M+H]$^+$; IR (cm$^{-1}$) 3392 (N—H); $^1$H NMR (CDCl$_3$): δ1.10 (d, 24H, $^3$J(HH) 6.7, CH(C$\underline{H}_3$)$_2$), 2.82 (sept, 4H, CH(C$\underline{H}_3$)$_2$), 3.56 (br, 4H, NH$_2$), 5.20 (s, 1H, CHPh), 6.68 (s, 4H, Ar—H), 6.92 (d, 2H, $^3$J(HH) 8.3, Ar—H), 7.27 (d, 2H, Ar—H); $^{13}$C NMR (CDCl$_3$, $^1$H gated decoupled), δ22.5 (s, CH$_3$), 22.5 (s, CH$_3$), 28.0 (s, CH), 56.0 (s, CH$_3$), 119.3 (s, Ar), 123.8 (s, Ar), 130.9 (s, Ar), 131.1 (s, Ar), 132.3 (s, Ar), 133.8 (s, Ar), 138.1 (s, Ar), 145.5 (s, Ar); Anal. (C$_{31}$H$_{41}$N$_2$Br) calcd: C, 71.38; H, 7.94; N, 5.37. Found: C, 71.37; H, 8.04; N, 5.21%. In addition, a single crystal X-ray diffraction study of 4 has confirmed the structural type.

Example 8

Preparation of αα-bis(4-amino-3,5-diisopropylphenyl)-4-hydroxytoluene (5)

To a solution of 2,6-diisopropylaniline (5.00 g, 28.7 mmol) and p-hydroxybenzaldehyde (2.24 g, 18.3 mmol, 0.65 eq.) was added concentrated hydrochloric acid (1 ml). The biphasic solution was stirred at 120° C. overnight. The resulting dark blue solution was allowed to cool to ambient temperature and diluted with chloroform. The minimum amount of concentrated hydrochloric acid was added and the solution stirred at ambient temperature for 2 hours before being filtered. The whitish salt collected was washed thoroughly with chloroform and air dried. The salt was suspended in chloroform (25 ml) and stirred with an aqueous solution of saturated sodium hydroxide until the complete dissolution of the solid. The aqueous phase was extracted with chloroform (2×70 ml), the combined organic phases dried over magnesium sulfate and concentrated under reduced pressure to give 5 as a red solid (1.11 g, 17%).

Compound 5: ES mass spectrum, m/z 459 [M+H]$^+$; IR (cm$^{-1}$) 3417, 3327 (N—H, O—H); $^1$H NMR (CDCl$_3$): δ1.10 (d, 24H, $^3$J(HH) 6.7, CH(C$\underline{H}_3$)$_2$), 2.82 (sept, 4H, C$\underline{H}$(CH$_3$)), 3.56 (br, 4H, NH$_2$), 5.19 (s, 1H, CHPh), 6.69 (s, 4H, Ar—H), 6.92 (d, 2H, $^3$J(HH) 8.2, Ar—H), 7.27 (d, 2H, $^3$J(HH) 8.2, Ar—H); $^{13}$C NMR (CDCl$_3$, $^1$H gated decoupled) δ22.5 (s, CH$_3$), 22.6 (s, CH$_3$), 28.0 (s, CH), 55.6 (s, CH$_3$), 114.4 (s, Ar), 124.0 (s, Ar), 130.2 (s, Ar), 132.7 (s, Ar), 135.4 (s, Ar), 137.3 (s, Ar), 138.1 (s, Ar), 153.6 (s, Ar). In addition, a single crystal X-ray diffraction study of 5 has confirmed the structural type.

Example 9

Preparation of αα-bis(4-amino-3,5-diisopropylphenyl)-4-nitrotoluene (6)

To a solution of 2,6-diisopropylaniline (5.00 g, 28.3 mmol) and p-nitrobenzaldehyde (2.77 g, 18.4 mmol, 0.65 eq.) was added concentrated hydrochloric acid (5 ml). The biphasic solution was stirred at 120° C. overnight. The resulting dark green solution was allowed to cool to ambient temperature and diluted with dichloromethane. The minimum amount of concentrated hydrochloric acid was added and the solution stirred at ambient temperature for 2 hours before being filtered. The yellow salt collected was washed thoroughly with dichloromethane and air dried. The salt was suspended in diethyl ether (70 ml) and stirred with an aqueous solution of saturated sodium hydroxide until the complete dissolution of the solid. The aqueous phase was extracted with diethyl ether (2×70 ml), the combined organic phases dried over magnesium sulfate and concentrated under reduced pressure to give 6 as a yellow solid (1.01 g, 10%).

Compound 6: ES mass spectrum, m/z 488 [M+H]$^+$; IR (cm$^{-1}$) 3394, 3478 (N—H), 1515, 1345 (NO$_2$); $^1$H NMR (CDCl$_3$): δ1.09 (d, 24H, $^3$J(HH) 6.7, CH(C$\underline{H}_3$)), 2.81 (sept, 4H, C$\underline{H}$(CH$_3$)), 3.56 (br, 4H, NH$_2$), 5.32 (s, 1H, CHPh), 6.67 (s, 4H, Ar—H), 7.21 (dt, 2H, $^3$J(HH) 8.8, 1.9, Ar—H), 8.00 (dt, 2H, $^3$J(HH) 8.8, 1.9, Ar—H); $^{13}$C NMR (CDCl$_3$, $^1$H gated decoupled)δ 23.0 (s, CH$_3$), 28.4 (s, CH), 57.0 (s, CH), 124.4

(s, Ar), 125.9 (s, Ar), 128.3 (s, Ar), 129.7 (s, Ar), 132.7 (s, Ar), 135.0 (s, Ar), 138.3 (s, Ar), 146.7 (s, Ar).

Example 10

Preparation of αα-bis(4-amino-3,5-dimethylphenyl)-4-isopropyltoluene (7a)

To a solution of 2,6-dimethylaniline (2.00 g, 16.5 mmol) and p-isopropylbenzaldehyde (1.59 g, 10.7 mmol, 0.65 eq.) was added concentrated hydrochloric acid (1 ml). The biphasic solution was stirred at 130° C. overnight. The resulting dark blue solution was allowed to cool to ambient temperature and diluted with dichloromethane (15 ml). The minimum amount of concentrated hydrochloric acid (2 ml) was added and the solution stirred at ambient temperature for 2 hours before being filtered. The yellow salt collected was washed thoroughly with dichloromethane and air dried. The salt was suspended in chloroform (25 ml) and stirred with an aqueous solution of saturated sodium hydroxide until the complete dissolution of the solid. The aqueous phase was extracted with chloroform (2×70 ml), the combined organic phases dried over magnesium sulfate and concentrated under reduced pressure to give 7a as a pale blue solid (1.25 g, 31%).

Compound 7a: ES mass spectrum, m/z 373 [M+H]$^+$; $^1$H NMR (CDCl$_3$), δ 1.15 (d, 6H, $^3$J(HH) 6.7, CH(C$\underline{H}_3$)$_2$), 2.03 (s, 12H, CH$_3$), 2.79 (sept, 1H, C$\underline{H}$(CH$_3$)$_2$), 3.45 (br, 2H, NH$_2$) 5.14 (s, 1H, CHPh), 6.62 (s, 4H, Ar—H), 7.03-7.10 (m, 4H); $^{13}$C NMR (CDCl$_3$, $^1$H gated decoupled), 17.8 (s, CH$_3$), 24.0 (s, CH(C$\underline{H}_3$)$_2$), 33.6 (s, $\underline{C}$H(CH$_3$)$_2$), 55.2 (s, CH), 121.6 (s, Ar), 126.0 (s, Ar), 129.1 (s, Ar), 129.2 (s, Ar), 134.6 (s, Ar), 140.5 (s, Ar), 142.7 (s, Ar), 146.0 (s, Ar). Anal. (C$_{26}$H$_{32}$N$_2$) calcd: C, 83.82; H, 8.66; N, 7.52. Found: C, 83.71; H, 8.75; N, 7.37%.

Example 11

Preparation of αα-bis(4-amino-3,5-diisopropylphenyl)-4-isopropyltoluene (7b)

To a solution of 2,6-diisopropylaniline (2.00 g, 11.3 mmol) and p-isopropylbenzaldehyde (1.10 g, 7.34 mmol, 0.65 eq.) was added concentrated hydrochloric acid (1 ml). The biphasic solution was stirred at 130° C. overnight. The resulting dark blue solution was allowed to cool to ambient temperature and diluted with dichloromethane (15 ml). The minimum amount of concentrated hydrochloric acid (2 ml) was added and the solution stirred at ambient temperature for 2 hours before being filtered. The yellow salt collected was washed thoroughly with dichloromethane and air dried. The salt was suspended in chloroform (25 ml) and stirred with an aqueous solution of saturated sodium hydroxide until the complete dissolution of the solid. The aqueous phase was extracted with chloroform (2×70 ml), the combined organic phases dried over magnesium sulfate and concentrated under reduced pressure to give a pale blue solid that afford 7b as a white solid after recrystallisation in hot hexane (1.64 g, 46%).

Compound 7b: ES mass spectrum, m/z 485 [M+H]$^+$; IR (cm$^{-1}$) 3400 (N—H), 1620, 1597 (C=N); $^1$H NMR (CDCl$_3$): δ1.19 (d, 24H, $^3$J(HH) 6.9, CH(C$\underline{H}_3$)$_2$), 1.23 (d, 6H, $^3$J(HH) 7.0, CH(C$\underline{H}_3$)$_2$), 2.91 (sept, 5H, CH(CH$_3$)$_2$), 5.29 (s, 1H, CHPh), 6.82 (s, 4H, Ar—H), 7.03-7.10 (m, 4H, Ar—H); $^{13}$C NMR (CDCl$_3$, $^1$H gated decoupled), δ22.4 (s, CH$_3$), 22.5 (s, CH$_3$), 24.1 (s, CH$_3$), 28.0 (s, $\underline{C}$H(CH$_3$)$_2$), 33.6 (s, $\underline{C}$H(CH$_3$)$_2$), 56.3 (s, $\underline{C}$HPh), 124.0 (s, Ar), 126.0 (s, Ar), 129.1 (s, Ar), 132.2 (s, Ar), 134.8 (s, Ar), 137.9 (s, Ar), 143.6 (s, Ar), 145.9 (s, Ar); Anal. (C$_{32}$H$_{52}$N$_2$) calcd: C, 84.24; H, 9.98; N, 5.78. Found C, 84.36, H, 10.12; N, 5.83%. In addition, a single crystal X-ray diffraction study of 7b has confirmed the structural type.

Example 12

Preparation of 4,4'-methylene(2,6-diisopropylaniline)(2,6-dimethylaniline)methane (8)

To a solution of 2,6-dimethylaniline (2.50 g, 0.021 mol), 2,6-diisopropylaniline (3.65 g, 0.021 mol, 1 eq.) and formaldehyde (1.00 g, 0.014 mol, 0.65 eq.) was added concentrated hydrochloric acid (5 ml). The biphasic solution was stirred at 110° C. overnight. The resulting dark blue solution was allowed to cool to ambient temperature and diluted with dichloromethane (15 ml). The minimum amount of concentrated hydrochloric acid (2 ml) was added and the solution stirred at ambient temperature for 2 hours before being filtered. The white salt collected was washed thoroughly with dichloromethane and air dried (nb. this step removes the salt of 2a). The remaining salt was suspended in diethyl ether (70 ml) and stirred with an aqueous solution of saturated sodium hydroxide until the complete dissolution of the solid. The aqueous phase was extracted with diethyl ether (2×70 ml), the combined organic phases dried over magnesium sulfate and concentrated under reduced pressure to give a clear oil. Recrytallisation of the residue from the minimum amount of hot hexane afforded 8 as a white crystalline solid (0.34 g, 5%).

Compound 8: ES mass spectrum, m/z 311 [M+H]$^+$; IR (cm$^{-1}$), 3410 (N—H); $^1$H NMR (CDCl$_3$), δ 1.17 (d, 12H, $^3$J(HH) 7.8, CH(C$\underline{H}_3$)$_2$), 2.07 (s, 6H, C$\underline{H}_3$), 2.84 (sept, 2H, C$\underline{H}$(CH$_3$)$_2$), 3.47 (br, 4H, NH$_2$), 3.69 (s, 2H, CH$_2$), 6.70 (s, 2H, Ar—H), 6.79 (s, 2H, Ar—H); $^{13}$C NMR (CDCl$_3$, $^1$H gated decoupled), δ18.1 (s, CH$_3$), 22.9 (s, CH$_3$), 28.4 (s, CH), 41.3 (s, CH$_2$), 122.3 (s, Ar), 123.8 (s, Ar), 129.0 (s, Ar), 132.1 (s, Ar), 133.0 (s, Ar), 138.4 (s, Ar), 140.7 (s, Ar). In addition, a single crystal X-ray diffraction study of 8 has confirmed the structural type.

Example 13

Preparation of αα-(4-amino-3,5-dimethylphenyl)(4-amino-3,5-diisopropylphenyl)toluene (9)

To a solution of 2,6-diisopropylaniline (2.50 g, 0.014 mol), 2,6-dimethylaniline (1.70 g, 0.014 mol, 1 eq.) and benzaldehyde (1.93 g, 0.018 mol, 1.3 eq.) was added concentrated hydrochloric acid (5 ml). The biphasic solution was stirred at 140° C. overnight. The resulting dark green solution was allowed to cool to ambient temperature and diluted with dichloromethane (15 ml). The minimum amount of concentrated hydrochloric acid (2 ml) of concentrated hydrochloric acid was added and the solution stirred at ambient temperature for 2 hours before being filtered. The yellow salt collected was washed thoroughly with dichloromethane and air dried. The salt was suspended in diethyl ether (70 ml) and stirred with an aqueous solution of saturated sodium hydroxide until the complete dissolution of the solid. The aqueous phase was extracted with diethyl ether (2×70 ml), the combined organic phases dried over magnesium sulfate and concentrated under reduced pressure to give a pale blue solid. Recrystallisation of the solid from hexane gave 9 in low yield as a white solid (0.22 g, 4%).

Compound 9: ES mass spectrum, m/z 387 [M+H]$^+$. $^1$H NMR (CDCl$_3$): δ1.19 (d, 12H, $^3$J(HH) 6.9, CH(C$\underline{H}_3$)$_2$), 2.05 (2, 6H, Ar-Me), 2.91 (sept, 2H, C$\underline{H}$(CH$_3$)$_2$), 5.29 (s, 1H, CHPh), 6.71 (s, 2H, Ar—H), 6.82 (s, 2H, Ar—H), 7.0-7.3 (m, 4H, Ar—H).

Example 14

Preparation of 4,4'-methylene(2,6-diisopropylaniline)(2-methylaniline)methane (10)

To a solution of 2-methylaniline (2.78 g, 0.023 mol), 2,6-diisopropylaniline (4.14 g, 0.023 mol, 1 eq.) and formaldehyde (2.24 g, 0.030 mol, 1.3 eq.) was added concentrated hydrochloric acid (5 ml). The biphasic solution was stirred at 130° C. for 8 hours. The resulting orange solution was allowed to cool to ambient temperature and diluted with dichloromethane (15 ml). The minimum amount of concentrated hydrochloric acid (2 ml) was added and the solution stirred at ambient temperature overnight before being filtered. The pale yellow white salt collected was washed thoroughly with dichloromethane and air dried. The salt was suspended in diethyl ether (70 ml) and stirred with an aqueous solution of saturated sodium hydroxide until the complete dissolution of the solid. The aqueous phase was extracted with diethyl ether (2×70 ml) to give a brown residue. Recrystallisation of the residue from hot hexane gave 10 as a pale brown solid (0.48 g, 7%).

Compound 10: ES mass spectrum, m/z 297 [M+H]$^+$; $^1$H NMR (CDCl$_3$): δ 1.19 (d, 12H, $^3$J(HH) 7.8, CH(C$\underline{H}_3$)$_2$), 2.05 (s, 3H, C$\underline{H}_3$), 2.84 (sept, 2H, CH(CH$_3$)$_2$), 3.54 (br, 4H, NH$_2$), 3.71 (s, 2H, CH$_2$), 6.5-6.6 (d, 1H, Ar—H), 6.7-6.8 (m, 4H, Ar—H); $^{13}$C NMR (CDCl$_3$, $^1$H gated decoupled), δ18.1 (s, CH$_3$), 23.0 (s, CH$_3$), 28.4 (s, CH), 41.3 (s, CH$_2$), 115.5 (s, Ar), 122.8 (s, Ar), 127.6 (s, Ar), 129.4 (s, Ar), 131.2 (s, Ar), 138.5 (s, Ar), 142.8 (s, Ar).

Formulae for Examples 1-14

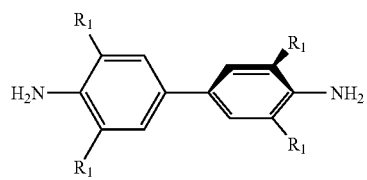

Example 1 (1a) R$_1$ = Me
Example 2 (1b) R$_1$ = i-Pr

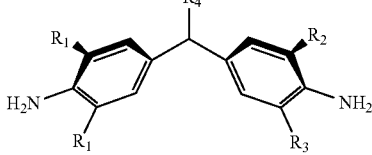

Example 3 (2a) R$_1$ = R$_2$ = R$_3$ = Me, R$_4$ = H
Example 4 (2b) R$_1$ = R$_2$ = R$_3$ = i-Pr, R$_4$ = H
Example 5 (3a) R$_1$ = R$_2$ = R$_3$ = Me, R$_4$ = Ph
Example 6 (3b) R$_1$ = R$_2$ = R$_3$ = i-Pr, R$_4$ = Ph
Example 7 (4) R$_1$ = R$_2$ = R$_3$ = i-Pr, R$_4$ = Ph-4-Br
Example 8 (5) R$_1$ = R$_2$ = R$_3$ = i-Pr, R$_4$ = Ph-4-OH
Example 9 (6) R$_1$ = R$_2$ = R$_3$ = i-Pr, R$_4$ = Ph-4-NO$_2$
Example 10 (7a) R$_1$ = R$_2$ = R$_3$ = Me, R$_4$ = Ph-4-i-Pr
Example 11 (7b) R$_1$ = R$_2$ = R$_3$ = i-Pr, R$_4$ = Ph-4-i-Pr
Example 12 (8) R$_1$ = Me, R$_2$ = R$_3$ = i-Pr, R$_4$ = H
Example 13 (9) R$_1$ = Me, R$_2$ = R$_3$ = i-Pr, R$_4$ = Ph
Example 14 (10) R$_1$ = i-Pr, R$_2$ = Me, R$_3$ = R$_4$ = H Where Ph-4-Br=4-bromotoluene, Ph-4-OH=4-hydroxytoluene, Ph-4-NO$_2$=4-nitrotoluene, and Ph-4-i-Pr=4-isopropyltoluene.

Preparation of Ligands

The electrospray (ES) mass spectra were recorded using a micromass Quattra LC mass spectrometer with dichloromethane or methanol as the matrix [Masslynx software. open-access autosampler injection]. The infrared spectra were recorded with Universal ATR sampling accessories on a Perkin Elmer Spectrum One FTIR instrument. $^1$H and $^{13}$C NMR spectra were recorded on a Bruker ARX spectrometer 250/300 MHz at ambient temperature; chemical shifts (ppm) are referred to the residual protic solvent peaks. The reagents 2-pyridinecarboxaldehyde, the 2-acetylpyridine, 2,3,5,6-tetramethyl-benzene-1,4-diamine were purchased from Aldrich Chemical Co. and used without further purification. Formic acid (98%) was purchased from Fisons PLC and used without further purification. The compounds 2,2'-bipyridinyl-6-carbaldehyde [J. Uenishi, T. Tanaka, K. Nishiwaki, S. Wakabayashi, S. Oae and H. Tsukube, *J. Org. Chem.*, 1993, 58, 4382], 6-acetyl-2,2'-bipyridine [J. Uenishi, T. Hiraoka, S. Hata, K. Nishiwaki and O. Yonemitsu, *J. Org. Chem.*, 1998, 63, 2481] were prepared according to the indicated journal articles. All other chemicals were obtained commercially and used without further purification.

Example 15

Preparation of 2,3,5,6-tetramethyl-N,N-bis-(pyridin-2-ylmethylene)-benzene-1,4-diamine (11a)

To a solution of 2,3,5,6-tetramethyl-benzene-1,4-diamine (1.50 g, 9.15 mmol) in absolute ethanol (100 ml) was added 2-pyridinecarboxaldehyde (1.90 ml, 0.02 mmol, 2.2 eq.) dropwise. After stirring overnight at 70° C., the suspension was filtered, washed with cold ethanol and dried under reduced pressure to give 11a in good yield as a pale yellow solid (1.82 g, 90%).

Compound 11a: ES mass spectrum, m/z 343 [M+H]$^+$; IR (cm$^{-1}$) 1641, 1585, 1562 (C=N); $^1$H NMR (CDCl$_3$), δ 2.11 (s, 12H, Ar—CH$_3$), 7.2-7.3 (m, 2H, Py-H), 7.8-7.9 (m, 2H, Py-H), 7.72 (m, 2H, Py-H), 8.3-8.4 (m, 4H, Py-H, HC=N); $^{13}$C NMR (CDCl$_3$, $^1$H gated decoupled), δ15.0 (s, CH$_3$), 121.2 (s, Ar), 123.5 (s, Ar), 125.2 (s, Ar), 136.7 (s, Ar), 147.2 (s, Ar), 149.6 (s, Ar), 154.6 (s, Ar), 163.8 (s, C=N).

Example 16

Preparation of 2,3,5,6-tetramethyl-N,N-bis-(pyridin-2-ylethylidene)-benzene-1,4-diamine (11b)

To a mixture of 2,3,5,6-tetramethyl-benzene-1,4-diamine (0.50 g, 3.05 mmol) and 2-acetylpyridine (0.75 ml, 6.71 mmol, 2.2 eq.) in absolute ethanol (50 ml) was added three drops of formic acid. The solution was heated to 90° C. and stirred overnight. The suspension was filtered, the residue washed with cold ethanol and dried under reduced pressure to give 11b in low yield as a yellow solid (0.11 g, 10%).

Compound 11b: ES mass spectrum, m/z 371 [M+H]$^+$; IR (cm$^{-1}$) 1631, 1595, 1567 (C=N); $^1$H NMR (CDCl$_3$), δ 1.99 (s, 12H, Ar—CH$_3$), 2.19 (s, 6H, (CH$_3$)C=N), 7.2-7.3 (m, 2H, Py-H), 7.8-7.9 (m, 2H, Py-H), 8.3-8.4 (m, 2H, Py-H), 8.6-8.7 (m, 2H, Py-H); $^{13}$C NMR (CDCl$_3$, $^1$H gated decoupled), δ14.8 (s, Ar—CH$_3$), 17.0 (s, CH$_3$), 121.6 (s, Ar), 125.1 (s, Ar), 136.8 (s, Ar), 144.8 (s, Ar), 149.0 (s, Ar), 157.2 (s, Ar), 168.3

(s, C≡N). In addition, a single crystal X-ray diffraction study of 11b has confirmed the structural type.

Example 17

Preparation of 2,3,5,6-tetramethyl-N-(pyridin-2-ylethylidene)-N-(pyridin-2-ylmethylene)-benzene-1,4-diamine (11c)

Compound 6c was made in two steps (1 and 2) as outlined below:

Step 1: To a mixture of 2-acetylpyridine (0.30 ml, 0.26 mmol) and 2,3,5,6-tetramethyl-benzene-1,4-diamine (0.60 g, 0.37 mmol, 1.4 eq.) in toluene (2 ml) was added 2 drops of formic acid. The suspension was heated for three days at 50° C. The dark reddish suspension was cooled, filtered and the residue washed with cold toluene. The filtrate was evaporated, dissolved in chloroform (2 ml) and cooled to −78° C. for 0.5 hours before being filtered. Hexane was added to the filtrate and all volatiles were removed under reduced pressure to give 2,3,5,6-tetramethyl-N-(1-pyridin-2-ylethylidene)-benzene-1,4-diamine as a brown solid (0.31 g, 45%).

Compound 2,3,5,6-tetramethyl-N-(pyridin-2-ylethylidene)-benzene-1,4-diamine: ES mass spectrum, m/z 268 [M+H]$^+$; IR (cm$^{-1}$) 3378 (N—H), 1632 (C═N); $^1$H NMR (CDCl$_3$), δ1.99 (s, 6H, Ar—CH$_3$), 2.11 (s, 3H, (CH$_3$)C═N), 2.13 (s, 6H, Ar—CH$_3$), 3.40 (s, br, 2H, NH$_2$), 7.40 (m, 1H, Py-H), 7.80 (m, 1H, Py-H), 8.41 (m, 1H, Py-H), 8.71 (m, 1H, Py-H); $^{13}$C NMR (CDCl$_3$, $^1$H gated decoupled), δ14.0 (s, Ar—CH$_3$), 15.0 (s, Ar—CH$_3$), 17.0 (s, (CH$_3$)C═N), 119.2 (s, Ar), 121.6 (s, Ar), 122.0 (s, Ar), 125.0 (s, Ar), 136.8 (s, Ar), 138.7 (s, Ar), 141.4 (s, Ar), 148.9 (s, Ar), 157.3 (s, Ar), 168.1 (s, C═N).

Step 2: To a solution of 2,3,5,6-tetramethyl-N-(pyridin-2-ylethylidene)-benzene-1,4-diamine (0.25 g, 0.94 mmol) in absolute ethanol (6 ml) was added 2-pyridinecarboxaldehyde (0.10 ml, 1.00 mmol, 1.1 eq) in ethanol (4 ml). One drop of formic acid was added after thirty minutes of stirring at room temperature. The solution was allowed to stir at room temperature overnight. On cooling to −78° C., the suspension was filtered, washed with cold ethanol and dried under reduced pressure to give 11c as a pale yellow powder (0.17 g, 51%).

Compound 11c: ES mass spectrum, m/z 357 [M+H]$^+$; IR (cm$^{-1}$) 1636, 1585, 1565 (C═N); $^1$H NMR (CDCl$_3$), δ1.90 (s, 6H, Ar—CH$_3$), 2.03 (s, 6H, Ar—CH$_3$), 2.11 (s, 3H, (CH$_3$) C═N), 7.2-7.4 (m, 2H, Py-H), 7.7-7.8 (m, 2H, Py-H), 8.2-8.4 (m, 2H, CH═N), 8.30 (m, 1H, Py-H), 8.6-8.7 (m, 2H, Py-H); $^{13}$C NMR (CDCl$_3$, $^1$H gated decoupled), δ13.4 (s, Ar—CH$_3$), 14.0 (s, Ar—CH$_3$), 15.7 (s, (CH$_3$)C═N), 120.1 (s, Ar), 120.2 (s, Ar), 120.8 (s, Ar), 122.3 (s, Ar), 123.7 (s, Ar), 124.1 (s, Ar), 135.4 (s, Ar), 135.7 (s, Ar), 144.1 (s, Ar), 145.3 (s, Ar), 147.5 (s, Ar), 148.6 (s, Ar), 153.7 (s, Ar), 155.5 (s, Ar), 162.7 (s, (CH$_3$)C═N), 166.6 (s, C═N).

Example 18

Preparation of 2,3,56-tetramethyl-N,N-bis-{(6-pyridin-2-yl)pyridin-2-ylmethylene}-benzene-1,4-diamine (12a)

To a suspension of 2,2'-bipyridinyl-6-carbaldehyde (0.39 g, 2.10 mmol) in diethyl ether (5 ml) was added 2,3,5,6-tetramethyl-benzene-1,4-diamine (0.086 g, 0.52 mmol, 0.25 eq.) and one drop of formic acid. The orange solution was heated to reflux for 48 hours. On cooling to 0° C., the suspension was filtered, washed with cold ethanol and dried under reduced pressure to give 12a as a yellow solid (0.08 g, 31%).

Compound 12a: ES mass spectrum, m/z 497 [M+H]$^+$; $^1$H NMR (CDCl$_3$), δ 2.08 (s, 12H, Ar—CH$_3$), 7.26 (qd, 2H, $^3$J(HH) 6.1, $^4$J(HH) 1.1, Py-H), 7.76 (td, 2H, $^3$J(H—H) 7.8, $^4$J(HH) 1.6, Py-H), 7.90 (t, 2H, $^3$J(HH) 7.9, Py-H), 8.29 (dd, 2H, $^3$J(HH) 7.8, $^4$J(HH) 0.9, Py-H), 8.34 (s, 2H, HC═N), 8.43 (d, 2H, $^3$J(HH) 7.8, Py-H), 8.45 (dd, 2H, $^3$J(HH) 7.8, $^4$J(HH) 0.9, Py-H), 8.64 (d, 2H, $^3$J(HH) 3.9, Py-H); $^{13}$C NMR (CDCl$_3$, 1H gated decoupled), δ 14.1 (s, Ar—CH$_3$), 119.9 (s, Ar), 120.2 (s, Ar), 121.5 (s, Ar), 122.4 (s, Ar), 122.9 (s, Ar), 136.0 (s, Ar), 136.6 (s, Ar), 146.4 (s, Ar), 148.3 (s, Ar), 153.2 (s, Ar), 154.7 (s, Ar), 155.0 (s, Ar), 163.3 (s, C═N).

Example 19

Preparation of 2,3,5,6-tetramethyl-N,N-bis-{(6-pyridin-2-yl)pyridin-2-ylethylidene}-benzene-1,4-diamine (12b)

To a suspension of 6-acetyl-2,2'-bipyridine (0.39 g, 1.95 mmol) in absolute ethanol (5 ml) was added 2,3,5,6-tetramethyl-benzene-1,4-diamine (0.16 g, 0.97 mmol, 0.5 eq.) and one drop of formic acid. The brown solution was refluxed for 24 hours. On cooling to 0° C. the suspension was filtered, washed with cold ethanol and dried under reduced pressure to afford 12b as a pale yellow solid (0.098 g, 10%).

Compound 12b: ES mass spectrum, m/z 525 [M+H]$^+$; IR (cm$^{-1}$) 1645, 1578, 1561 (C═N); $^1$H NMR (CDCl$_3$), δ 1.96 (s, 12H, Ar—CH$_3$), 2.26 (s, 6H, (CH$_3$)C═N), 7.29 (qd, 2H, $^3$J(HH) 5.6, $^4$J(HH) 1.2, Py-1H), 7.81 (td, 2H, $^3$J(HH) 7.8, $^4$J(HH) 1.6, Py-H), 7.90 (t, 2H, $^3$J(HH) 7.8, Py-H), 8.43 (d, 2H, $^3$J(HH) 7.4, Py-H), 8.50 (d, 2H, $^3$J(HH) 7.8, Py-H), 8.53 (d, 2H, $^3$J(HH) 7.8, Py-H), 8.65 (d, 2H, $^3$J(HH) 4.8, Py-H); $^{13}$C NMR (CDCl$_3$, $^1$H gated decoupled), δ 14.8 (s, CH$_3$), 16.9 (s, CH$_3$), 121.4 (s, Ar), 121.5 (s, Ar), 122.3 (s, Ar), 124.2 (s, Ar), 137.3 (s, Ar), 137.8 (s, Ar), 145.0 (s, Ar), 149.6 (s, Ar), 155.3 (s, Ar), 156.3 (s, Ar), 156.5 (s, Ar), 167.8 (s, Ar), 168.6 (s, C═N).

Example 20

Preparation of 3,5,3',5'-tetramethyl-N,N-bis-(pyridin-2-ylmethylene)-biphenyl-4,4'-diamine (13a)

To a suspension of 1a (0.48 g, 2.00 mmol) in absolute ethanol (10 ml) was added 2-pyridinecarboxaldehyde (0.67 ml, 7.00 mmol, 3.5 eq.). The mixture was stirred and heated to reflux overnight. On cooling to room temperature, the suspension was filtered, washed with cold ethanol and dried under reduced pressure to give 13a in good yield as a yellow solid (0.51 g, 62%).

Compound 13a: ES mass spectrum, m/z 419 [M+H]$^+$; IR (cm$^{-1}$) 1648, 1584, 1566 (C═N); $^1$H NMR (CDCl$_3$), δ 2.20 (s, 12H, (Ar—CH$_3$)), 7.25 (s, 4H, Ar—H), 7.3-7.4 (m, 2H, Py-H), 7.7-7.9 (m, 2H, Py-H), 8.2-8.4 (m, 2H, Py-H), 8.35 (s, 2H, CH═N), 8.7-8.8 (m, 2H, Py-H); $^{13}$C NMR (CDCl$_3$, $^1$H gated decoupled), δ18.9 (s, Me), 121.7 (s, Ar), 125.8 (s, Ar), 127.1 (s, Ar), 127.8 (s, Ar), 137.2 (s, Ar), 137.3 (s, Ar), 149.7 (s, Ar), 150.1 (s, Ar), 157.3 (s, Ar), 164.0 (s, C═N). Anal. (C$_{28}$H$_{26}$N$_4$) calcd: C, 80.34; H, 6.27; N, 13.38. Found: C, 80.15; H, 6.35; N, 13.32%. In addition, a single crystal X-ray diffraction study of 13a has confirmed the structural type.

Example 21

Preparation 3,5,3',5'-tetramethyl-N,N-bis-(pyridin-2-ylethylidene)-biphenyl-4,4'-diamine (13b)

To a suspension of 1a (0.50 g, 2.10 mmol) in absolute ethanol (10 ml) was added 2-acetylpyridine (0.80 ml, 7.10 mmol, 3.4 eq.) and two drops of formic acid. The suspension was heated to reflux overnight. On cooling to room temperature the suspension was filtered, washed with cold ethanol and dried under reduced pressure to give 13b as a yellow solid (0.51 g, 41%).

Compound 13b: ES mass spectrum, nm/z 447 [M+H]$^+$; $^1$H NMR (CDCl$_3$), □ 2.04 (s, 12H, Ar—CH$_3$), 2.19 (s, 6H, (CH$_3$)C=N), 7.26 (s, 4H, Ar—H), 7.3-7.4 (m, 2H, Py-H), 7.7-7.8 (m, 2H, Py-H), 8.3-8.4 (m, 2H, Py-H), 8.6-8.7 (m, 2H, Py-H); $^{13}$C NMR (CDCl$_3$, $^1$H gated decoupled), δ17.2 (s, Ar—CH$_3$), 18.5 (s, (CH$_3$)C=N), 121.8 (s, Ar), 125.3 (s, Ar), 126.2 (s, Ar), 126.8 (s, Ar), 136.4 (s, Ar), 136.9 (s, Ar), 148.0 (s, Ar), 149.0 (s, Ar), 156.9 (s, Ar), 167.9 (s, C=N).

Example 22

Preparation of 3,5,3',5'-tetraisopropyl-N,N,-bis-(pyridin-2-ylmethylene)-biphenyl-4,4'-diamine (14a)

To a suspension of 1b (0.15 g, 0.43 mmol) in absolute ethanol (10 ml) was added 2-pyridinecarboxaldehyde (0.14 ml, 1.40 mmol, 3.3 eq.). The mixture was stirred and heated to 50° C. overnight. On cooling to room temperature the suspension was filtered, washed with cold ethanol and dried under reduced pressure to give 14a as a yellow solid (0.10 g, 43%).

Compound 14a: ES mass spectrum, m/z 531 [M+H]$^+$; $^1$H NMR (CDCl$_3$), 1.1-1.2 (d, 12H, $^3$J(HH) 6.8, CH(C$\underline{H}_3$)$_2$), 2.9-3.0 (sept, 4H, C$\underline{H}$(CH$_3$)$_2$), 7.24 (s, 4H, Ar—H), 7.2-7.3 (m, 2H, Py-H), 7.6-7.9 (m, 2H, Py-H), 8.1-8.3 (m, 2H, Py-H), 8.37 (s, 2H, HC=N), 8.6-8.8 (m, 2H, Py-H); $^{13}$C NMR (CDCl$_3$, $^1$H gated decoupled), δ 23.9 (s, CH$_3$), 28.6 (s, CH), 121.9 (s, Ar), 122.5 (s, Ar), 137.4 (s, Ar), 138.0 (s, Ar), 138.6 (s, Ar), 147.9 (s, Ar), 149.9 (s, Ar), 154.7 (s, Ar), 163.2 (s, C=N).

Example 23

Preparation of 3,5,3',5'-tetraisopropyl-N,N,-bis-(pyridin-2-ylethylidene)-biphenyl-4,4'-diamine (14b)

A mixture of 1b (0.21 g, 0.60 mmol), 2-acetylpyridine (3.0 ml, 26.85 mmol, 45 eq.) and one drop of formic acid was heated to 150° C. for 3 hours. The 2-acetylpyridine was distilled off and absolute ethanol introduced to precipitate the product. Following filtration, washing with cold ethanol and drying under reduced pressure, 14b was isolated as a yellow solid (0.28 g, 85%).

Compound 14b: ES mass spectrum, m/z 559 [M+H]$^+$; $^1$H NMR (CDCl$_3$), δ1.19 (d, 12H, $^3$J(HH) 6.9, CH(C$\underline{H}_3$)$_2$), 2.18 (s, 6H, MeC=N), 2.72 (sept, 4H, C$\underline{H}$(CH$_3$)$_2$), 7.25 (s, 4H, Ar—H), 7.2-7.3 (m, 2H, Py-H), 7.7-7.8 (m, 2H, Py-H), 8.2-8.4 (m, 2H, Py-H), 8.37 8.4-8.6 (m, 2H, Py-H); $^{13}$C NMR (CDCl$_3$, $^1$H gated decoupled), δ 16.4 (s, CH$_3$), 21.9 (s, CH$_3$), 22.3 (s, CH$_3$), 27.4 (s, CH), 120.3 (s, Ar), 120.7 (s, Ar), 123.8 (s, Ar), 135.0 (s, Ar), 135.5 (s, Ar), 136.3 (s, Ar), 144.4 (s, Ar), 147.6 (s, Ar), 155.5 (s, Ar), 166.1 (s, C=N).

Example 24

Preparation of 3,5,3',5'-tetramethyl-N,N-bis-{(6-pyridin-2-yl)pyridin-2-ylmethylene)-biphenyl-4,4'-diamine (15)

To a suspension of 2,2'-bipyridinyl-6-carbaldehyde (0.39 g, 2.10 mmol) in diethyl ether (5 ml) was added 1a (0.13 g, 0.53 mmol, 0.25 eq.) and one drop of formic acid. The yellow reaction mixture was heated to reflux for 48 hours. On cooling to room temperature the suspension was filtered, washed with cold diethyl ether and dried under reduced pressure to give 15 as a yellow solid (0.10 g, 34%).

Compound 15: ES mass spectrum, m/z 573 [M+H]$^+$. $^1$H NMR (CDCl$_3$), δ 2.18 (s, 12H, (Ar—CH$_3$)), 7.29 (s, 4H, Ar—H), 7.41 (dd, 2H, $^3$J(HH) 6.7, $^4$J(HH), Py-H), 7.75 (td, 2H, $^3$J(HH) 7.8, $^4$J(HH) 1.8, Py-H), 7.90 (t, 2H, $^3$J(HH) 7.8, Py-H), 8.27 (dd, 2H, $^3$J(HH) 7.8, $^4$J(HH) 1.6, Py-H), 8.40 (s, 2H, HC=N), 8.44 (dd, 2H, $^3$J(HH) 7.5, $^4$J(HH) 1.2, Py-H), 8.46 (dd, 2H, $^3$J(HH) 7.4, $^4$J(HH) 0.9, Py-H), 8.62 (dd, 2H, $^3$J(HH) 4.3, $^4$J(HH) 0.7, Py-H).

Example 25

Preparation of 3,5,3',5'-tetraisopropyl-N,N-bis-{(6-pyridin-2-yl)pyridin-2-ylmethylene}-biphenyl-4,4'-diamine (16)

To a mixture of 2,2'-bipyridinyl-6-carbaldehyde (0.39 g, 2.10 mmol) in diethyl ether (5 ml) was added 1b (0.18 g, 0.53 mmol, 0.25 eq.) and one drop of formic acid. The orange solution was heated to reflux for 24 hours. On cooling to 0° C. the suspension was filtered, washed with cold diethyl ether and dried under reduced pressure to give 16 as yellow solid (0.20 g, 51%).

Compound 16: ES mass spectrum, m/z 685 [M+H]$^+$; $^1$H NMR (CDCl$_3$), δ 1.20 (d, 24H, $^3$J(HH) 6.9, CH(C$\underline{H}_3$)), 2.81 (sept, 4H, C$\underline{H}$(CH$_3$)$_2$), 7.17 (s, 4H, Ar—H), 7.41 (dd, 2H, $^3$J(HH) 6.7, $^4$J(HH) 1.6, Py-H), 7.75 (td, 2H, $^3$J(HH) 7.8, $^4$J(HH) 1.8, Py-H), 7.90 (t, 2H, $^3$J(HH) 7.8, Py-H), 8.27 (dd, 2H, $^3$J(HH) 7.8, $^4$J(HH) 1.6, CH), 8.40 (s, 2H, HC=N), 8.44 (dd, 2H, $^3$J(HH) 7.5, 4J(HH) 1.2, Py-H), 8.46 (dd, 2H, $^3$J(HH) 7.4, $^4$J(HH) 0.9, Py-H), 8.62 (dd, 2H, $^3$J(HH) 4.3, $^4$J(HH) 0.7, Py-H); $^{13}$C NMR (CDCl$_3$, $^1$H gated decoupled), δ 22.5 (s, CH$_3$), 27.2 (s, CH), 120.1 (s, Ar), 120.3 (s, Ar), 121.0 (s, Ar), 121.6 (s, Ar), 122.9 (s, Ar), 129.2 (s, Ar), 136.0 (s, Ar), 136.6 (s, Ar), 137.1 (s, Ar), 146.6 (s, Ar), 148.0 (s, Ar), 153.0 (s, Ar), 154.7 (s, Ar), 155.1 (s, Ar), 162.5 (s, C=N).

Example 26

Preparation of bis-{4-(pyridin-2-yl-methylene-amino)-3,5-dimethylphenyl}-methane (17)

To a suspension of 2a (0.50 g, 1.97 mmol) in absolute ethanol (2 ml) was added 2-pyridinecarboxaldehyde (0.56 ml, 5.91 mmol, 3 eq.) and one drop of formic acid. The mixture was stirred at 45° C. overnight. On cooling to room temperature the suspension was filtered, washed with cold ethanol and dried under reduced pressure to afford 17 as a yellow solid (0.28 g, 18%).

Compound 17: ES mass spectrum, m/z 433 [M+H]$^+$; $^1$H NMR (CDCl$_3$), δ 2.12 (s, 12H, CH$_3$), 3.77 (s, 2H, CH$_2$), 6.88 (s, 4H, Ar—H), 7.2-7.4 (m, 2H, Py-H), 7.7-7.8 (m, 2H, Py-H), 8.1-8.3 (m, 4H, Py-H, HC=N), 8.6-8.7 (m, 2H, Py-H); $^{13}$C NMR (CDCl$_3$, $^1$H gated decoupled), δ 18.4 (s, CH$_3$), 40.9 (s, CH$_2$), 121.2 (s, Ar), 125.2 (s, Ar), 127.0 (s, Ar), 128.7 (s, Ar), 136.7 (s, Ar), 137.1 (s, Ar), 148.3 (s, Ar), 149.6 (s, Ar), 154.6 (s, Ar), 163.4 (s, C=N). In addition, a single crystal X-ray diffraction study of 17 has confirmed the structural type.

Example 27

Preparation of bis-{-4-(pyridin-2-yl-methylene-amino)-3,5-diisopropylphenyl}-methane (18a)

To a suspension of 2b (1.60 g, 4.37 mmol) in absolute ethanol (10 ml) was added 2-pyridinecarboxaldehyde (1.24 ml, 13.11 mmol, 3 eq.) and two drops of formic acid. The mixture was stirred at 45° C. overnight. On cooling to room temperature the suspension was filtered, washed with cold ethanol and dried under reduced pressure to afford 18a as a yellow solid (1.68 g, 49%).

Compound 18a: ES mass spectrum, m/z 545 [M+H]$^+$; $^1$H NMR (CDCl$_3$), δ 1.10 (d, 24H, $^3$J(HH) 6.9, CH(C$\underline{H}_3$)$_2$), 2.91 (sept, 4H, C$\underline{H}$(CH$_3$)$_2$), 3.95 (s, 2H, CH$_2$), 6.93 (s, 4H, Ar—H), 7.2-7.4 (m, 2H, Py-H), 7.7-7.9 (m, 2H, Py-H), 8.1-8.3 (m, 4H, Py-H, HC=N), 8.6-8.7 (m, 2H, Py-H); $^{13}$C NMR (CDCl$_3$, $^1$H gated decoupled), 18.1 (s, CH$_3$), 22.4 (s, CH), 39.4 (s, CH$_2$), 122.8 (s, Ar), 125.3 (s, Ar), 126.1 (s, Ar), 135.6 (s, Ar), 136.4 (s, Ar), 142.6 (s, Ar), 147.9 (s, Ar), 157.4 (s, Ar), 167.1 (s, C=N).

Example 28

Preparation of bis-{4-din-2-yl-ethylideneamino)-3,5-diisopropylphenyl}-methane (18b)

To a suspension of 2b (0.50 g, 1.37 mmol) in absolute ethanol (3 ml) was added 2-acetylpyridine (0.44 ml, 4.70 mmol, 3.4 eq.) and one drop of formic acid. After stirring for one night at 90° C. the solution was concentrated to half volume and left to stand at −20° C. for 3 days. The yellow solid was filtered, washed with cold ethanol and dried under reduced pressure to give 18b as a yellow powder (0.23 g, 29%).

Compound 18b: ES mass spectrum, m/z 573 [M+H]$^+$; IR (cm$^{-1}$), 1642, 1584, 1565 (C=N); $^1$H NMR (CDCl$_3$), δ1.08 (d, 24H, $^3$J(HH) 6.9, CH(C$\underline{H}_3$)$_2$), 2.17 (s, 6H, (CH$_3$)C=N), 2.67 (sept, 4H, C$\underline{H}$(CH$_3$)$_2$), 3.94 (s, 2H, CH$_2$), 6.91 (s, 4H, Ar—H), 7.2-7.3 (m, 2H, Py-H), 7.7-7.8 (m, 2H, Py-H), 8.1-8.3 (m, 4H, Py-H), 8.6-8.7 (m, 2H, ArH); $^{13}$C NMR (CDCl$_3$, $^1$H gated decoupled), δ 17.7 (s, CH$_3$), 23.4 (s, CH), 23.7 (s, CH), 28.6 (s, CH$_3$), 41.8 (s, CH$_2$), 121.7 (s, Ar), 124.1 (s, Ar), 125.1 (s, Ar), 136.1 (s, Ar), 136.7 (s, Ar), 144.6 (s, Ar), 148.9 (s, Ar), 157.0 (s, Ar), 167.6 (s, C=N).

Example 29

Preparation of bis-{4-(pyridin-2-yl-methylene-amino)-3,5-diisopropylphenyl}-toluene (19)

To a suspension of 3b (0.40 g, 0.91 mmol) in absolute ethanol (3 ml) was added 2-pyridinecarboxaldehyde (0.34 ml, 3.61 mmol, 4 eq.) and two drops of formic acid. The mixture was stirred at 45° C. overnight. On cooling to room temperature the suspension was filtered, washed with cold ethanol and dried under reduced pressure to afford 19 as a yellow solid (0.46 g, 82%).

Compound 19: ES mass spectrum, m/z 621 [M+H]$^+$; $^1$H NMR (CDCl$_3$), δ 1.03 (d, 24H, $^3$J(HH) 7.5, CH(C$\underline{H}_3$)), 2.82 (sept, 4H, C$\underline{H}$(CH$_3$)$_2$), 5.23 (s, 1H, CH), 6.86 (s, 4H, Ar—H), 7.1-7.2 (m, 5H, Ar—H), 7.33 (t, 2H, $^3$J(HH) 6.8, Py-H), 7.77 (t, 2H, $^3$J(HH) 8.6, Py-H), 8.19 (d, 2H, $^3$J(HH) 8.7, Py-H), 8.26 (s, 2H, HC=N), 8.65 (d, 2H, $^3$J(HH) 5.2, Py-H); $^{13}$C NMR (CDCl$_3$, $^1$H gated decoupled), δ 23.9 (s, CH$_3$), 28.4 (s, CH), 57.6 (s, CH), 121.7 (s, Ar), 124.8 (s, Ar), 125.7 (s, Ar), 126.3 (s, Ar), 128.5 (s, Ar), 129.9 (s, Ar), 137.2 (s, Ar), 137.4 (s, Ar), 140.1 (s, Ar), 147.0 (s, Ar), 148.2 (s, CH), 150.0 (s, Ar), 156.7 (s, Ar), 162.5 (s, C=N); Anal. (C$_{43}$H$_{48}$N$_4$) calcd: C, 83.17; H, 7.80; N, 9.02. Found: C, 83.29; H, 7.96; N, 9.03%. In addition, a single crystal X-ray diffraction study of 19 has confirmed the structural type.

Example 30

Preparation of α,α'-bis-{4-(pyridin-2-yl-methylene-amino)-3,5-diisopropylphenyl}-4-bromo-toluene (20)

To a suspension of 4 (0.33 g, 0.71 mmol) in absolute ethanol (2 ml) was added 2-pyridinecarboxaldehyde (0.20 ml, 0.21 mmol, 3 eq.). The mixture was stirred at 40° C. overnight. On cooling to room temperature the suspension was filtered, washed with cold ethanol and dried under reduced pressure to afford 20 as a yellow solid (0.26 g, 63%).

Compound 20: ES mass spectrum, m/z 729 [M+H]$^+$; IR (cm$^{-1}$) 1640, 1585, 1567 (C=N); $^1$H NMR (CDCl$_3$), δ1.01 (d, 12H, $^3$J(HH) 6.7, CH(C$\underline{H}_3$)$_2$), 2.88 (sept, 4H, C$\underline{H}$(CH$_3$)$_2$), 5.36 (s, 1H, CH), 6.83 (s, 4H, Ar—H), 6.92 (d, 2H, $^3$J(HH) 8.2, Ar—H), 7.3-7.4 (m, 4H, Ar—H, Py-H), 7.77 (td, 2H, $^3$J(HH) 7.8, 0.6, Py-H), 8.20 (d, 2H, $^3$J(HH) 7.9, Py-H), 8.25 (s, 2H, H$\underline{C}$=N), 8.65 (dt, 2H, $^3$J(HH) 4.7, 0.6, Py-H); $^{13}$C NMR (CDCl$_3$, $^1$H gated decoupled), δ 23.5 (s, CH(C$\underline{H}_3$)$_2$), 23.6 (s, CH(C$\underline{H}_3$)$_2$), 28.0 (s, C$\underline{H}$(CH$_3$)$_2$), 56.2 (s, CH), 119.8 (s, Ar), 121.3 (s, Ar), 124.2 (s, Ar), 125.3 (s, Ar), 131.1 (s, Ar), 131.2 (s, Ar), 136.8 (s, Ar), 137.2 (s, Ar), 139.5 (s, Ar), 144.4 (s, Ar), 146.5 (s, Ar), 149.7.3 (s, Ar), 154.4 (s, Ar), 163.1 (s, C=N).

Example 31

Preparation of α,α'-bis-{4-(pyridin-2-yl-methylene-amino)-3,5 diisopropylphenyl}-4-hydroxy-toluene (21)

To a suspension of 5 (0.30 g, 0.66 mmol) in absolute ethanol (2 ml) was added 2-pyridinecarboxaldehyde (0.19 ml, 0.20 mmol, 3 eq.). The mixture was stirred at 50° C. overnight. On cooling to room temperature the suspension was filtered, washed with cold ethanol and dried under reduced pressure to afford 21 as a yellow solid (0.27 g, 66%).

Compound 21: ES mass spectrum, m/z 637 [M+H]$^+$; IR (cm$^{-1}$) 1640, 1585, 1567 (C=N); $^1$H NMR (CDCl$_3$), δ1.00 (d, 12H, $^3$J(HH) 6.7, CH(C$\underline{H}_3$)$_2$), 2.88 (sept, 4H, C$\underline{H}$(CH$_3$)$_2$), 5.34 (s, 1H, CH), 6.65 (d, 2H, $^3$J(HH) 8.8, Ar—H), 6.84 (s, 4H, Ar—H), 6.94 (d, 2H, $^3$J(HH) 8.8, Ar—H), 7.3-7.4 (m, 2H, Py-H), 7.78 (t, 2H, $^3$J(HH) 7.8, 0.6, Py-H), 8.22 (d 2H, $^3$J(HH) 7.9, Py-H), 8.26 (s, 2H, H$\underline{C}$=N), 8.66 (dt, 2H, 3J(HH) 4.7, 0.6, Py-H); $^{13}$C NMR (CDCl$_3$, $^1$H gated decoupled), δ 23.8 (s, $\underline{C}$H(CH$_3$)$_2$), 24.0 (s, CH(C$\underline{H}_3$)$_2$), 28.4 (s, $\underline{C}$H(CH$_3$)$_2$), 56.0 (s, CH), 115.0 (s, Ar), 121.5 (s, Ar), 124.0 (s, Ar), 124.3 (s, Ar), 125.4 (s, Ar), 127.9 (s, Ar), 130.4 (s, Ar), 132.6 (s, Ar), 136.8

(s, Ar), 137.1 (s, Ar), 140.7 (s, Ar), 146.0 (s, Ar), 149.5 (s, Ar), 154.5 (s, Ar), 163.2 (s, C=N).

Example 32

Preparation of α,α'-bis-{4-(pyridin-2-yl-methyleneamino)-3,5-diisopropylphenyl}-4-nitro-toluene (22)

To a suspension of 6 (0.30 g, 0.62 mmol) in absolute ethanol (2 ml) was added 2-pyridinecarboxaldehyde (0.18 ml, 0.19 mmol, 3 eq.) and one drop of formic acid. The mixture was stirred at 50° C. overnight. On cooling to room temperature the suspension was filtered, washed with cold ethanol and dried under reduced pressure to afford 22 as a yellow solid (0.25 g, 62%).

Compound 22: ES mass spectrum, m/z 666 [M+H]$^+$; IR (cm$^{-1}$), 1643 1586, 1567 (C=N); $^1$H NMR (CDCl$_3$), δ1.01 (d, 12H, $^3$J(HH) 6.7, CH(CH$_3$)$_2$) 2.88 (sept, 4H, CH(CH$_3$)$_2$), 5.51 (s, 1H, CH), 6.81 (s, 4H, Ar—H), 7.2-7.3 (m, 4H, Py-H, Ar—H), 7.77 (m, 2H, Py-H), 8.10 (d, 2H, $^3$J(HH) 7.9, Ar—H), 8.18 (d, 2H, $^3$J(HH) 7.9, Py-H), 8.26 (s, 2H, HC=N), 8.65 (d, 2H, $^3$J(HH) 3.5, Py-H); $^{13}$C NMR (CDCl$_3$, $^1$H gated decoupled), δ 23.5 (s, CH(CH$_3$)$_2$), 23.6 (s, CH(CH$_3$)$_2$), 28.0 (s, CH(CH$_3$)$_2$), 56.7 (s, CH), 121.4 (s, Ar), 123.4 (s, Ar), 124.2 (s, Ar), 125.4 (s, Ar), 130.2 (s, Ar), 136.8 (s, Ar), 137.5 (s, Ar), 138.4 (s, Ar), 146.4 (s, Ar), 146.9 (s, Ar), 149.7 (s, Ar), 153.2 (s, Ar), 154.3 (s, Ar), 163.2 (s, C=N).

Example 33

Preparation of α,α'-bis-{4-(pyridin-2-yl-methyleneamino)-3,5-diisopropylphenyl}-4-isopropyl-toluene (23)

To a suspension of 10 (0.30 g, 0.63 mmol) in absolute ethanol (2 ml) was added 2-pyridinecarboxaldehyde (0.18 ml, 0.19 mmol, 3 eq.). The mixture was stirred at 50° C. overnight. On cooling to room temperature the suspension was filtered, washed with cold ethanol and dried under reduced pressure to afford 23 as a yellow solid (0.32 g, 77%).

Compound 23: ES mass spectrum, m/z 663 [M+H]$^+$; $^1$H NMR (CDCl$_3$), δ1.01 (d, 24H, $^3$J(HH) 6.7, CH(CH$_3$)$_2$), 1.17 (d, 6H, $^3$J(HH) 6.7, CH(CH$_3$)$_2$2.86 (sept, 5H, CH(CH$_3$)$_2$), 5.38 (s, 1H, CH), 6.86 (s, 4H, Ar—H), 7.07 (m, 4H, Ar—H), 7.3-7.4 (m, 2H, Py-H), 7.77 (td, 2H, $^3$J(HH) 7.8, 0.6, Py-H), 8.19 (d, 2H, $^3$J(HH) 7.9, Py-H), 8.26 (s, 2H, HC=N), 8.65 (dt, 2H, $^3$J(HH) 4.7, 0.6, Py-H); $^{13}$C NMR (CDCl$_3$, $^1$H gated decoupled), δ 23.9 (s, CH(CH$_3$)$_2$), 24.0 (s, CH(CH$_3$)$_2$), 24.4 (s, CH(CH$_3$)$_2$), 28.4 (s, CH(CH$_3$)$_2$), 34.1 (s, CH(CH$_3$)$_2$), 56.9 (s, CH), 121.7 (s, Ar), 124.7 (s, Ar), 125.6 (s, Ar), 126.4 (s, Ar), 129.7 (s, Ar), 137.1 (s, Ar), 137.3 (s, Ar), 140.8 (s, Ar), 142.9 (s, Ar), 146.7 (s, Ar), 146.8 (s, Ar), 150.1 (s, Ar), 154.9 (s, Ar), 163.4 (s, C=N).

Example 34

Preparation of {4-(pyridin-2-yl-methyleneamino)-3,5-dimethylphenyl}-{4-(pyridin-2-yl-methyleneamino)-3,5-diisopropylphenyl}-methane (24)

To a suspension of 10 (0.34 g, 1.97 mmol) in absolute ethanol (2 ml) was added 2-pyridinecarboxaldehyde (0.56 ml, 5.91 mmol, 3 eq.) and one drop of formic acid. The mixture was stirred at 45° C. overnight. On cooling to room temperature the suspension was filtered, washed with cold ethanol and dried under reduced pressure to afford 24 as a yellow solid (0.20 g, 37%).

Compound 24: ES mass spectrum, m/z 487 [M+H]$^+$; $^1$H NMR (CDCl$_3$), δ1.08 (d, 12H, $^3$J(HH) 6.7, CH(CH$_3$)$_2$), 2.08 (s, 6H, CH$_3$), 2.88 (sept, 4H, CH(CH$_3$)$_2$), 3.84 (s, 2H, CH$_2$), 6.81 (s, 2H, Ar—H), 6.91 (s, 2H, Ar—H), 7.2-7.3 (m, 2H, Py-H), 7.7-7.8 (m, 2H, Py-H), 8.1-8.3 (m, 4H, Py-H/HC=N), 8.6-8.7 (m, 2H, Py-H); $^{13}$c NMR (CDCl$_3$, $^1$H gated decoupled), δ 18.8 (s, CH$_3$), 23.9 (s, CH$_3$), 28.4 (s, CH), 43.4 (s, CH$_2$), 121.7 (s, Ar), 124.2 (s, Ar), 125.7 (s, Ar), 128.2 (s, Ar), 129.0 (s, Ar), 137.2 (s, Ar), 137.7 (s, Ar), 150.0 (s, Ar), 156.2 (s, Ar), 163.4 (s, C=N), 163.9 (s, C=N).

Example 35

Preparation of bis-{((6-pyridin-2-yl)pyridin-2-yl-methyleneamino)-3,5-dimethylphenyl}-methane (25)

To a suspension of 2,2'-bipyridinyl-6-carbaldehyde (0.38 g, 2.07 mmol) in absolute ethanol (5 ml) was added 2a (0.13 g, 0.52 mmol, 0.25 eq.) and one drop of formic acid. The orange solution was heated to reflux for 24 hours. On cooling to 0° C. the suspension was filtered, washed with cold diethyl ether (100 ml) and dried under reduced pressure to give 25 as yellow solid (0.22 g, 71%).

Compound 25: ES mass spectrum, m/z 587 [M+H]$^+$. $^1$H NMR (CDCl$_3$), 2.14 (s, 12H, Ar—CH$_3$), 3.53 (s, 2H, CH$_2$), 6.89 (s, 4H, Ar—H), 7.21 (dd, 2H, $^3$J(HH) 6.1, 4J(HH) 1.2, Py-H), 7.72 (td, 2H, $^3$J(HH) 7.8, $^4$J(HH) 1.6, Py-H), 7.86 (t, 2H, $^3$J(HH) 7.8, Py-H), 8.21 (dd, 2H, $^3$J(HH) 7.8 Hz, $^4$J(HH) 0.9, Py-H), 8.34 (s, 2H, HC=N), 8.41 (d, 2H, $^3$J(HH) 7.8, Py-H), 8.44 (dd, 2H, $^3$J(HH) 7.4, $^4$J(HH) 0.9, Py-H), 8.60 (dd, 2H, $^3$J(HH) 4.5, $^4$J(HH) 0.7, Py-H).

Example 36

Preparation of bis-{(6-pyridin-2-yl)pyridin-2-yl-methyleneamino)-3,5-diisopropylphenyl}-methane (26a)

To a suspension of 2,2'-bipyridinyl-6-carbaldehyde (0.39 g, 2.09 mmol) in absolute ethanol (5 ml) was added 2b (0.19 g, 0.53 mmol, 0.25 eq.) and one drop of formic acid. The brown solution was heated to reflux for 24 hours. On cooling to 0° C., the suspension was filtered, washed with cold ethanol and dried under reduced pressure to give 26a as a brown solid (0.19 g, 52%).

Compound 26a: ES mass spectrum, m/z 699 [M+H]$^+$; IR (cm$^{-1}$), 1640 1580, 1547 (C=N); $^1$H NMR (CDCl$_3$), δ 1.07 (d, 12H, $^3$J(HH) 6.7, CH(CH$_3$)$_2$), 1.10 (d, 12H, $^3$J(HH) 6.8, CH(CH$_3$)$_2$), 2.91 (sept, 4H, CH(CH$_3$)$_2$), 3.28 (s, 2H, CH$_2$), 6.95 (s, 4H, Ar—H), 7.21 (qd, 2H, $^3$J(HH) 6.1, $^4$J(HH) 1.2 Hz, Py-H), 7.72 (td, 2H, $^3$J(HH) 7.8, $^4$J(HH) 1.8, Py-H), 7.86 (t, 2H, $^3$J(HH) 7.8, Py-H), 8.21 (dd, 2H, $^3$J(HH) 7.8, $^4$J(HH) 0.9, Py-H), 8.34 (s, 2H, HC=N), 8.41 (d, 2H, $^3$J(HH) 7.8, Py-H), 8.44 (dd, 2H, $^3$J(HH) 7.4, $^4$J(HH) 0.9, Py-H), 8.60 (dd, 2H, $^3$J(HH) 4.5, $^4$J(HH) 0.7, Py-H); $^{13}$C NMR (CDCl$_3$, $^1$H gated decoupled), δ 22.5 (s, CH$_3$), 27.0 (s, CH$_3$), 29.3 (s, CH), 40.6 (s, CH$_2$), 120.0 (s, Ar), 120.2 (s, Ar), 121.6 (s, Ar), 122.7 (s, Ar), 122.9 (s, Ar), 135.9 (s, Ar), 136.3 (s, Ar), 136.5 (s, Ar), 145.5 (s, Ar), 148.2 (s, Ar), 153.0 (s, Ar), 154.6 (s, Ar), 155.0 (s, Ar), 162.1 (s, Ar), 162.5 (s, C=N).

Example 37

Preparation of bis-{(6-pyridin-2-yl)pyridin-2-yl-ethyleneamino)-3,5-diisopropylphenyl}-methane (26b)

To a suspension of 2,2'-bipyridinyl-6-acetyl-2,2'-bipyridine (0.067 g, 0.34 mmol) in n-butanol (5 ml) was added 2b (0.05 g, 0.14 mmol, 0.4 eq.) and one drop of glacial acetic acid. The brown solution was heated to reflux for 48 hours. On cooling to room temperature, the suspension was filtered, washed with cold ethanol and dried under reduced pressure to give 26b as a brown solid (0.051 g, 52%).

Compound 26b: ES mass spectrum, m/z 727 [M+H]$^+$; $^1$H NMR (CDCl$_3$): $\delta$1.07 (d, 12H, $^3$J(HH) 6.7, CH(C$\underline{H}_3$)$_2$), 1.09 (d, 12H, $^3$J(HH) 6.8, CH(C$\underline{H}_3$)$_2$), 2.17 (s, 6H, MeC=N), 2.78 (sept, 4H, C$\underline{H}$(CH$_3$)$_2$), 3.98 (s, 2H, CH$_2$), 6.95 (s, 4H, Ar—H), 7.21 (m, 2H, Py-H), 7.71 (m, 2H, Py-H), 7.85 (m, 2H, Py-H), 8.25 (m, 2H, Py-H), 8.41 (m, 4H, Py-H), 8.71 (m, 2H, Py-H); $^{13}$C NMR (CDCl$_3$, 1H gated decoupled), $\delta$ 167.3 (s, C=N).

Formulae for Examples 15-37

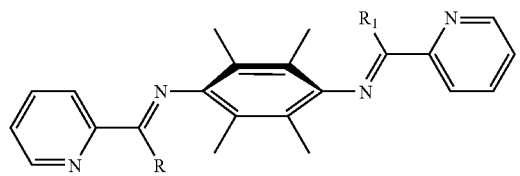

Example 15 (11a) R = R$_1$ = H
Example 16 (11b) R = R$_1$ = Me
Example 17 (11c) R = H, R$_1$ = Me

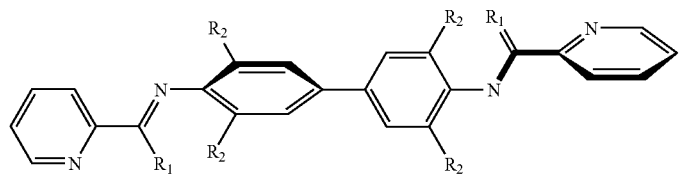

Example 20 (13a) R$_1$ = H, R$_2$ = Me
Example 21 (13b) R$_1$ = Me, R$_2$ = Me
Example 22 (14a) R$_1$ = H, R$_2$ = i-Pr
Example 23 (14b) R$_1$ = Me, R$_2$ = i-Pr

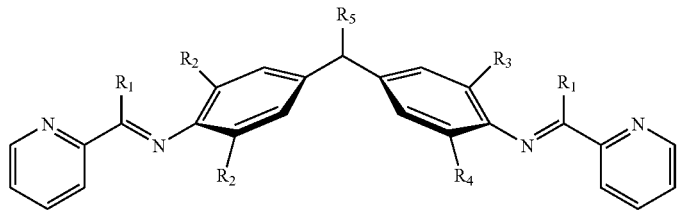

Example 26 (17) R$_1$ = H, R$_2$ = R$_3$ = R$_4$ = Me, R$_5$ = H
Example 27 (18a) R$_1$ = H, R$_2$ = R$_3$ = R$_4$ = i-Pr, R$_5$ = H
Example 28 (18b) R$_1$ = Me, R$_2$ = R$_3$ = R$_4$ = i-Pr, R$_5$ = H
Example 29 (19) R$_1$ = H, R$_2$ = R$_3$ = R$_4$ = i-Pr, R$_5$ = Ph
Example 30 (20) R$_1$ = H, R$_2$ = R$_3$ = R$_4$ = i-Pr, R$_5$ = Ph-4-Br
Example 31 (21) R$_1$ = H, R$_2$ = R$_3$ = R$_4$ = i-Pr, R$_5$ = Ph-4-OH
Example 32 (22) R$_1$ = H, R$_2$ = R$_3$ = R$_4$ = i-Pr, R$_5$ = Ph-4-NO$_2$
Example 33 (23) R$_1$ = H, R$_2$ = R$_3$ = R$_4$ = i-Pr, R$_5$ = Ph-4-i-Pr
Example 34 (24) R$_1$ = H, R$_2$ = i-Pr = R$_3$ = R$_4$ = Me, R$_5$ = H

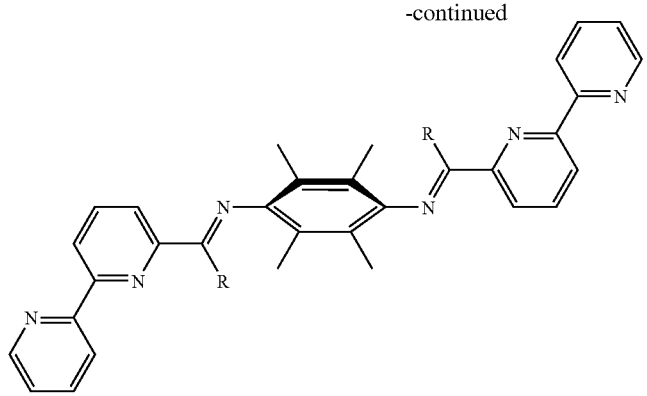

Example 18 (12a) R = H
Example 19 (12b) R = Me

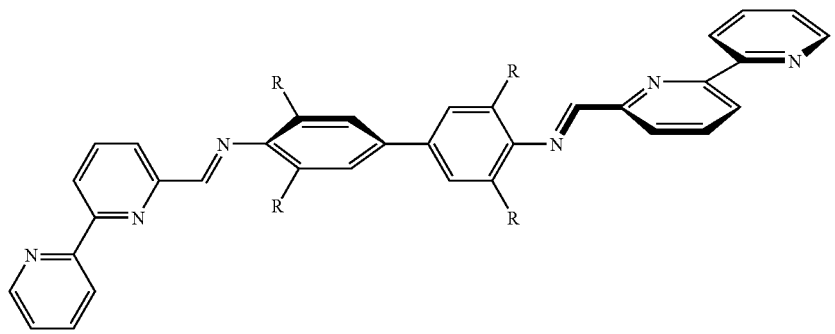

Example 24 (15) R = Me
Example 25 (16) R = i-Pr

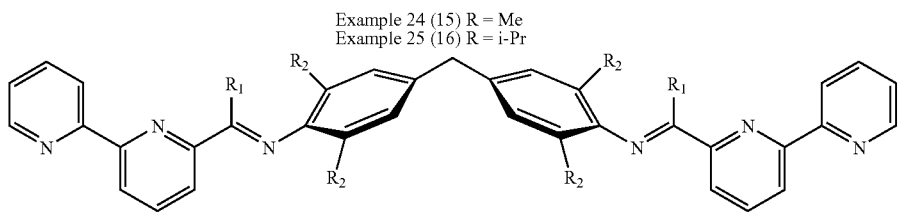

Example 35 (25) R$_1$ = H, R$_2$ = Me
Example 36 (26a) R$_1$ = H, R$_2$ = i-Pr
Example 37 (26b) R$_1$ = Me, R$_2$ = i-Pr Where Ph-4-Br=4-bromotoluene, Ph-4-OH=4-hydroxytoluene, Ph-4-NO$_2$=4-nitrotoluene, and Ph-4-i-Pr=4-isopropyltoluene.

Preparation of Complexes

All complexation reactions were carried out under an atmosphere of dry, oxygen-free nitrogen, using standard Schlenk techniques or in a nitrogen purged glove box. n-Butanol was dried and deoxygenated by distillation over sodium metal under nitrogen. The anhydrous metal dichlorides and NiBr$_2$.DME (Nickel bromide ethylene glycol dimethyl ether) were purchased from Aldrich Chemical Co. and used without any further purification. All other chemicals were obtained commercially and used without further purification. The infrared spectra were recorded with Universal ATR sampling accessories on a Perkin Elmer Spectrum One FTIR instrument. FAB mass spectra were recorded using a Kratos Concept spectrometer with NBA (nitrobenzyl alcohol) as the matrix [samples placed on the end of probe within matrix and bombarded with xenon atoms at about 7 kV, Mach3 software, and probe temperature 50° C. Data for the crystal structure determinations were collected on a Bruker APEX 2000 CCD diffractometer and solved using SHELXTL version 6.10 [Bruker (2000). SHELXTL. Version 6.10 for PC. Bruker AXS Inc., Madison, Wis., USA; G. M. Sheldrick (1997). SHELXS97 and SHELXL97. University of Göttingen, Germany]. Magnetic susceptibility studies were performed using an Evans Balance at ambient temperature.

Example 38

Preparation of [2,3,5,6-tetramethyl-N,N-bis-(pyridin-2-ylmethylene)-benzene-1,4-diamine]Ni$_2$Br$_4$ (27a)

A suspension of NiBr$_2$.DME (0.18 g, 0.58 mmol) in n-butanol (5 ml) was stirred at 90° C. for 30 minutes. 11a was added (0.10 g, 0.29 mmol, 0.5 eq.) and the mixture was heated to 90° C. overnight. On cooling to ambient temperature, hexane was added to induce precipitation of the product. Following filtration, washing with hexane and drying under reduced pressure, 27a was isolated as an orange solid (0.14 g, 63%).

Compound 27a: IR (cm$^{-1}$) 1594, 1567 (C=N); $\mu_{eff}$ 4.19 BM.

Layering of a N,N-dimethylformamide (DMF) solution of 27a with diethyl ether gave red crystals of the DMF adduct of 27a, [{(C$_5$H$_4$N)CHN(2,3,5,6-Me$_4$C$_6$)NHC(C$_5$H$_4$N)}(DMF)$_6$ Ni$_2$Br$_2$]Br$_2$ (27a'), suitable for a single crystal X-ray diffraction study (FIG. 1).

Example 39

Preparation of [2,3,5,6-tetramethyl-N,N-bis-(pyridin-2-ylethylidene)-benzene-1,4-diamine]Ni$_2$Br$_4$ (27b)

A suspension of NiBr$_2$.DME (0.17 g, 0.54 mmol) in n-butanol (5 ml) was stirred at 90° C. for 30 minutes. 11b (0.10 g, 0.27 mmol, 0.5 eq.) was added and the mixture heated to 90° C. for a further one hour. On cooling to ambient temperature, hexane was added to induce precipitation of the product. Following filtration, washing with hexane and drying under reduced pressure, 27b was isolated as a green solid (0.15 g, 70%).

Compound 27b: IR (cm$^{-1}$) 1596, 1571 (C=N); $\mu_{eff}$ 4.16 BM.

Figure 2:
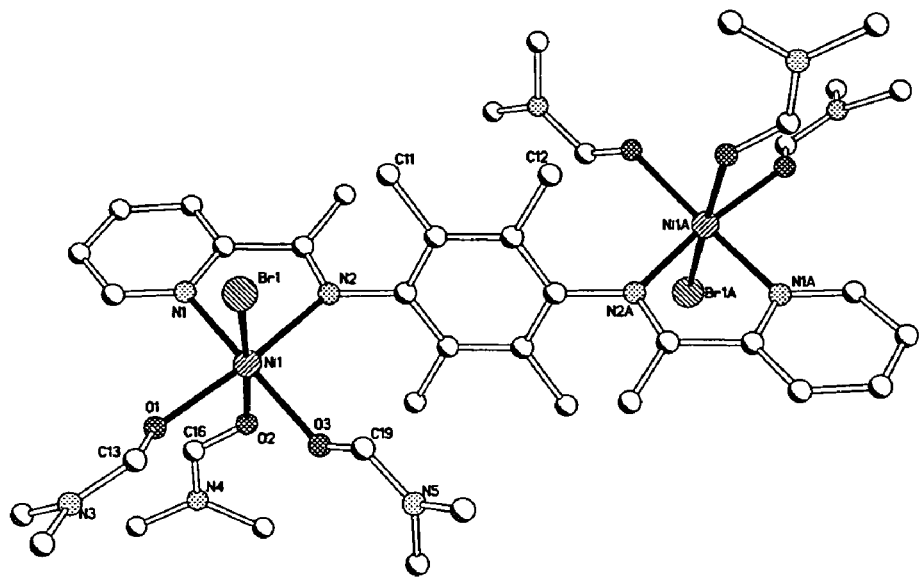
FIG. 2 is a representation of the molecular structure of 27b' (example 39).

Layering of a N,N-dimethylformamide (DMF) solution of 27b with diethyl ether gave red crystals of the DMF adduct of 27b, [{(C$_5$H$_4$N)CMeN(2,3,5,6-Me$_4$C$_6$)NMeC(C$_5$H$_4$N)}(DMF)$_6$Ni$_2$Br$_2$]Br$_2$ (27b'), suitable for a single crystal X-ray diffraction study (FIG. 2).

Anal. (C$_{24}$H$_{26}$N$_4$Ni$_2$Br$_{40}$.4DMF.8H$_2$O) calcd: C, 34.75; H, 5.68; N, 8.81. Found: C, 34.92; H, 5.92; N, 8.81%.

Example 40

Preparation of [2,3,5,6-tetramethyl-N-(pyridin-2-ylethylidene-N-(pyridin-2-ylmethylene)-benzene-1,4-diamine]Ni$_2$Br$_4$ (27c)

A suspension of NiBr$_2$.DME (0.17 g, 0.56 mmol) in n-butanol (5 ml) was stirred at 90° C. for 30 minutes. 11c (0.10 g, 0.28 mmol, 0.5 eq.) was added and the mixture stirred at 90° C. for one hour. On cooling to ambient temperature, hexane was added to induce precipitation of the product. Following filtration, washing with hexane and drying under reduced pressure, 27c was isolated as a red solid (0.12 g, 56%).

Compound 27c: $\mu_{eff}$ 3.89 BM.

Figure 3:
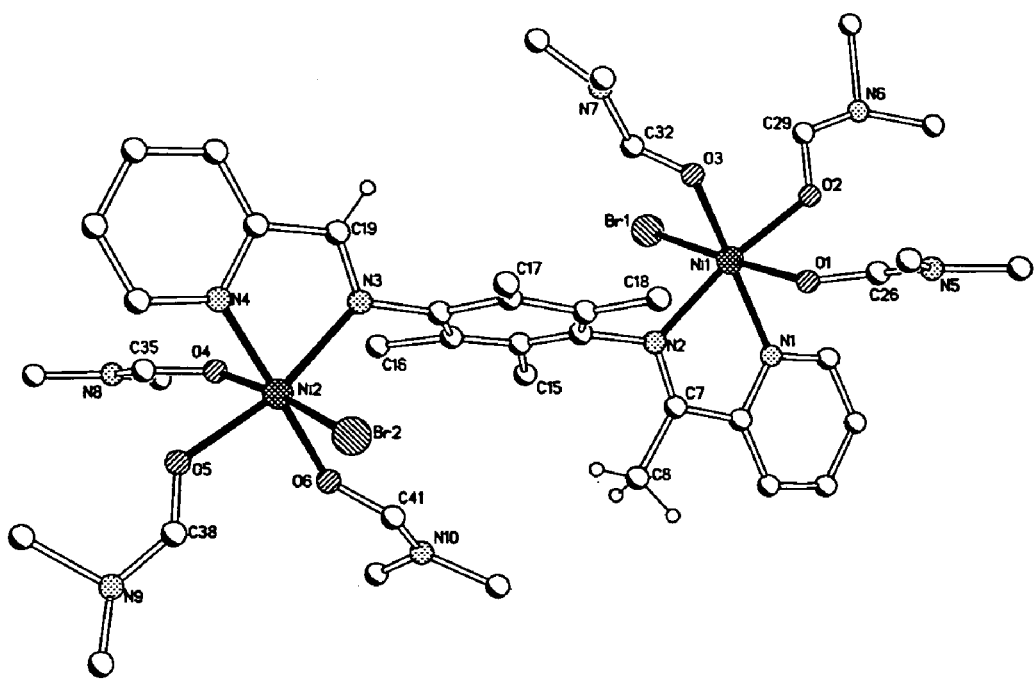
FIG. 3 is a representation of the molecular structure of 27c' (example 40).

Layering of a N,N-dimethylformamide (DMF) solution of 27c with diethyl ether gave red crystals of the DMF adduct of 27c, [{(C$_5$H$_4$N)CMeN(2,3,5,6-Me$_4$C$_6$)NHC(C$_5$H$_4$N)}(DMF)$_6$Ni$_2$Br$_2$]Br$_2$ (27c'), suitable for a single crystal X-ray diffraction study (FIG. 3).

Example 41

Preparation of [2,3,5,6-tetramethyl-N,N-bis-(pyridin-2-ylmethylene)-benzene-1,4-diamine]Ni$_2$Cl$_4$ (28)

A suspension of NiCl$_2$ (0.08 g, 0.58 mmol) in n-butanol (5 ml) was stirred at 90° C. for 30 minutes. 11a was added (0.10 g, 0.29 mmol, 0.5 eq.) and the mixture was heated to 90° C. overnight. On cooling to ambient temperature, hexane was added to induce precipitation of the product. Following filtration, washing with hexane and drying under reduced pressure, 28 was isolated as an orange solid (0.14 g, 63%).

Compound 28: FAB mass spectrum, m/z 566 [M-Cl]$^+$, 530 [M-2Cl]$^+$, 495 [M-3Cl]$^+$; IR (cm$^{-1}$) 1595 (C=N); $\mu_{eff}$ 4.20 BM.

Figure 4:
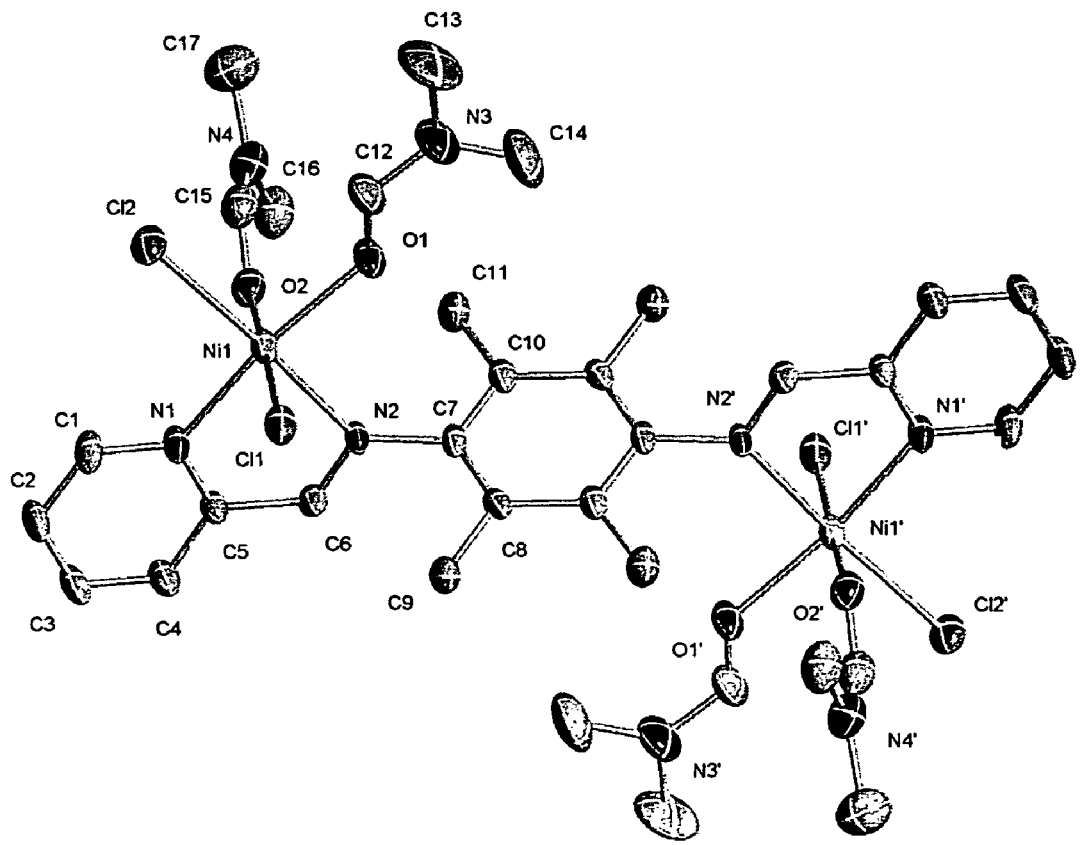
FIG. 4 is a representation of the molecular structure of 28' (example 41).

Layering of a N,N-dimethylformamide (DMF) solution of 28 with diethyl ether gave red crystals of the DMF adduct of 28, [{(C$_5$H$_4$N)CHN(2,3,5,6-Me$_4$C$_6$)NHC(C$_5$H$_4$N)}(DMF)$_4$Ni$_2$Cl$_4$] (28'), suitable for a single crystal X-ray diffraction study (FIG. 4). IR (cm$^{-1}$) 1645 (C=O), 1595 (C=N).

Example 42

Preparation of [2,3,5,6-tetramethyl-N,N-bis-{(6-pyridin-2-yl)pyridin-2-ylmethylene}-benzene-1,4-diamine]Fe$_2$Cl$_4$ (29a)

Under an atmosphere of nitrogen, anhydrous FeCl$_2$ (0.052 g, 0.41 mmol) was dissolved in n-butanol (4 ml) by stirring at 90° C. for 30 minutes. To this yellow-green solution, 12a (0.10 g, 2.0 mmol, 0.5 eq.) was added and the mixture stirred at 100° C. for 30 minutes forming a green precipitate. On cooling to ambient temperature, hexane was added to complete the precipitation. Following filtration, washing with further hexane and drying under reduced pressure, complex 29a was isolated as an olive green powder (0.09 g, 55%).

Complex 29a: FAB mass spectrum, m/z 716 [M-Cl]$^+$, 680 [M-2Cl]$^+$; IR (cm$^{-1}$) 1591 (C=N).

Example 43

Preparation of [2,3,5,6-tetramethyl-N,N-bis-{(6-pyridin-2-yl)pyridin-2-ylethylidene}-benzene-1,4-diamine]Fe$_2$Cl$_4$ (29b)

Under an atmosphere of nitrogen, anhydrous FeCl$_2$ (0.034 g, 0.27 mmol) was dissolved in n-butanol (5 ml) by stirring at 90° C. for 30 minutes. To this yellow-green solution, 12b (0.07 g, 0.13 mmol, 0.5 eq.) was added and the mixture stirred at 110° C. for 30 minutes. On cooling to ambient temperature, hexane was added to induce precipitation of the product. Following filtration and washing with more hexane, complex 28b was isolated as a grey/black powder (0.06 g, 57%).

Compound 29b: FAB mass spectrum, m/z 743 [M-Cl]$^+$, 707 [M-2Cl]$^+$; IR (cm$^{-1}$) 1593, 1576 (C=N); $\square_{eff}$ 6.48 BM.

Example 44

Preparation of [3,5,3',5'-tetramethyl-N,N-bis-(pyridin-2-ylmethylene)-biphenyl-4,4'-diamine]Ni$_2$Cl$_4$ (30a)

To a stirred suspension of anhydrous NiCl$_2$ (0.038 g, 0.29 mmol) in n-butanol (10 ml) at 120° C. was added 13a (0.06 g, 0.15 mmol, 0.5 eq.) and the mixture heated to 120° C. overnight. After cooling to ambient temperature, the suspension was concentrated and washed several times with hexane. Following filtration and drying under reduced pressure, complex 30a was afforded as an orange solid (0.023 g, 24%).

Compound 30a: FAB mass spectrum, m/z 641 [M-Cl]$^+$, 569 [M-3Cl]$^+$, 510 [M-3Cl—Ni]$^+$; IR (cm$^{-1}$) 1591, 1573 (C=N). Layering of a N,N-dimethylformamide (DMF) solution of 30a with diethyl ether gave red crystals of the DMF adduct of 30a, [{(C$_5$H$_4$N)CHN(2,2'6,6'-Me$_4$Cl$_2$H$_4$)NHC(C$_5$H$_4$N)}(DMF)$_4$Ni$_2$Cl$_4$] (30a'). Anal. (C$_{28}$H$_{26}$N$_4$Ni$_2$Cl$_4$.4DMF.0.5H$_2$O) calcd: C, 48.18; H, 5.77; N, 11.23. Found: C, 48.30; H, 5.61; N, 10.92%.

Example 45

Preparation [3,5,3',5'-tetramethyl-N,N-bis-(pyridin-2-yl-ethylidene)-biphenyl-4,4'-diamine]Ni$_2$Cl$_4$ (30b)

To a stirred suspension of anhydrous NiCl$_2$ (0.04 g, 0.29 mmol) in n-butanol (12 ml) at 120° C. was added 13b (0.06 g, 0.14 mmol) and the mixture heated to 120° C. overnight. After cooling to ambient temperature, the suspension was concentrated and washed several times with hexane. Following filtration and drying under reduced pressure, complex 30b was afforded as an orange solid (0.023 g, 23%).

Compound 30b: IR (cm$^{-1}$) 1595, 1578 (C=N).

Example 46

Preparation of [3,5,3',5'-tetraisopropyl-N,N,-bis-(pyridin-2-ylmethylene)-biphenyl-4,4'-diamine]Ni$_2$Cl$_4$ (31a)

To a stirred suspension of anhydrous NiCl$_2$ (0.06 g, 0.46 mmol) in n-butanol (15 ml) at 120° C. was added 14a (0.12 g, 0.23 mmol, 0.5 eq.) and the mixture heated to 120° C. overnight. After cooling to ambient temperature, the suspension was concentrated and washed several times with hexane. Following filtration and drying under reduced pressure, complex 31a was afforded as an orange solid (0.10 g, 57%).

Compound 31a: FAB mass spectrum, m/z 754 [M-Cl]$^+$.

Example 47

Preparation of [3,5,3',5'-tetraisopropyl-N,N,-bis-(pyridin-2-yl-ethylidene)-biphenyl-4,4'-diamine]Ni$_2$Cl$_4$ (31b)

To a stirred suspension of anhydrous NiCl$_2$ (0.08 g, 0.59 mmol) in n-butanol (5 ml) at 120° C. was added 14b (0.17 g, 0.30 mmol, 0.5 eq.) and the mixture heated to 120° C. overnight. After cooling to ambient temperature, the suspension was concentrated and washed several times with hexane. Following filtration and drying under reduced pressure, complex 31b was afforded as an orange solid (0.10 g, 41%).

Compound 31b: FAB mass spectrum, m/z 783 [M-Cl]$^+$, 746 [M-2Cl]$^+$.

Example 48

Preparation of [3,5,3',5'-tetramethyl-N,N-bis-{(6-pyridin-2-yl)pyridin-2-ylmethylene}-biphenyl-4,4'-diamine]Fe$_2$Cl$_4$ (32)

Under an atmosphere of nitrogen, anhydrous FeCl$_2$ (0.05 g, 0.42 mmol) was dissolved in n-butanol (4 ml) by stirring at 90° C. for 30 minutes. To this yellow-green solution, 15 (0.12 g, 0.21 mmol, 0.5 eq.) was added and the mixture stirred at 100° C. for 30 minutes forming a brown/grey suspension. On cooling to ambient temperature, hexane was added to complete the precipitation. Following filtration and washing with more hexane, complex 32 was isolated as a brown powder (0.022 g, 13%).

Complex 32: FAB mass spectrum, m/z 790 [M-Cl]$^+$; $\square_{eff}$ 5.34 BM.

Example 49

Preparation of [3,5,3',5'-tetraisopropyl-N,N-bis-{(6-pyridin-2-yl)pyridin-2-ylmethylene}-biphenyl-4,4'-diamine]Fe$_2$Cl$_4$ (33)

Under an atmosphere of nitrogen, anhydrous FeCl$_2$ (0.052 g, 0.42 mmol) was dissolved in n-butanol (4 ml) by stirring at 90° C. for 30 minutes. To this yellow-green solution, 16 (0.14 g, 0.21 mmol) was added and the mixture stirred at 100° C. for a further 30 minutes forming a grey/black precipitate. On cooling to ambient temperature, hexane was added to complete the precipitation. Following filtration, washing with more hexane and drying under reduced pressure, complex 33 was isolated as a black powder (0.026 g, 13%).

Complex 33: FAB mass spectrum, m/z 903 [M-Cl]$^+$, 867 [M-2Cl]$^+$; $\square_{eff}$ 6.66 BM.

Example 50

Preparation of [bis-{4-(pyridin-2-yl-methylene-amino)-3,5-dimethylphenyl}-methane]Ni$_2$C$_4$ (34)

To a stirred suspension of anhydrous NiCl$_2$ (0.42 g, 3.24 mmol) in n-butanol (30 ml) at 120° C. was added 17 (0.70 g, 1.62 mmol, 0.5 eq.) and the mixture heated to 120° C. overnight. After cooling to ambient temperature, the suspension was concentrated and washed several times with hexane. Following filtration and drying under reduced pressure, complex 34 was afforded as an orange powder (0.39 g, 35%).

Complex 34: IR (cm$^{-1}$) 1594, 1571 (C=N).

Example 51

Preparation of [bis-{4-(pyridin-2-yl-methylene-amino)-3,5-diisopropylphenyl}-methane]Ni$_2$C$_4$ (35a)

To a stirred suspension of anhydrous NiCl$_2$ (0.24 g, 1.83 mmol) in n-butanol (15 ml) at 120° C. was added 18a (0.50 g, 0.92 mmol, 0.5 eq.) and the mixture heated to 120° C. overnight. After cooling to ambient temperature, the suspension was concentrated and washed several times with hexane. Following filtration and drying under reduced pressure, complex 35a was isolated as a green powder (0.42 g, 56%).

Figure 5:
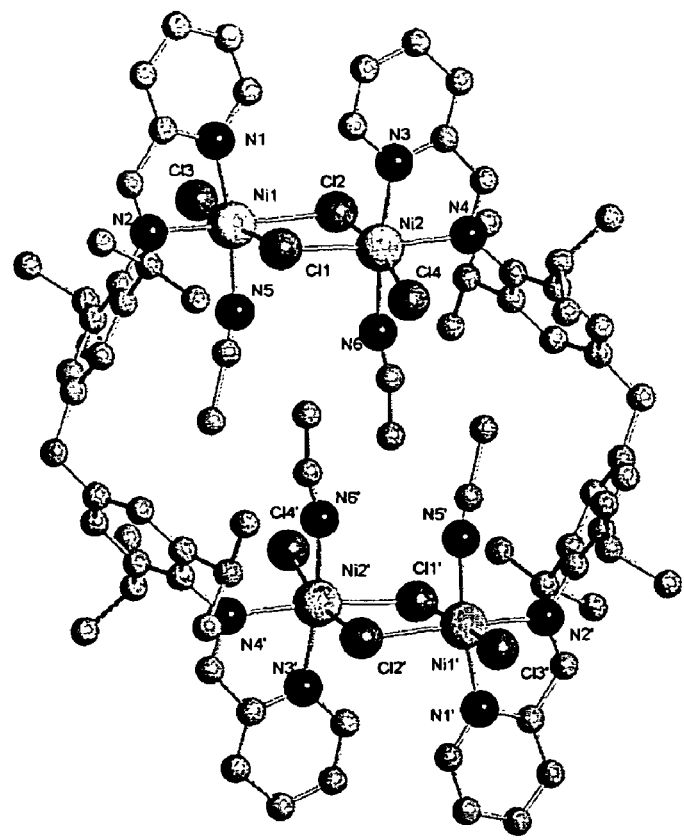
FIG. 5 is a representation of the molecular structure of 35a' (example 51).

Complex 35a: FAB mass spectrum, m/z 767 [M-Cl]$^+$, 732 [M-2Cl]$^+$, 695 [M-3Cl]$^+$; IR (cm$^{-1}$) 1591, 1573 (C=N). Prolonged standing of an acetonitrile solution of 35a gave crystals of the acetonitrile adduct of 35a, [{2-(2'-(CH=N)C$_5$H$_4$N)}$_2${1,1'-(CH$_2$)-3,5,3',5'-i-Pr$_4$Cl$_2$H$_4$}]$_2$Ni$_4$Cl$_8$(NCMe)$_4$ (35a'), suitable for a single crystal X-ray diffraction study (FIG. 5).

Example 52

Preparation of [bis-{4-(pyridin-2-yl-ethylidene-amino)-3,5-diisopropylphenyl}-methane]Ni$_2$Cl$_4$ (35b)

To a stirred suspension of anhydrous NiCl$_2$ (0.11 g, 0.86 mmol) in n-butanol (10 ml) at 120° C. was added 18b (0.25 g, 0.43 mmol, 0.5 eq.) and the mixture heated to 120° C. overnight. After cooling to ambient temperature, the suspension was concentrated and washed several times with hexane. Following filtration and drying under reduced pressure, complex 35b was afforded as a green powder (0.18 g, 51%).

Figure 6:
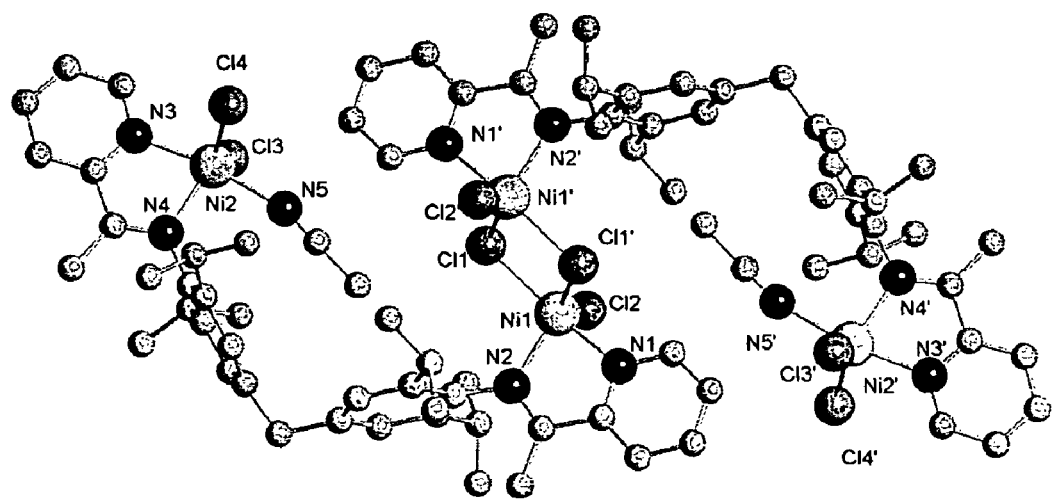
FIG. 6 is a representation of the molecular structure of 35b' (example 52).

Complex 35b: FAB mass spectrum, m/z 797 [M-Cl]$^+$, 760 [M-2Cl]$^+$, 723 [M-3Cl]$^+$; IR (cm$^{-1}$) 1596, 1573 (C=N). Prolonged standing of an acetonitrile solution of 35b gave green crystals of the acetonitrile adduct of 35b, [{2-(2'-(CMe=N)C$_5$H$_4$N)}$_2${1,1',-(CH$_2$)-3,5,3',5'-i-Pr$_4$Cl$_2$H$_4$}]$_2$Ni$_4$Cl$_8$(NCMe)$_2$ (35b'), suitable for a single crystal X-ray diffraction study (FIG. 6).

Example 53

Preparation of [bis-{4-(pyridin-2-yl-methylene-amino)-3,5-diisopropylphenyl}-toluene]Ni$_2$Cl$_4$ (36)

To a stirred suspension of anhydrous NiCl$_2$ (0.030 g, 0.23 mmol) in n-butanol (10 ml) at 120° C. was added 19 (0.07 g, 0.12 mmol, 0.5 eq.) and the mixture heated to 120° C. overnight. After cooling to ambient temperature, the suspension was concentrated and washed several times with hexane. Following filtration and drying under reduced pressure, complex 36 was afforded as a pale brown powder (0.05 g, 51%).

Complex 36: FAB mass spectrum, m/z 844 [M-Cl]$^+$.

Example 54

Preparation of [bis-{-4-(pyridin-2-yl-methylene-amino)-3,5-diisopropylphenyl}-4-bromotoluene] Ni$_2$Cl$_4$ (37)

To a stirred suspension of anhydrous NiCl$_2$ (0.107 g, 0.83 mmol) in n-butanol (10 ml) at 120° C. was added 20 (0.24 g, 0.44 mmol, 0.52 eq.) and the mixture heated to 120° C. overnight. After cooling to ambient temperature, the suspension was concentrated and washed several times with hexane. Following filtration and drying under reduced pressure, complex 37 was afforded as a dark green powder (0.19 g, 55%).

Compound 37: FAB mass spectrum, m/z 925 [M-Cl]$^+$, 888 [M-2Cl]$^+$; 851 [M-3Cl]$^+$; 751 [M-Ni-4Cl]$^+$; IR (cm$^{-1}$) 1597, 1571 (C=N).

Example 55

Preparation of [bis-{4-(pyridin-2-yl-methylene-amino)-3,5-diisopropylphenyl}-4-hydroxytoluene] Ni$_2$C$_4$ (38)

To a stirred suspension of anhydrous NiCl$_2$ (0.078 g, 0.60 mmol) in n-butanol (10 ml) at 120° C. was added 21 (0.20 g, 0.31 mmol, 0.52 eq.) and the mixture heated to 120° C. overnight. After cooling to ambient temperature, the suspension was concentrated and washed several times with hexane. Following filtration and drying under reduced pressure, complex 38 was afforded as a dark red powder (0.20 g, 71%).

Complex 38: FAB mass spectrum, m/z 859 [M-Cl]$^+$, 824 [M-2Cl]$^+$, 787 [M-3Cl]$^+$, 692 [M-Ni-4Cl]$^+$; IR (cm$^{-1}$) 1595, 1571 (C=N).

Example 56

Preparation of [bis-{4-(pyridin-2-yl-methyleneamino)-3, 5-dimethylphenyl}-4-nitrotoluene]Ni$_2$Cl$_4$ (39)

To a stirred suspension of anhydrous NiCl$_2$ (0.10 g, 0.60 mmol) in n-butanol (10 ml) at 120° C. was added 22 (0.25 g, 0.73 mmol, 0.52 eq.).) and the mixture heated to 120° C. overnight. After cooling to ambient temperature, the suspension was concentrated and washed several times with hexane. Following filtration and drying under reduced pressure, complex 39 was afforded as a yellow powder (0.16 g, 46%).

Complex 39: FAB mass spectrum, m/z 889 [M-Cl]$^+$, 853 [M-2Cl]$^+$, 818 [M-3Cl]$^+$, 631 [M-Ni-4Cl]$^+$; IR (cm$^{-1}$) 1595, 1571 (C=N).

Example 57

Preparation of [bis-{4-(pyridin-2-yl-methylene-amino)-3,5-diisopropylphenyl}-4-isopropyltoluene] Ni$_2$Cl$_4$ (40)

To a stirred suspension of anhydrous NiCl$_2$ (0.03 g, 0.55 mmol) in n-butanol (5 ml) at 120° C. was added 23 (0.07 g, 0.21 mmol, 0.5 eq.) and the mixture heated to 120° C. overnight. After cooling to ambient temperature, the suspension was concentrated and washed several times with hexane. Following filtration and drying under reduced pressure, complex 40 was afforded as a dark green powder (0.14 g, 52%).

Compound 40: FAB mass spectrum, m/z 887 [M-Cl]$^+$, 850 [M-2Cl]$^+$, 813 [M-3Cl]$^+$.

Example 58

Preparation of [{4-(pyridin-2-yl-methyleneamino)-3, 5-dimethylphenyl}-{4-(pyridin-2-yl-methylene-amino)-3,5-diisopropylphenyl}-methane]Ni$_2$Cl$_4$ (41)

To a stirred suspension of anhydrous NiCl$_2$ (0.05 g, 0.41 mmol) in n-butanol (10 ml) at 120° C. was added 24 (0.100 g, 0.21 mmol, 0.5 eq and the mixture heated to 120° C. overnight. After cooling to ambient temperature, the suspension was concentrated and washed several times with hexane. Following filtration and drying under reduced pressure, complex e 41 was afforded as a dark green powder (0.12 g, 78%).

Complex 41: FAB mass spectrum, m/z 712 [M-Cl]$^+$, 678 [M-2Cl]$^+$, 640 [M-3C]$^+$; IR (cm$^{-1}$) 1597, 1571 (C=N).

Example 59

Preparation of [bis-{((6-pyridin-2-yl)pyridin-2-yl-methyleneamino)-3,5-dimethylphenyl}-methane] Fe$_2$Cl$_4$ (42)

Under an atmosphere of nitrogen, anhydrous FeCl$_2$ (0.05 g, 0.40 mmol) was dissolved in n-butanol (4 ml) by stirring at 90° C. for 30 minutes. To this yellow-green solution was added 25 (0.12 g, 0.20 mmol, 0.5 eq.) and the mixture stirred at 100° C. for 30 minutes. On cooling to ambient temperature, hexane was added to complete the precipitation. Following filtration, washing with more hexane and drying under reduced pressure, complex 42 was isolated as a dark green powder (0.04 g, 22%).

Complex 42: FAB mass spectrum, m/z 769 [M-2Cl]$^+$; □$_{eff}$ 5.46 BM.

Example 60

Preparation of [bis-{(6-pyridin-2-yl)pyridin-2-yl-methyleneamino)-3,5-diisopropylphenyl}-methane] Fe$_2$Cl$_4$ (43a)

Under an atmosphere of nitrogen, anhydrous FeCl$_2$ (0.05 g, 0.41 mmol) was dissolved in n-butanol (4 ml) by stirring at 90° C. for 30 minutes. To this green-yellow solution, 26a (0.14 g, 0.20 mmol) was added and the mixture stirred at 100° C. for 30 minutes forming a green precipitate. On cooling to ambient temperature, hexane was added to complete the precipitation. Following filtration and washing with more hexane, complex 43a was isolated as a dark blue powder (0.020 g, 10%).

Complex 43a: FAB mass spectrum, m/z 917 [M-Cl]$^+$; $\square_{eff}$ 5.69 BM.

Example 61

Preparation of [bis-{(6-pyridin-2-yl)pyridin-2-yl-ethyleneamino)-3,5-diisopropylphenyl}-methane] Fe$_2$Cl$_4$ (43b)

Under an atmosphere of nitrogen, anhydrous FeCl$_2$ (0.01 g, 0.08 mmol) was dissolved in n-butanol (2 ml) by stirring at 90° C. for 30 minutes. To this green-yellow solution, 26b (0.03 g, 0.08 mmol) was added and the mixture stirred at 100° C. for 30 minutes forming a green precipitate. On cooling to ambient temperature, hexane was added to complete the precipitation. Following filtration and washing with more hexane, complex 43b was isolated as a dark blue powder (0.01 g, 25%).

Complex 43b: FAB mass spectrum, m/z 980 [M]$^+$, 944 [M-Cl]$^+$, 909 [M-2Cl]$^+$, 853 [M-2Cl—Fe]$^+$, 817 [M-3Cl—Fe]$^+$, IR (cm$^{-1}$) 1591 (C=N).

Formulae for Examples 38-61

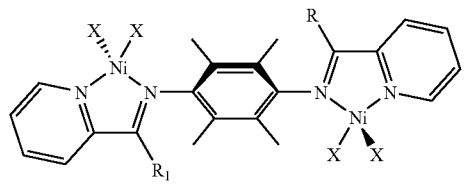

Example 38 (27a) R = R$_1$ = H; X = Br
Example 39 (27b) R = R$_1$ = Me; X = Br
Example 40 (27c) R = H, R$_1$ = Me; X = Br
Example 41 (28) R = R$_1$ = H; X = Cl

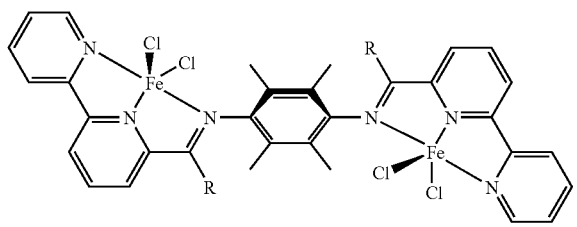

Example 42 (29a) R = H
Example 43 (29b) R = Me

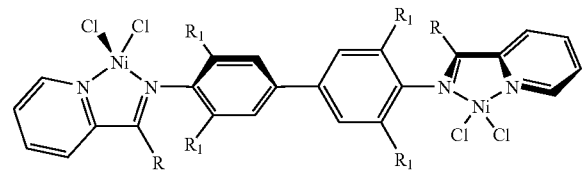

Example 44 (30a) R = H, R$_1$ = Me
Example 45 (30b) R = Me, R$_1$ = Me
Example 46 (31a) R = H, R$_1$ = i-Pr
Example 47 (31b) R = Me, R$_1$ = i-Pr -continued

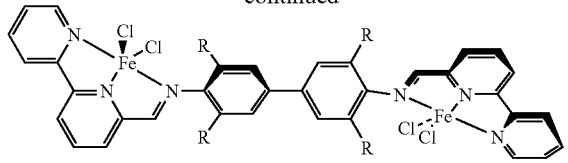

Example 48 (32) R = Me
Example 49 (33) R = i-Pr

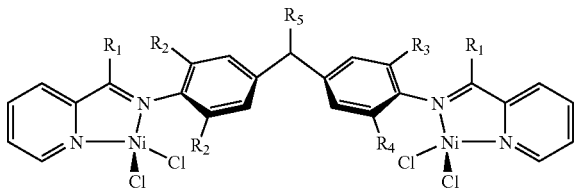

Example 50 (34) R$_1$ = H, R$_2$ = R$_3$ = R$_4$ = Me, R$_5$ = H
Example 51 (35a) R$_1$ = H, R$_2$ = R$_3$ = R$_4$ = i-Pr, R$_5$ = H
Example 52 (35b) R$_1$ = Me, R$_2$ = R$_3$ = R$_4$ = i-Pr, R$_5$ = H
Example 53 (36) R$_1$ = H, R$_2$ = R$_3$ = R$_4$ = i-Pr, R$_5$ = Ph
Example 54 (37) R$_1$ = H, R$_2$ = R$_3$ = R$_4$ = i-Pr, R$_5$ = Ph-4-Br
Example 55 (38) R$_1$ = H, R$_2$ = R$_3$ = R$_4$ = i-Pr, R$_5$ = Ph-4-OH
Example 56 (39) R$_1$ = H, R$_2$ = R$_3$ = R$_4$ = i-Pr, R$_5$ = Ph-4-NO$_2$
Example 57 (40) R$_1$ = H, R$_2$ = R$_3$ = R$_4$ = i-Pr, R$_5$ = Ph-4-i-Pr
Example 58 (41) R$_1$ = H, R$_2$ = i-Pr, R$_3$ = R$_4$ = Me, R$_5$ = H

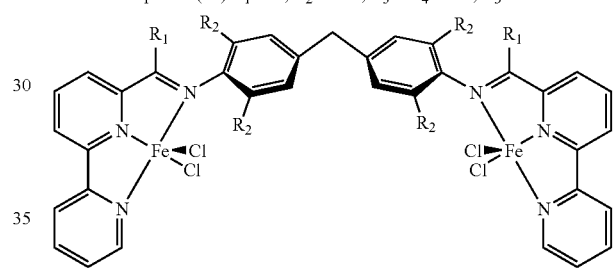

Example 59 (42) R$_1$ = H, R$_2$ = Me
Example 60 (43a) R$_1$ = H, R$_2$ = i-Pr
Example 61 (43b) R$_1$ = Me, R$_2$ = i-Pr Where Ph-4-Br=4-hydroxytoluene, Ph-4-N$_2$=4-nitrotoluene, and Ph-4-i-Pr=4-isopropyltoluene.

Polymerization

The reagents used in the polymerization tests were Ethylene Grade 3.5 (supplied from BOC) and methylaluminoxane (MAO, 10% wt solution in toluene, supplied by Aldrich). GC measurements were obtained using either a Perkin Elmer Autosystem XL chromatogram (University of Leicester) [Column type ZB-5; Column length 30 m; Column diameter 0.25 mm; Initial column temperature 50-100° C.] or with a Mass Spectrometer detector [Perkin Elmer Turbo; Ionisation mode, electron impact; Mass range 50-500 amu; Solvent CH$_2$Cl$_2$]. Differential Scanning Calorimetry (DSC) was performed using a TA Instruments—DSC 2920 model using samples of polyethylene weighing 6±1 mg. The device was calibrated using Indium as a reference standard. Typical scanning conditions are described below:

Heat to 190° C. at 10° C./min
Hold for 1 min at 190° C.
Cool from 190° C. to 20° C. at 10° C./min
Hold for 1 min at 0° C.
Reheat from 0° C. to 190° C. at 10° C./min.

For all the materials one or several peaks are recorded during the heating-cooling-reheating steps.

Some GPC analyses were performed on polyethylene sample using a four Polymer Laboratory mixed B columns installed in the Waters 150C GPC instrument running at a temperature of 135° C., using 1,2,4-trichlorobenzene (TCB) as a mobile phase and monitoring continuously monitor the effluent with a differential refractometer (DRI) and multi angle laser light scattering (MALLS). In other cases, samples were analysed employing a two column mixed B columns installed in the Polymer Laboratory 220 GPC instrument running at a temperature of 160° C., using TCB as a mobile phase and monitoring continuously monitor the effluent with a differential refractometer (DRI).

The results provided by high temperature GPC using the DRI are polystyrene (PS) equivalent molecular weight averages given as $M_n$, $M_w$, and $M_z$. The samples were prepared by dissolving the solid polymers in TCB at 135° C. and removed unsoluble material by filtration.

$^{13}$C NMR spectroscopy were performed using the following procedure. Samples of the polyethylene were dissolved in deuterated TCB (2.5 ml) by heating overnight at 130° C. Deuterated benzene (0.5 ml) was added and the solution was homogenized and reheated to 130° C. prior to the analyses. The instrument used is a Varian Unity Plus 300 using a 10 mm broadband probe at 125° C., with the following acquisition parameters:

Spectral window: 20000 Hz
Acquisition time: 2.0 sec.
Number of points: 80000
Filter band width: not used (oversampling)
Pulse width: 90° pulse
Delay D1: 38 seconds
Number of transients: 1024
Decoupler mode: YYY
Decoupler modulation mode: Waltz
Line broadening: 1

Example 62

Schlenk Tube Polymerization

The complexes (27a, 27b, 27c, 29a, 29b, 31a, 32, 33, 35a, 35b, 36, 37, 38, 39, 42, 43a, 43b) made in the examples above were dissolved or suspended in toluene (40 ml) and MAO introduced. The tube was purged with ethylene and the contents stirred under one bar (100 kPa) of ethylene pressure at 25° C. for the duration of the polymerization. After a predetermined time (see tables), the run was terminated by the addition of aqueous hydrochloric acid. The polymers were filtered and washed with methyl alcohol and dried under reduced pressure at 40° C. overnight.

The filtrate was collected and the organic layer separated and dried over anhydrous magnesium sulfate. The resulting organic phase, containing any oligomeric portion, was prepared for quantitative GC analysis by diluting the solution to 50 ml with toluene in a volumetric flask and adding 1-heptadecene as an internal standard. The runs are summarised in Table 1 showing the distribution of the oligomeric and polymeric portions. Details of oligomer and polymer characterisation are shown in Tables 2-8.

TABLE 1

Ethylene polymerization results from runs 1-17[a]

| Run | Compd (0.010 mmol) | Activator methylalumoxane (mmol/eq.) | Oligomers (g)[b] | Polymers (g) | Activity (g/mmol/h/bar) |
|---|---|---|---|---|---|
| 1 | 27a | 0.01/1000 | 0.77 | 0.32 | 218 |
| 2 | 27b | 0.01/1000 | 1.10 | 0.06 | 231 |
| 3 | 27c | 0.01/1000 | 0.69 | 0.44 | 225 |
| 4 | 29a | 0.0037/368 | 3.435 | 0.562 | 799 |
| 5 | 29b | 0.0037/368 | 0.358 | 0.210 | 114 |
| 6 | 31a | 0.01/1000 | — | 1.23 | 246 |
| 7 | 32 | 0.0037/368 | 2.111 | 0.210 | 464 |
| 8 | 33 | 0.0037/368 | 0.205 | 0.086 | 58 |
| 9 | 34 | 0.004/400 | 1.000 | 0.070 | 214 |
| 10[c] | 35a | 0.003/300 | 1.408 | 0.620 | 220 |
| 11[c] | 35b | 0.003/300 | 1.111 | 0.420 | 153 |
| 12 | 37 | 0.0019/185 | 1.406 | 0.183 | 318 |
| 13 | 38 | 0.0019/185 | 0.211 | 0.425 | 127 |
| 14 | 39 | 0.0019/185 | 0.459 | 0.0630 | 229 |
| 15 | 42 | 0.0019/185 | 1.243 | 0.431 | 335 |
| 16 | 43a | 0.0019/185 | 0.401 | 0.476 | 88 |
| 17[c] | 43b | 0.003/300 | 0.112 | 0.27 | 38 |

[a]General Conditions: Toluene solvent (40 ml), 25° C., reaction time 30 min, ethylene pressure 1 bar (100 kPa), reaction quenched with dilute HCl;
[b]oligomers isolated from polymer filtrate as described above;
[c]reaction time 60 min., other conditions as in footnote a

TABLE 2

Differential scanning calorimetric (DSC) studies for the polymeric portion obtained from runs 1, 3, 4, 5, 7, 9 and 13[a]

| Run | Precatalyst | $T_c$ (° C.) | $T_m$ (° C.) |
|---|---|---|---|
| 1 | 27a | 81.8 | 87.7 |
|   |     | 114.0 | 118.8 |
|   |     |       | 126.4 |
| 3 | 27c | 77.0 | 83.0 |
|   |     | 108.6 | 121.0 |
| 4 | 29a | 122.0 | 107.7 |
|   |     | 84.4 | 76.3 |
| 5 | 29b | 112.1 | 127.2 |
| 7 | 32 | 122.8 | 108.7 |
|   |    | 86.2 | 77.3 |
| 9 | 35a | 68.47 | 74.21 |
|   |     | 104.80 | 116.60 |
| 13 | 38 | 82.4 | 89.3 |
|    |    | 112.68 | 123.43 |

[a]The results displayed above have been obtained following the protocol described in the general polymerisation experimental section and correspond to the crystallization peak $T_c$ and melting peak $T_m$ observed during the reheating of the sample.

Selected polymeric and oligmeric portions of the polyethylene produced by runs 1, 3, 4, 7, 10, 11, 13, 14, 16 and 17 have been analysed using $^1$H and $^{13}$C NMR spectroscopy. The results are displayed in Tables 3, 4 and 5.

TABLE 3

$^1$H NMR spectroscopic data for the oligomeric portion obtained in runs 4, 10, 11, 12, 13, 14, 16, 17[a,b]

| Run | Precat. | —CH=CH$_2$ | —CH=CH— | —CH=C< | >C=CH$_2$ | Additional Me |
|---|---|---|---|---|---|---|
| 4 | 29a | 52.53 | 2.96 | 0.38 | 0.48 | 12 |
| 10 | 35a | 4.14 | 20.4 | 1.71 | 0.06 | 61.02 |
| 11 | 35b | 2.78 | 17.64 | 1.35 | 0.07 | 89.09 |
| 12 | 37 | 6.02 | 20.59 | 1.48 | 0.07 | 52.96 |

TABLE 3-continued $^1$H NMR spectroscopic data for the oligomeric portion obtained in runs 4, 10, 11, 12, 13, 14, 16, 17[a,b]

| Run | Precat. | —CH=CH$_2$ | —CH=CH— | —CH=C< | >C=CH$_2$ | Additional Me |
|---|---|---|---|---|---|---|
| 13 | 38 | 7.65 | 17.25 | 1 | 0.01 | 52.78 |
| 14 | 39 | 6.7 | 19.51 | 1.19 | 0.09 | 61.25 |
| 16 | 43a | 59.89 | 1.61 | 0 | 0.04 | 7.84 |
| 17 | 43b | 57.16 | 2.8 | 0.016 | 0.16 | 10.26 |

[a] per 1000 carbon atoms;
[b] details of the $^1$H NMR spectroscopic procedure are outlined in the general experimental section for the polymerization section.

TABLE 4

$^1$H NMR spectroscopic data for the polymeric portions obtained in runs 1, 3, 10, 11, 13 and 17[a,b]

| Run | Precat. | —CH=CH$_2$ | —CH=CH— | —CH=C< | >C=CH$_2$ | Additional Me |
|---|---|---|---|---|---|---|
| 1 | 27a | 1.93 | 5.41 | 0.31 | 0 | c |
| 3 | 27c | 2.22 | 4.96 | 0.26 | 0 | c |
| 10 | 35a | 1.8 | 7.94 | 0.48 | 0.01 | 36.55 |
| 11 | 35b | 0.94 | 7.68 | 0.47 | 0.03 | 83.4 |
| 13 | 38 | 1.31 | 2.86 | 0.12 | 0.01 | 27.53 |
| 17 | 43b | 7.38 | 0.56 | 0.22 | 0.01 | 1.96 |

[a] per 1000 carbon atoms;
[b] details of the $^1$H NMR spectroscopic procedure are outlined in the general experimental section for the polymerization section;
[c] Not been determined.

TABLE 5

$^{13}$C NMR spectroscopic data for the oligomeric portions obtained in runs 1, 3, 4 and 7[a,b]

| Run | Precatalyst | Methyl | 1,3-diethyl | Hexyl+ | Total |
|---|---|---|---|---|---|
| 1 | 27a | 15.03 | 2.73 | 11.64 | 29.41 |
| 3 | 27c | 22.42 | 2.12 | 5.59 | 30.14 |
| 4 | 29a | 1.80 | | | 1.80 |
| 7 | 32 | 9.0 | | | 9.0 |

[a] per 1000 carbon atoms;
[b] details of the $^{13}$C NMR spectroscopic procedure are outlined in the general experimental section for the polymerization section.

TABLE 6

GC results for the oligomeric portion obtained in runs 1, 2, 3, 4, 5, 7, 8, 15, 16 and 17[a]

| Run | Precatalyst | α (Alpha value) | β (Beta value) |
|---|---|---|---|
| 1 | 27a | 0.91 | 0.09 |
| 2 | 27b | 0.98 | 0.02 |
| 3 | 27c | 0.94 | 0.06 |
| 4 | 29a | 0.96 | 0.04 |
| 5 | 29b | 0.96 | 0.04 |
| 7 | 32 | 0.79 | 0.27 |
| 8 | 33 | 0.90 | 0.11 |
| 15 | 42 | 0.88 | 0.14 |
| 16 | 43a | 0.75 | 0.33 |
| 17 | 43b | 0.56 | 0.79 |

[a] Alpha (α) and Beta (β) values were then determined from GC using extrapolated values based on a Schulz-Flory distribution for C4-C8 and C22-C26 for the oligomers gathered in runs 1, 2, 3, 4, 5, 7, 8, 15, 16 and 17 employing 1-heptadecene as an internal standard. Alpha (α) = n(C$_{n+2}$ olefin)/n(C$_n$ olefin), where n(C$_n$ olefin) is the number of moles of olefin containing n carbon atoms, and n(C$_{n+2}$ olefin) is the number of moles of olefin containing n + 2 carbon atoms, over the sum of the rate of propagation and the rate of chain transfer. Beta (β = (1 − α)/α and is the rate of chain transfer over the rate of propagation.

TABLE 7

GPC data for the oligomeric portions obtained in runs 4, 5, 7, 10, 13, 14, 16 and 17[a]

| Run | Precatalyst | $M_n$ | $M_w$ | $M_z$ | $M_w/M_n$ |
|---|---|---|---|---|---|
| 4 | 29a | 140 | 330 | — | 2.35 |
| 5 | 29b | 120 | 250 | — | 2.08 |
| 7 | 32 | 120 | 200 | — | 1.67 |
| 10 | 35a | 260 | 670 | 1310 | 2.58 |
| 13 | 38 | 230 | 660 | 1640 | 2.87 |
| 14 | 39 | 210 | 610 | 1650 | 2.87 |
| 16 | 43a | 100 | 170 | 260 | 1.7 |
| 17 | 43b | 100 | 160 | 240 | 1.6 |

[a] Mw and Mn were then determined by performing GPC analyses using the Waters GPC instrument on both oligomeric and polymeric portions of the polymers produced in run 4, 5, 7, 10, 13, 14, 16 and 17.

TABLE 8

GPC data for polymeric portion obtained in runs 5, 7, 10, 11, 16 and 17[a]

| Run | Precatalyst | Mn | Mw | Mz | Mw/Mn |
|---|---|---|---|---|---|
| 5 | 29b | 8225 | 16897 | 39919 | 2.35 |
| 7 | 32 | 6286 | 15786 | 60384 | 2.51 |
| 10 | 35a | 1097 | 5571 | 39926 | 5.07 |
| 11 | 35b | 1551 | 2787 | 7505 | 1.79 |
| 16 | 43a | 3348 | 15406 | 85640 | 3.74 |
| 17 | 43b | 1834 | 300801 | 666060 | 16.40 |

[a] Analysed using the Polymer Laboratories GPC instrument using the procedure outlined in the general experimental for the polymerisation section.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

The invention claimed is:

1. A transition metal catalyst compound represented by the formula (I):

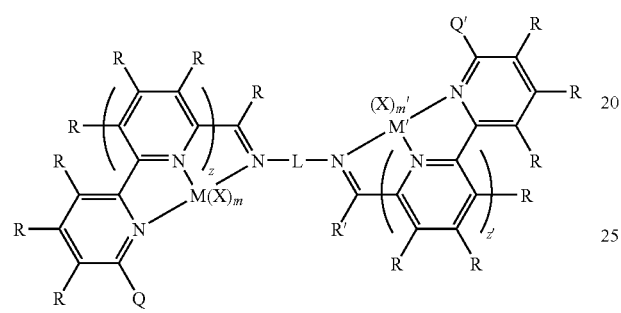

where:
- M and M' are, independently, a group 8, 9, 10 or 11 transition metal;
- each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;
- R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;
- each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;
- m and m' are, independently, 0, 1, 2, or 3;
- z and z' are, independently, 1, 2, or 3;
- N is nitrogen;
- Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;
- Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and
- L is a hydrocarbyl, substituted hydrocarbyl, halocarbyl, substituted halocarbyl, silylcarbyl, substituted silylcarbyl, germylcarbyl, or substituted germylcarbyl substituent, provided however that when M and M' are Ni or M and M' are Pd, then L is selected from the group consisting of aryl groups represented by the formulae:

(3)
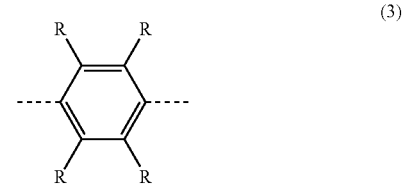

(4)
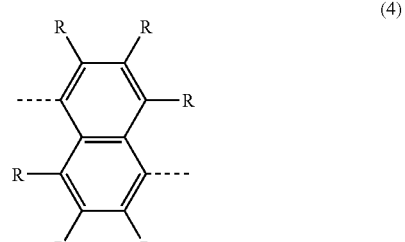

(6)
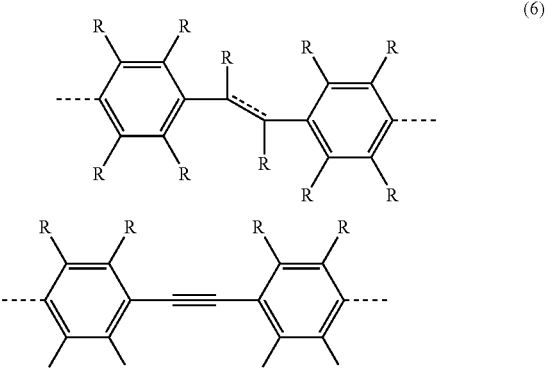

(7)
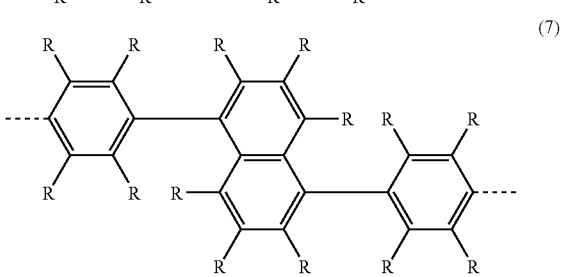

(8)
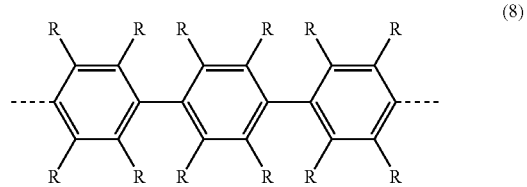

(10)
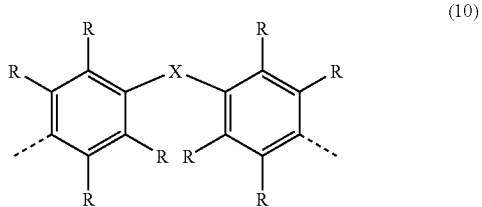

-continued

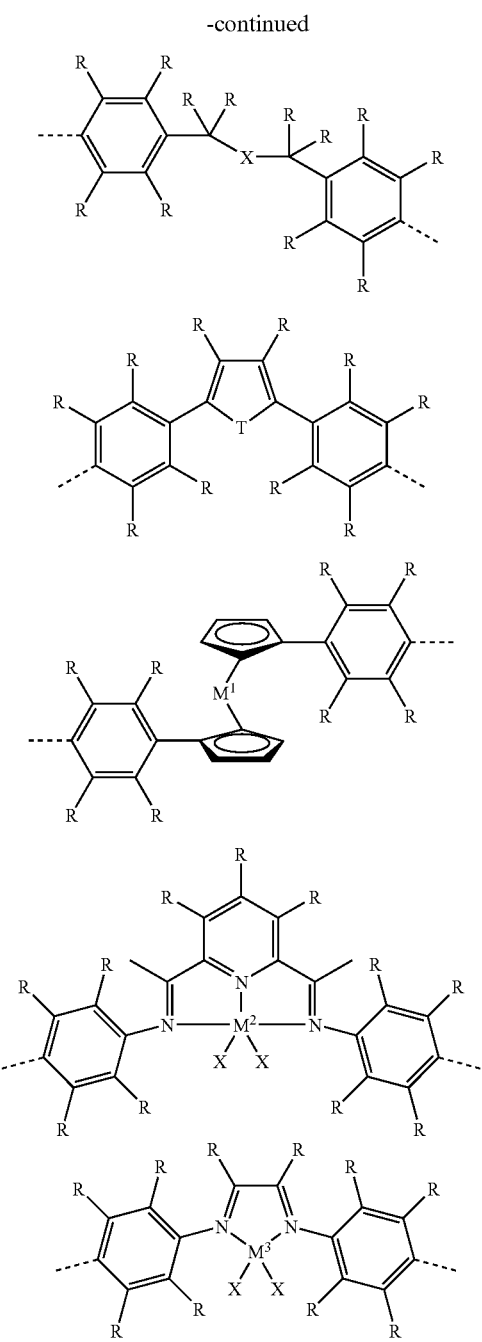

where the dashed lines indicate the bonds to the nitrogen atoms in the formula (I) above, X in formula 14 is O, NR, PR, S, BR, AlR, SiR$_2$;

T=O, NR, BR each R group is in formula 3, 4, 6, 7, 8, 9, 10, 11, 12, 13 and 14, independently, selected from the group consisting of hydrogen, halogen, C1 to C30 hydrocarbyls, and C1 to C30 substituted phenyls;

M$^1$ in formula 13 is a transition metal selected from Groups 4 to 9;

M$^2$ in formula 14 is a transition metal selected from Groups 8 to 11; and

M$^3$ in formula 14 is a transition metal selected from Groups 8 to 11.

2. The compound of claim 1 wherein M and M' are, independently Ni, Co, Fe, Pd or Cu.

3. The compound of claim 1 wherein each R group is, independently, selected from the group consisting of C1 to C20 hydrocarbyls and C1 to C20 substituted phenyls.

4. The compound of claim 1 wherein R' is selected from the group consisting of C1 to C20 hydrocarbyls and C1 to C20 substituted phenyls.

5. The compound of claim 1 wherein each Q and Q' is, independently, selected from the group consisting of C1 to C20 hydrocarbyls and C1 to C20 substituted phenyls.

6. The compound of claim 1 wherein each X is, independently, selected from the group consisting of chlorine, bromine, fluorine, methyl, ethyl, propyl, isopropyl, butyl, t-butyl, pentyl, hexyl, phenyl, and methylphenyl.

7. The compound of claim 1 wherein L is an aryl group.

8. The compound of claim 1 wherein each R, R', Q and Q' is independently selected from the group consisting of hydrogen, methyl, ethyl, isopropyl, and phenyl.

9. A transition metal catalyst compound represented by the formula (I):

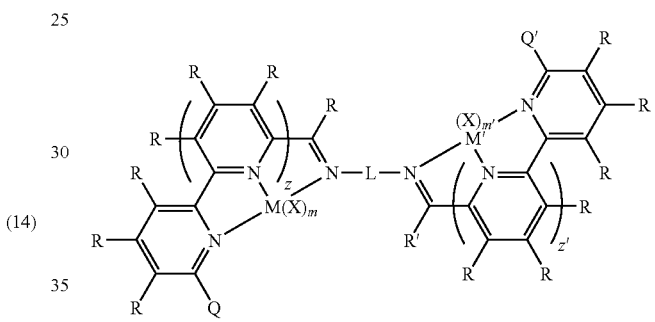

where:

M and M' are, independently, a group 8, 9, 10 or 11 transition metal;

each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;

R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;

each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;

m and m' are, independently, 0, 1, 2, or 3;

z and z' are, independently, 1, 2, or 3;

N is nitrogen;

Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and L is selected from the group consisting of:
1) a monoaryl unit unsubstituted, partially substituted or fully substituted with a number of R substituents on the ring,
2) a fused aryl unit selected from the group consisting of the C10 to C22 fused aromatic hydrocarbyl units, unsubstituted, partially substituted or fully substituted with a number of R substituents on the ring,
3) two aryl units bridged by a substituted or unsubstituted alkyl group, where the aryl units may be unsubstituted, partially substituted or fully substituted with a number of R substituents on the ring,
4) two aryl units bridged by an unsaturated hydrocarbon group, where the aryl units may be unsubstituted, partially substituted or fully substituted with a number of R substituents on the ring,
5) two aryl rings bridged by a fused aryl unit selected from the fused aryl units having ten or more carbon atoms, unsubstituted, partially substituted or fully substituted with a number of R substituents on of the rings,
6) two aryl rings bridged by a polyaryl unit in which the polyaryl unit is selected from the group consisting of one or more aromatic rings, unsubstituted, partially substituted or fully substituted with a number of R substituents on the rings,
7) two aryl rings bridged by a methylene unit in which the methylene unit contains one or two R groups and where the aryl units may be unsubstituted, partially substituted or fully substituted with a number of R substituents on the ring,
8) two diaryl units bridged by a heteroatom X (X=O, NR, PR, S, BR, AlR, SiR$_2$) in which a number of R substituents may be on the heteroatom and where the aryl units may be unsubstituted, partially substituted or fully substituted with a number of R substituents on the ring,
9) two aryl units bridged by a heteroatom or hetroatom-containing fragment X (X'O, NR, PR, S, BR, AlR, SiR$_2$) and one or more hydrocarbon sections, selected from the group consisting of C1 to C30 hydrocarbyls, C1 to C30 substituted phenyls, and where the aryl units may be unsubstituted, partially substituted or fully substituted with a number of R substituents on the ring,
10) two aryl units bridged by one or more 5-, 6- or 7-membered heterocyclic rings containing one or more heteroatoms X (X=O, NR, BR), where the internal rings can be unsubstituted, partially substituted or fully substituted and saturated, partially unsaturated or aromatic,
11) two aryl units bridged by a metallocene section in which the aromatic rings can be unsubstituted, partially substituted or fully substituted with a number of R substituents on the aryl or the cyclopentadienyl and the metal is selected from Group 4 to Group 9 of the Periodic Table, and
12) two aryl units bridged by an α-diimine, a iminopyridine, a bis(imino)pyridine or a polypyridine group coordinated to a metal dihalide where the metal is selected from Group 8 to Group 11 of the Periodic Table, where the imino carbons or the pyridine rings can be unsubstituted, partially substituted or fully substituted with a number of R substituents, and α where the aryl units may be unsubstituted, partially substituted or fully substituted with a number of R substituents on the ring on various positions of the aryl, where each R group is, independently, selected from the group consisting of a hydrogen, a halogen, C1 to C30 hydrocarbyls, and C1 to C30 substituted phenyls.

10. The compound of claim 9 where each R group is, independently, selected from the group consisting of a hydrogen, ethyl, methyl, propyl, butyl, pentyl, hexyl, septyl, octyl, nonyl, decyl, undecyl, dodecyl, phenyl, and methylphenyl.

11. A transition metal catalyst compound represented by the formula (I):

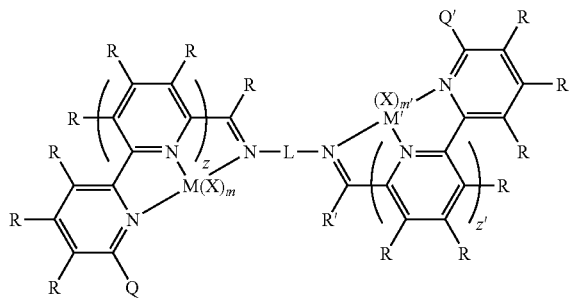

where:
M and M' are, independently, a group 8, 9, 10 or 11 transition metal;
each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;
R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;
each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;
m and m' are, independently, 0, 1, 2, or 3;
z and z' are, independently, 1, 2, or 3;
N is nitrogen;
Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and
L is selected from the group consisting of aryl groups represented by the formulae:
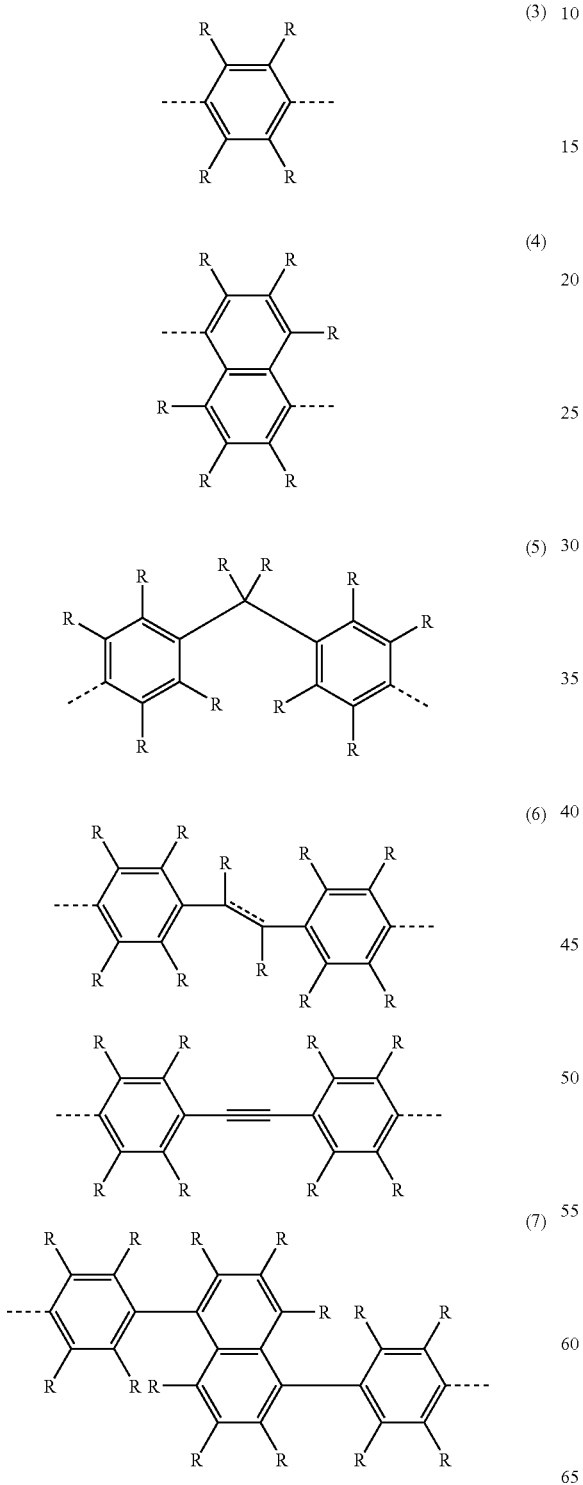
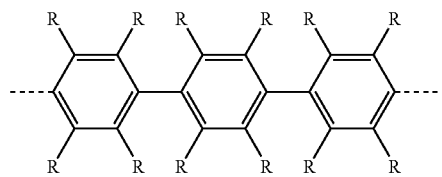
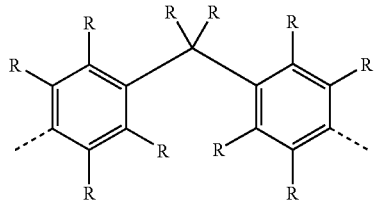
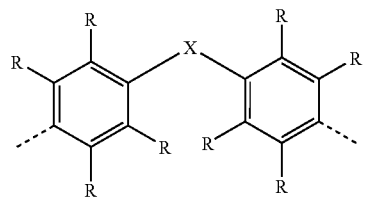
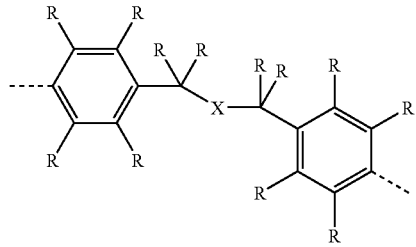
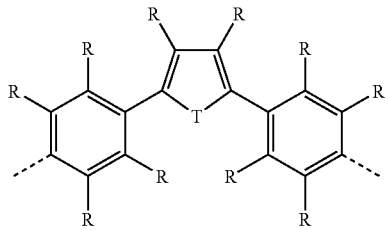
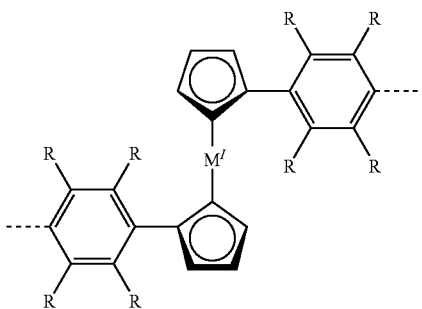

-continued

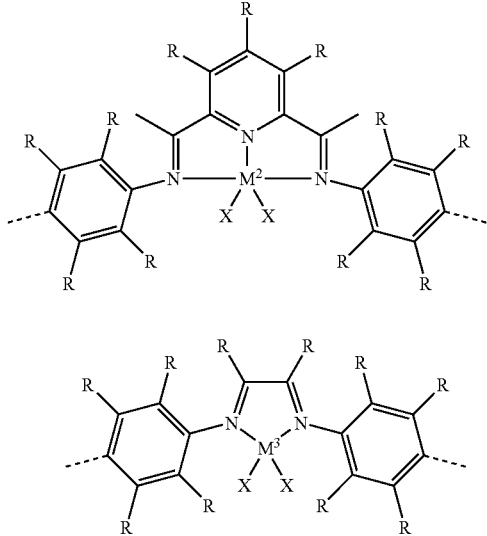

(14)

where the dashed lines indicate the bonds to the nitrogen atoms in the formula in claim 1, X is O, NR, PR, S, BR, AlR, SiR$_2$;

T=O, NR, BR each R group is, independently, selected from the group consisting of hydrogen, halogen, C1 to C30 hydrocarbyls, and C1 to C30 substituted phenyls;

M$^1$ is transition metal selected from Groups 4 to 9;

M$^2$ is transition metal selected from Groups 8 to 11; and

M$^3$ is transition metal selected from Groups 8 to 11.

12. A catalyst system comprising activator and a transition metal catalyst compound represented by the formula (I):

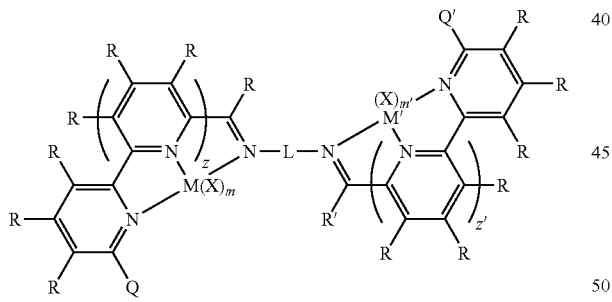

where:

M and M' are, independently, a group 8, 9, 10 or 11 transition metal;

each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;

R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;

each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;

m and m' are, independently, 0, 1, 2, or 3;

z and z' are, independently, 1, 2, or 3;

N is nitrogen;

Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and L is a hydrocarbyl, substituted hydrocarbyl, halocarbyl, substituted halocarbyl, silylcarbyl, substituted silylcarbyl, germylcarbyl, or substituted germylcarbyl substituent, provided however that when M and M' are Ni or M and M' are Pd, then L is selected from the group consisting of aryl groups represented by the formulae:

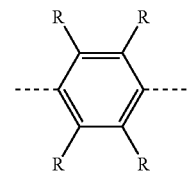

(3)

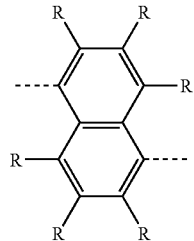

(4)

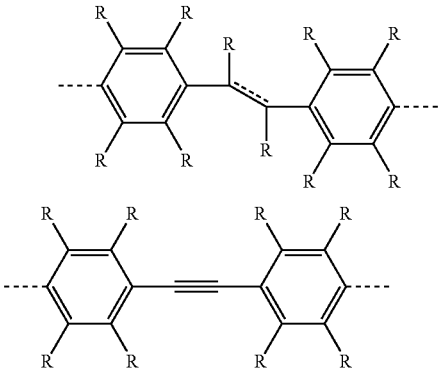

(6)

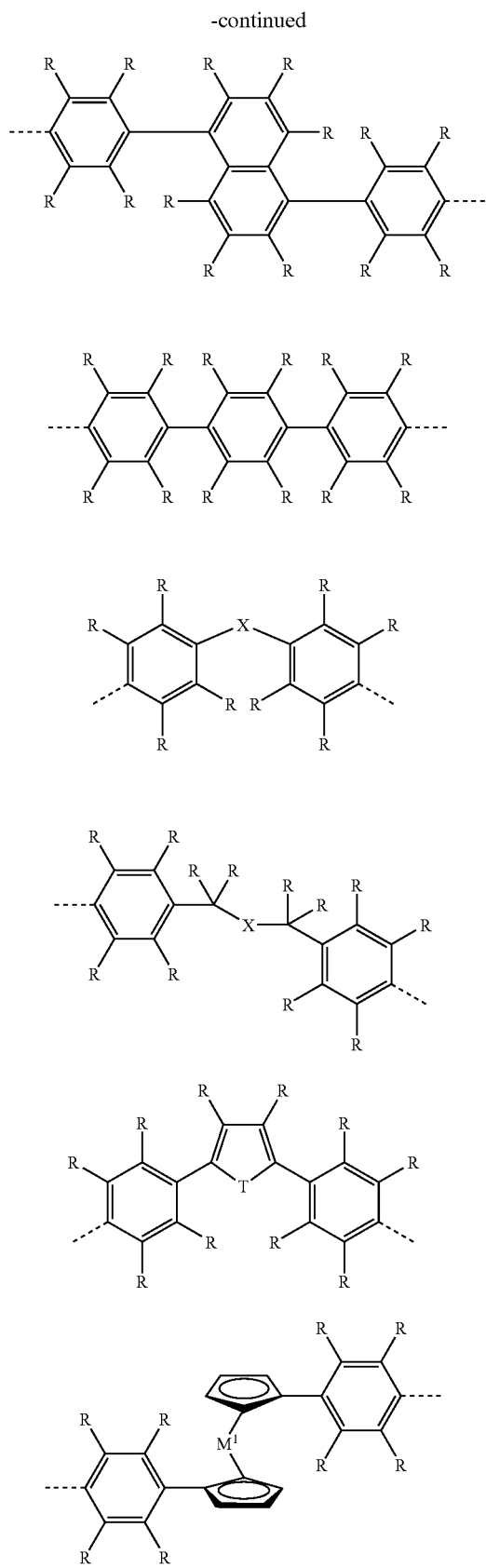

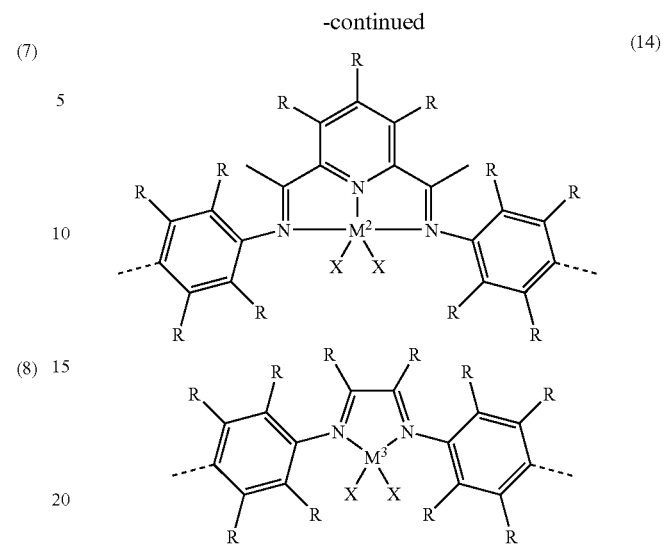

where the dashed lines indicate the bonds to the nitrogen atoms in the formula (I) above, X in formula 14 is O, NR, PR, S, BR, AlR, SiR$_2$;

T=O, NR, BR each R group is in formula 3, 4, 6, 7, 8, 9, 10, 11, 12, 13 and 14, independently, selected from the group consisting of hydrogen, halogen, C1 to C30 hydrocarbyls, and C1 to C30 substituted phenyls;

M$^1$ in formula 13 is a transition metal selected from Groups 4 to 9;

M$^2$ in formula 14 is a transition metal selected from Groups 8 to 11; and

M$^3$ in formula 14 is a transition metal selected from Groups 8 to 11.

13. The catalyst system of claim 12 wherein M and M' are, independently Ni, Co, Pd, Cu or Fe.

14. The catalyst system of claim 12 wherein each R group is, independently, selected from the group consisting of hydrogen, C1 to C20 hydrocarbyls, and C1 to C20 substituted phenyls.

15. The catalyst system of claim 12 wherein R' is selected from the group consisting of hydrogen, C1 to C20 hydrocarbyls, and C1 to C20 substituted phenyls.

16. The catalyst system of claim 12 wherein each Q and Q' is, independently, selected from the group consisting of hydrogen, C1 to C20 hydrocarbyls, and C1 to C20 substituted phenyls.

17. The catalyst system of claim 12 wherein each X is, independently, selected from the group consisting of chlorine, bromine, fluorine, methyl, ethyl, propyl, isopropyl, butyl, t-butyl, pentyl, hexyl, phenyl, and methylphenyl.

18. The catalyst system of claim 12 wherein L comprises an aryl group.

19. The catalyst system of claim 12 wherein each R, R', Q and Q' is independently selected from the group consisting of hydrogen, methyl, ethyl, isopropyl, and phenyl.

20. The catalyst system of claim 12 wherein the activator is an alumoxane.

21. The catalyst system of claim 12 wherein the activator is represented by the following formula:

$$(L^{**}\text{-H})_d^+ (A^{d-})$$

wherein L** is an neutral Lewis base;
H is hydrogen;
(L**-H)+ is a Bronsted acid
$A^{d-}$ is a non-coordinating anion having the charge d–
d is an integer from 1 to 3.

22. The catalyst system of claim 12 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

23. The catalyst system of claim 12 wherein the activator is selected from the group consisting of: N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra(perfluorophenyl)borate.

24. The catalyst system of claim 12 wherein the activator is selected from the group consisting of: methyl alumoxane, modified methyl alumoxane, ethyl alumoxane, iso-butyl alumoxane, triphenyl boron, tris-perfluorophenyl boron, tris-perfluorophenyl aluminum, dimethylanilinium tetrakis perfluorophenyl borate, triphenyl carbonium tetrakis perfluorophenyl borate, dimethylanilinium tetrakis perfluorophenyl aluminate, and trisperfluoronaphthyl boron.

25. A method to polymerize unsaturated monomers comprising contacting one or more monomers with a catalyst system comprising an activator and a transition metal catalyst compound represented by the formula (I):

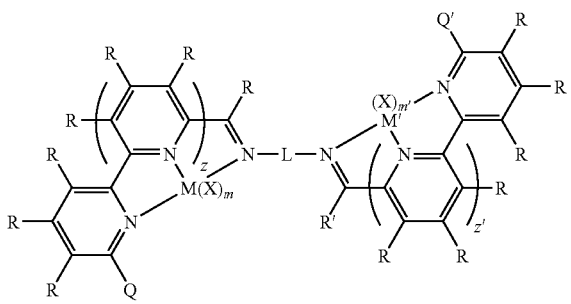

where:
M and M' are, independently, a group 8, 9, 10 or 11 transition metal;
each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;

R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;

each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;

m and m' are, independently, 0, 1, 2, or 3;

z and z' are, independently, 1, 2, or 3;

N is nitrogen;

Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;

Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and L is a hydrocarbyl, substituted hydrocarbyl, halocarbyl, substituted halocarbyl, silylcarbyl, substituted silylcarbyl, germylcarbyl, or substituted germylcarbyl substituent, provided however that when M and M' are Ni or M and M' are Pd, then L is selected from the group consisting of aryl groups represented by the formulae:

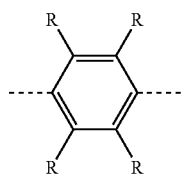

(3)

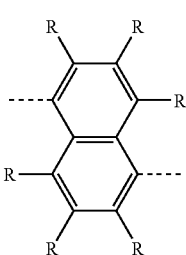

(4)

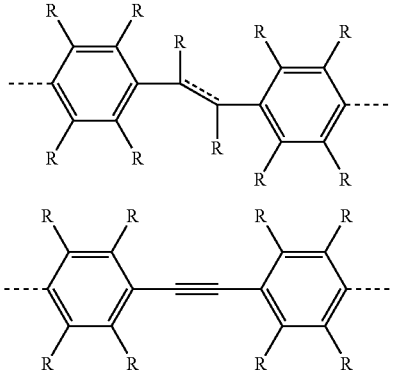

(6)

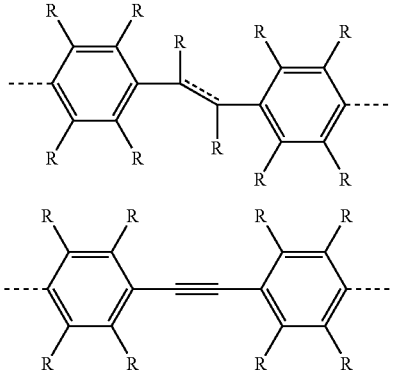

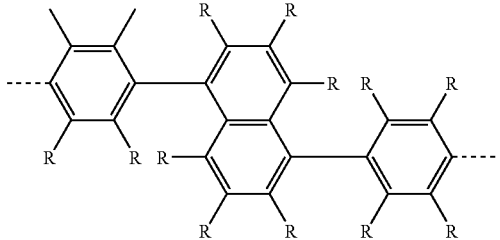

(7)

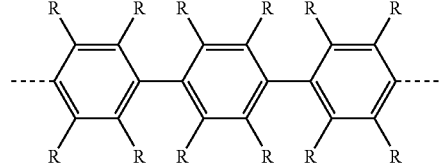

(8)

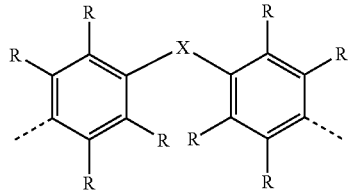

(10)

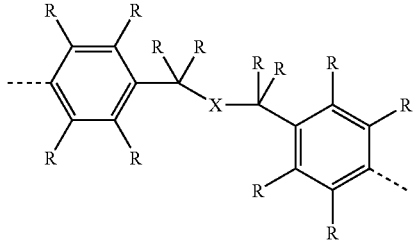

(11)

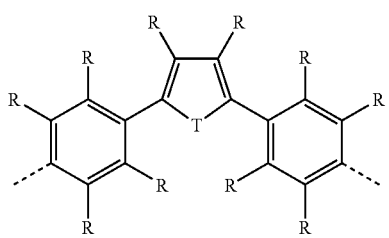

(12)

-continued (13)

(14)

where the dashed lines indicate the bonds to the nitrogen atoms in the formula (I) above, X in formula 14 is O, NR, PR, S, BR, AlR, SiR$_2$;

T=O, NR, BR each R group is in formula 3, 4, 6, 7, 8, 9, 10, 11, 12, 13 and 14, independently, selected from the group consisting of hydrogen, halogen, C1 to C30 hydrocarbyls, and C1 to C30 substituted phenyls;

M$^1$ in formula 13 is a transition metal selected from Groups 4 to 9;

M$^2$ in formula 14 is a transition metal selected from Groups 8 to 11; and

M$^3$ in formula 14 is a transition metal selected from Groups 8 to 11.

26. The method of claim 25 wherein M and M' are, independently Ni, Co or Fe.

27. The method of claim 25 wherein each R group is, independently, selected from the group consisting of C1 to C20 hydrocarbyls, C1 to C20 substituted phenyls, and all isomers thereof.

28. The method of claim 25 wherein R' is selected from the group consisting of C1 to C20 hydrocarbyls, C1 to C20 substituted phenyls, and all isomers thereof.

29. The method of claim 25 wherein each Q and Q' is, independently, selected from the group consisting of C1 to C20 hydrocarbyls, C1 to C20 substituted phenyls, and all isomers thereof.

30. The method of claim 25 wherein each X is, independently, selected from the group consisting of chlorine, bromine, fluorine, methyl, ethyl, propyl, isopropyl, butyl, t-butyl, pentyl, hexyl, phenyl, and methylphenyl.

31. The method of claim 25 wherein L comprises an aryl group.

32. The method of claim 25 wherein each R, R', Q and Q' is independently selected from the group consisting of hydrogen, methyl, ethyl, isopropyl, and phenyl.

33. The method of claim 25 wherein the activator is an alumoxane.

34. The method of claim 25 wherein the activator is represented by the following formula:

$$(L^{**}\text{-}H)_d^+(A^{d-})$$

wherein L** is an neutral Lewis base;

H is hydrogen;

(L**-H)$^+$ is a Bronsted acid

A$^{d-}$ is a non-coordinating anion having the charge d$^-$ d is an integer from 1 to 3.

35. The method of claim 25 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

36. The method of claim 25 wherein the activator is selected from the group consisting of: N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra (perfluorophenyl)borate.

37. The method of claim 25 wherein the activator is selected from the group consisting of: methyl alumoxane, modified methyl alumoxane, ethyl alumoxane, iso-butyl alumoxane, triphenyl boron, tris-perfluorophenyl boron, tris-perfluorophenyl aluminum, dimethylanilinium tetrakis perfluorophenyl borate, triphenyl carbonium tetrakis perfluorophenyl borate, dimethylanilinium tetrakis perfluorophenyl aluminate, and trisperfluoronaphthyl boron.

38. The method of claim 25 wherein the monomer comprises one or more olefins.

39. The method of claim 25 wherein the olefins comprise ethylene.

40. The method of claim 25 wherein the olefins comprises propylene.

41. The method of claim 25 wherein the polymerization occurs in the gas phase.

42. The method of claim 25 wherein the polymerization occurs in the solution phase.

43. The method of claim 25 wherein the polymerization occurs in the slurry phase.

44. The method of claim 25 wherein the polymerization occurs at a temperature above 70° C. and a pressure above 5 MPa.

45. The method of claim 25 wherein the polymerization occurs at a temperature above 70° C. and a pressure above 5 MPa and the monomer comprises propylene.

46. A method to oligomerize an unsaturated monomer comprising contacting one or more monomers with a catalyst system comprising an activator and a transition metal catalyst compound represented by the formula (I):

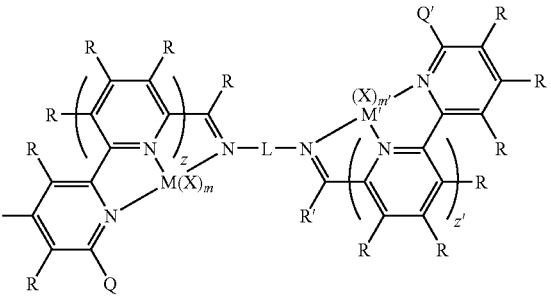

where:
  M and M' are, independently, a group 8, 9, 10 or 11 transition metal;
  each R group is, independently, is, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together to form a substituted or unsubstituted, saturated, partially unsaturated, or aromatic cyclic or polycyclic substituent;
  R' is hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R groups may join together with R' to form a substituted or unsubstituted, saturated, partially unsaturated, or aromatic cyclic or polycyclic substituent;
  each X group is, independently, is, hydrogen, a halogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent X groups may join together to form a substituted or unsubstituted, saturated, partially unsaturated, or aromatic cyclic or polycyclic substituent;
  m and m' are, independently, 0, 1, 2, or 3;
  z and z' are, independently, 1, 2, or 3;
  N is nitrogen;
  Q is hydrogen, or a hydrocarbyl, substituted hydrocarbyl, halocarbyl, substituted halocarbyl, silylcarbyl, substituted silylcarbyl, germylcarbyl, or substituted germylcarbyl substituents;
  Q' is hydrogen, or a hydrocarbyl, substituted hydrocarbyl, halocarbyl, substituted halocarbyl, silylcarbyl, substituted silylcarbyl, germylcarbyl, or substituted germylcarbyl substituents; and
  L is a hydrocarbyl, substituted hydrocarbyl, halocarbyl, substituted halocarbyl, silylcarbyl, substituted silylcarbyl, germylcarbyl, or substituted germylcarbyl substituent, provided however that when M and M' are Ni or M and M' are Pd, then L is selected from the group consisting of aryl groups represented by the formulae:

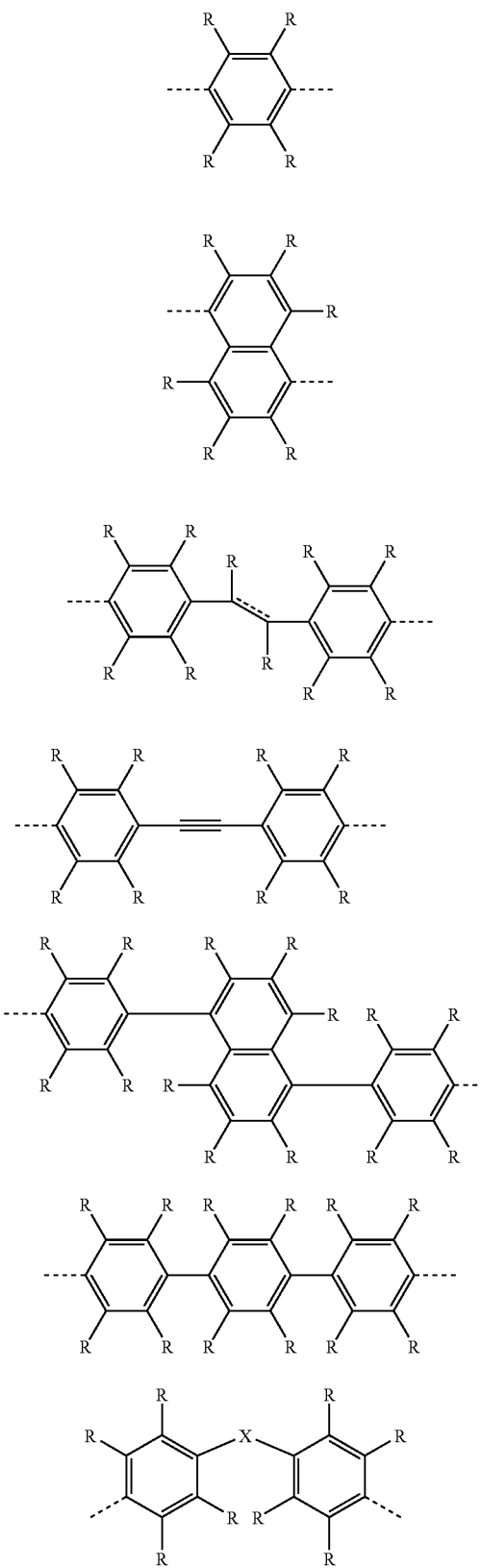
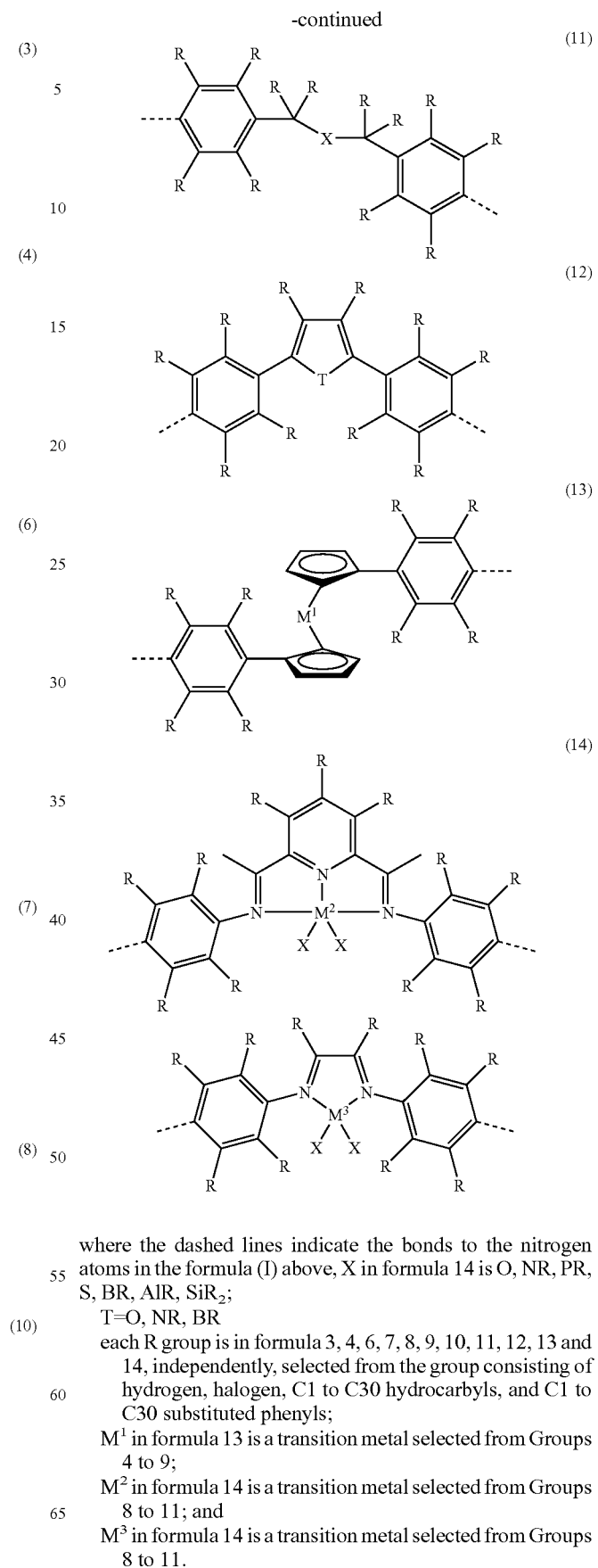

where the dashed lines indicate the bonds to the nitrogen atoms in the formula (I) above, X in formula 14 is O, NR, PR, S, BR, AlR, $SiR_2$;

T=O, NR, BR each R group is in formula 3, 4, 6, 7, 8, 9, 10, 11, 12, 13 and 14, independently, selected from the group consisting of hydrogen, halogen, C1 to C30 hydrocarbyls, and C1 to C30 substituted phenyls;

$M^1$ in formula 13 is a transition metal selected from Groups 4 to 9;

$M^2$ in formula 14 is a transition metal selected from Groups 8 to 11; and $M^3$ in formula 14 is a transition metal selected from Groups 8 to 11.

47. The method of claim 46 wherein M and M' are, independently Ni, Co or Fe.

48. The method of claim 46 wherein each R group is, independently, selected from the group consisting of C1 to C20 hydrocarbyls, C1 to C20 substituted phenyls, and all isomers thereof.

49. The method of claim 46 wherein R' is selected from the group consisting of C1 to C20 hydrocarbyls, C1 to C20 substituted phenyls, and all isomers thereof.

50. The method of claim 46 wherein each Q and Q' is, independently, selected from the group consisting of C1 to C20 hydrocarbyls, C1 to C20 substituted phenyls, and all isomers thereof.

51. The method of claim 46 wherein each X is, independently, selected from the group consisting of chlorine, bromine, fluorine, methyl, ethyl, propyl, isopropyl, butyl, t-butyl, pentyl, hexyl, phenyl, and methylphenyl.

52. The method of claim 46 wherein L comprises an aryl group.

53. The method of claim 46 wherein each R, R', Q and Q' is independently selected from the group consisting of hydrogen, methyl, ethyl, isopropyl, and phenyl.

54. The method of claim 46 wherein the activator is an alumoxane.

55. The method of claim 46 wherein the activator is a non-coordinating anion.

56. The method of claim 46 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

57. The method of claim 46 wherein the monomer comprises one or more olefins.

58. The method of claim 46 wherein the olefins comprise ethylene.

59. The method of claim 46 wherein the olefins comprises propylene.

60. The compound of claim 1 where M and M' are Ni or M and M' are Pd and L is selected from the group consisting of phenyl, 2,5-dimethylphenyl, 2,3,5,6-tetramethylphenyl, naphtalenyl, anthracenyl, phenantracenyl, chrysenelyl, triphenylenyl, 1,1'-(1,2-ethanediyl)bis-benzene, 3,5,3',5'-tetramethyl-1,1'-(1,2-ethanediyl)bis-benzene, 3,5,3',5'-tetraisopropyl-1,1'-(1,2-ethanediyl)bis-benzene, 1,1'-(1,3-propanediyl)bis-benzene, 3,5,3',5'-tetramethyl-1,1'-(1,2-ethanediyl)bis-benzene, 3,5,3',5'-tetraisopropyl-1,1'-(1,3-propanediyl)bis-benzene, 1,1'-(1,2-ethenediyl)bis-benzene, 3,5,3',5'-tetramethyl-(1,2-ethenediyl)bis-benzene, 3,5,3',5'-tetraisopropyl-(1,2-ethenediyl)bis-benzene, 1,1'-(1,2-ethynediyl)bis-benzene, 3,5,3',5'-tetramethyl-1,1'-(1,2-ethynediyl)bis-benzene, 3,5,3',5'-tetraisopropyl-1,1'-(1,2-ethynediyl)bis-benzene, 1,6-diphenyl-naphthalene, 1,6-di-(3,5-dimethylphenyl)-naphthalene, 1,6-di-(3,5- diisopropylphenyl)-naphthalene, 3,6-diphenyl-phenanthrene, 3,6-di-(3,5-dimethylphenyl)-phenanthrene, 3,6-di-(3,5-diisopropyl)-phenanthrene, 1,1'-biphenyl, 3,5,3',5'-tetramethyl-1,1'-biphenyl, 3,5,3',5'-tetraisopropyl-1,1'-biphenyl, [1,1';4',1"]terphenyl, 2,3,5",6"-tetramethyl-[1,1';4',1"]terphenyl, 2,3,5",6"-tetraisopropyl-[1,1';4',1"]terphenyl, 2,3,5,6,2',3',5',6',2",3",5",6"-dodecamethyl-[1,1';4',1"]terphenyl, [1,4';1',1";4",1'"]quaterphenyl, 2,3,5'",6'"-tetradecamethyl-[1,4';1',1";4",1'"]quaterphenyl, 2,3,5'",6'"-tetraisopropyl-[1,4';1',1";4",1'"]quaterphenyl, 2,3,5,6,2',3',5',6',2",3",5",6",2'",3'",5'",6'"-hexadecamethyl-[1,4';1',1";4",1'"]quaterphenyl, 3,5,3'"",5'""-tetra-tert-butyl-[1,1';4',1";4",1'";4'",1''"]quinquephenyl, (4-fluoro-phenyl)-diphenyl-methane, (4-fluoro-phenyl)-di-(3,5-dimethylphenyl)-methane, (4-fluoro-phenyl)-di-(3,5-diisopropylphenyl)-methane, (4-chloro-phenyl)-diphenyl-methane, (4-chloro-phenyl)-di-(3,5-dimethylphenyl)-methane, (4-chloro-phenyl)-di-(3,5-diisopropylphenyl)-methane, (4-bromo-phenyl)-diphenyl-methane, (4-bromo-phenyl)-di-(3,5-dimethylphenyl)-methane, (4-bromo-phenyl)-di-(3,5-diisopropylphenyl)-methane, 4-[diphenyl-methyl]-benzaldehyde, 4-[bis-(3,5-dimethyl-phenyl)-methyl]-benzaldehyde, 4-[bis-(3,5-diisopropyl-phenyl)-methyl]-benzaldehyde, 4-[diphenyl-methyl]-phenol, 4-[bis-(3,5-dimethyl-phenyl)-methyl]-phenol, 4-[bis-(3,5-diisopropyl-phenyl)-methyl]-phenol, 4-[diphenyl-methyl]-thiophenol, 4-[bis-(3,5-dimethyl-phenyl)-methyl]-thiophenol, 4-[bis-(3,5-diisopropyl-phenyl)-methyl]-thiophenol, 4-[diphenyl-methyl]-benzoic acid, 4-[bis-(3,5-dimethyl-phenyl)-methyl]-benzoic acid, 4-[bis-(3,5-diisopropyl-phenyl)-methyl]-benzoic acid, 4-[diphenyl-methyl]-nitro-benzene, 4-[bis-(3,5-dimethyl-phenyl)-methyl]-nitro-benzene, 4-[bis-(3,5-diisopropyl-phenyl)-methyl]-nitro-benzene, 4-[diphenyl-methyl]-benzenamine, 4-[bis-(3,5-dimethyl-phenyl)-methyl]-benzenamine, 4-[bis-(3,5-diisopropyl-phenyl)-methyl]-benzenamine, diphenyl-ether, bis-(3,5-dimethyl-phenyl)-ether, bis-(3,5-diisopropyl-phenyl)-ether, diphenyl-amine, bis-(3,5-dimethyl-phenyl)-amine, bis-(3,5-diisopropyl-phenyl)-amine, diphenyl-phosphine, bis-(3,5-dimethyl-phenyl)-phosphine, bis-(3,5-diisopropyl-phenyl)-phosphine, diphenyl sulfide, bis-(3,5-dimethyl-phenyl)-sulfide, bis-(3,5-diisopropyl-phenyl)-sulfide, methyl-diphenyl-borane, methyl-bis-(3,5-dimethyl-phenyl)-borane, methyl-bis-(3,5-diisopropyl-phenyl)-borane, methyl-diphenyl-aluminium, methyl-bis-(3,5-dimethyl-phenyl)-aluminium, methyl-bis-(3,5-diisopropyl-phenyl)-aluminium, dimethyl-diphenyl-silane, dimethyl-bis-(3,5-dimethyl-phenyl)-silane, dimethyl-bis-(3,5-diisopropyl-phenyl)-silane, 2,5-diphenyl-pyrrole, 2,5-bis-(3,5-dimethyl-phenyl)-pyrrole, 2,5-bis-(3,5-diisopropyl-phenyl)-pyrrole, 2,5-diphenyl-furan, 2,5-bis-(3,5-dimethyl-phenyl)-furan, 2,5-bis-(3,5-diisopropyl-phenyl)-furan, 2,6-diphenyl-pyridine, 2,6-bis-(3,5-dimethyl-phenyl)-pyridine, 2,6-bis-(3,5-diisopropyl-phenyl)-pyridine diphenylferrocene, Bis-(imino)-pyridin-iron-dichloride, Bis-(imino)-pyridin-iron-dibromide, [2,2';6',2"]terpyridine-iron-dichloride, [2,2';6',2"]terpyridine-iron-dibromide, Bis-(imino)-pyridin-cobalt-dichloride, Bis-(imino)-pyridin-cobalt-dibromide, [2,2';6',2"]terpyridine-cobalt-dichloride, [2,2';6',2"]terpyridine-cobalt-dibromide, ethane-1,2-diylidenediamine-nickel-dichloride, ethane-1,2-diylidenediamine-nickel-dibromide, ethane-1,2-diylidenediamine-palladium-dichloride, ethane-1,2-diylidenediamine-palladium-dibromide, ethane-1,2-diylidenediamine-copper-dichloride, ethane-1,2-diylidenediamine-copper-dibromide, ethane-1,2-dimethyl-1,2-diylidenediamine-nickel-dichloride, ethane-1,2-dimethyl-1,2-diylidenediamine-nickel-dibromide, ethane-1,2-dimethyl-1,2-diylidenediamine-palladium-dichloride, ethane-1,2-dimethyl-1,2-diylidenediamine-palladium-dibromide, ethane-1,2-dimethyl-1,2-diylidenediamine-copper-dichloride, and ethane-1,2-dimethyl-1,2-diylidenediamine-copper-dibromide.

61. The compound of claim 12 where M and M' are Ni or M and M' are Pd and L is selected from the group consisting of phenyl, 2,5-dimethylphenyl, 2,3,5,6-tetramethylphenyl, naphtalenyl, anthracenyl, phenantracenyl, chrysenelyl, triphenylenyl, 1,1'-(1,2-ethanediyl)bis-benzene, 3,5,3',5'-tetramethyl-1,1'-(1,2-ethanediyl)bis-benzene, 3,5,3',5'-tetraisopropyl-1,1'-(1,2-ethanediyl)bis-benzene, 1,1'-(1,3-propanediyl)bis-benzene, 3,5,3',5'-tetramethyl-1,1'-(1,2-ethanediyl)bis-benzene, 3,5,3',5'-tetraisopropyl-1,1'-(1,3-propanediyl)bis-benzene, 1,1'-(1,2-ethenediyl)bis-benzene, 3,5,3',5'-tetramethyl-(1,2-ethenediyl)bis-benzene, 3,5,3',5'-tetraisopropyl-(1,2-ethenediyl)bis-benzene, 1,1'-(1,2-ethynediyl)bis-benzene, 3,5,3',5'-tetramethyl-1,1'-(1,2-ethynediyl)bis-benzene, 3,5,3',5'-tetraisopropyl-1,1'-(1,2-ethynediyl)bis-benzene, 1,6-diphenyl-naphthalene, 1,6-di-(3,5-dimethylphenyl)-naphthalene, 1,6-di-(3,5-diisopropylphenyl)-naphthalene, 3,6-diphenyl-phenanthrene, 3,6-di-(3,5-dimethylphenyl)-phenanthrene, 3,6-di-(3,5-diisopropyl)-phenanthrene, 1,1'-biphenyl, 3,5,3',5'-tetramethyl-1,1'-biphenyl, 3,5,3',5'-tetraisopropyl-1,1'-biphenyl, [1,1';4',1"]terphenyl, 2,3,5",6"-tetramethyl-[1,1';4',1"]terphenyl, 2,3,5",6"-tetraisopropyl-[1,1';4',1"]terphenyl, 2,3,5,6,2',3',5',6',2",3",5",6"-dodecamethyl-[1,1';4',1"]terphenyl, [1,4';1',1";4",1'"]quaterphenyl, 2,3,5'",6'"-tetradecamethyl-[1,4';1',1";4",1'"]quaterphenyl, 2,3,5'",6'"-tetraisopropyl-[1,4';1',1";4",1'"]quaterphenyl, 2,3,5,6,2',3',5',6',2",3",5",6",2'",3'",5'",6'"-hexadecamethyl-[1,4';1',1";4",1'"]quaterphenyl, 3,5,3'"",5'""-tetra-tert-butyl-[1,1';4',1";4",1'";4'",1''"]quinquephenyl, (4-fluoro-phenyl)-diphenyl-methane, (4-fluoro-phenyl)-di-(3,5-dimethylphenyl)-methane, (4-fluoro-phenyl)-di-(3,5-diisopropylphenyl)-methane, (4-chloro-phenyl)-diphenyl-methane, (4-chloro-phenyl)-di-(3,5-dimethylphenyl)-methane, (4-chloro-phenyl)-di-(3,5-diisopropylphenyl)-methane, (4-bromo-phenyl)-diphenyl-methane, (4-bromo-phenyl)-di-(3,5-dimethylphenyl)-methane, (4-bromo-phenyl)-di-(3,5-diisopropylphenyl)-methane, 4-[diphenyl-methyl]-benzaldehyde, 4-[bis-(3,5-dimethyl-phenyl)-methyl]-benzaldehyde, 4-[bis-(3,5-diisopropyl-phenyl)-methyl]-benzaldehyde, 4-[diphenyl-methyl]-phenol, 4-[bis-(3,5-dimethyl-phenyl)-methyl]-phenol, 4-[bis-(3,5-diisopropyl-phenyl)-methyl]-phenol, 4-[diphenyl-methyl]-thiophenol, 4-[bis-(3,5-dimethyl-phenyl)-methyl]-thiophenol, 4-[bis-(3,5-diisopropyl-phenyl)-methyl]-thiophenol, 4-[diphenyl-methyl]-benzoic acid, 4-[bis-(3,5-dimethyl-phenyl)-methyl]-benzoic acid, 4-[bis-(3,5-diisopropyl-phenyl)-methyl]-benzoic acid, 4-[diphenyl-methyl]-nitro-benzene, 4-[bis-(3,5-dimethyl-phenyl)-methyl]-nitro-benzene, 4-[bis-(3,5-diisopropyl-phenyl)-methyl]-nitro-benzene, 4-[diphenyl-methyl]-benzenamine, 4-[bis-(3,5-dimethyl-phenyl)-methyl]-benzenamine, 4-[bis-(3,5-diisopropyl-phenyl)-methyl]-benzenamine, diphenyl-ether, bis-(3,5-dimethyl-phenyl)-ether, bis-(3,5-diisopropyl-phenyl)-ether, diphenyl-amine, bis-(3,5-dimethyl-phenyl)-amine, bis-(3,5-diisopropyl-phenyl)-amine, diphenyl-phosphine, bis-(3,5-dimethyl-phenyl)-phosphine, bis-(3,5-diisopropyl-phenyl)-phosphine, diphenyl sulfide, bis-(3,5-dimethyl-phenyl)-sulfide, bis-(3,5-diisopropyl-phenyl)-sulfide, methyl-diphenyl-borane, methyl-bis-(3,5-dimethyl-phenyl)-borane, methyl-bis-(3,5-diisopropyl-phenyl)-borane, methyl-diphenyl-aluminium, methyl-bis-(3,5-dimethyl-phenyl)-aluminium, methyl-bis-(3,5-diisopropyl-phenyl)-aluminium, dimethyl-diphenyl-silane, dimethyl-bis-(3,5-dimethyl-phenyl)-silane, dimethyl-bis-(3,5- diisopropyl-phenyl)-silane, 2,5-diphenyl-pyrrole, 2,5-bis-(3,5-dimethyl-phenyl)-pyrrole, 2,5-bis-(3,5-diisopropyl-phenyl)-pyrrole, 2,5-diphenyl-furan, 2,5-bis-(3,5-dimethyl-phenyl)-furan, 2,5-bis-(3,5-diisopropyl-phenyl)-furan, 2,6-diphenyl-pyridine, 2,6-bis-(3,5-dimethyl-phenyl)-pyridine, 2,6-bis-(3,5-diisopropyl-phenyl)-pyridine diphenylferrocene, Bis-(imino)-pyridin-iron-dichloride, Bis-(imino)-pyridin-iron-dibromide, [2,2';6',2"]terpyridine-iron-dichloride, [2,2';6',2"]terpyridine-iron-dibromide, Bis-(imino)-pyridin-cobalt-dichloride, Bis-(imino)-pyridin-cobalt-dibromide, [2,2';6',2"]terpyridine-cobalt-dichloride, [2,2';6',2"']terpyridine-cobalt-dibromide, ethane-1,2-diylidenediamine-nickel-dichloride, ethane-1,2-diylidenediamine-nickel-dibromide, ethane-1,2-diylidenediamine-palladium-dichloride, ethane-1,2-diylidenediamine-palladium-dibromide, ethane-1,2-diylidenediamine-copper-dichloride, ethane-1,2-diylidenediamine-copper-dibromide, ethane-1,2-dimethyl-1,2-diylidenediamine-nickel-dichloride, ethane-1,2-dimethyl-1,2-diylidenediamine-nickel-dibromide, ethane-1,2-dimethyl-1,2-diylidenediamine-palladium-dichloride, ethane-1,2-dimethyl-1,2-diylidenediamine-palladium-dibromide, ethane-1,2-dimethyl-1,2-diylidenediamine-copper-dichloride, and ethane-1,2-dimethyl-1,2-diylidenediamine-copper-dibromide.

62. The compound of claim 25 where M and M' are Ni or M and M' are Pd and L is selected from the group consisting of phenyl, 2,5-dimethylphenyl, 2,3,5,6-tetramethylphenyl, naphtalenyl, anthracenyl, phenantracenyl, chrysenelyl, triphenylenyl, 1,1'-(1,2-ethanediyl)bis-benzene, 3,5,3',5'-tetramethyl-1,1'-(1,2-ethanediyl)bis-benzene, 3,5,3',5'-tetraisopropyl-1,1'-(1,2-ethanediyl)bis-benzene, 1,1'-(1,3-propanediyl)bis-benzene, 3,5,3',5'-tetramethyl-1,1'-(1,2-ethanediyl)bis-benzene, 3,5,3',5'-tetraisopropyl-1,1'-(1,3-propanediyl)bis-benzene, 1,1'-(1,2-ethenediyl)bis-benzene, 3,5,3',5'-tetramethyl-(1,2-ethenediyl)bis-benzene, 3,5,3',5'-tetraisopropyl-(1,2-ethenediyl)bis-benzene, 1,1'-(1,2-ethynediyl)bis-benzene, 3,5,3',5'-tetramethyl-1,1'-(1,2-ethynediyl)bis-benzene, 3,5,3',5'-tetraisopropyl-1,1'-(1,2-ethynediyl)bis-benzene, 1,6-diphenyl-naphthalene, 1,6-di-(3,5-dimethylphenyl)-naphthalene, 1,6-di-(3,5-diisopropylphenyl)-naphthalene, 3,6-diphenyl-phenanthrene, 3,6-di-(3,5-dimethylphenyl)-phenanthrene, 3,6-di-(3,5-diisopropyl)-phenanthrene, 1,1'-biphenyl, 3,5,3',5'-tetramethyl-1,1'-biphenyl, 3,5,3',5'-tetraisopropyl-1,1'-biphenyl, [1,1';4',1"]terphenyl, 2,3,5",6"-tetramethyl-[1,1';4',1"]terphenyl, 2,3,5"',6""-tetraisopropyl-[1,1';4',1"]terphenyl, 2,3,5,6,2',3',5',6',2",3",5",6"-dodecamethyl-[1,1';4',1"]terphenyl, [1,4';1',1";4",1'"]quaterphenyl, 2,3,5'",6'"-tetradecamethyl-[1,4';1',1";4",1'"]quaterphenyl, 2,3,5'",6'"-tetraisopropyl-[1,4';1',1";4",1'"]quaterphenyl, 2,3,5,6,2',3',5',6',2",3",5",6",2'",3'",5'",6'"-hexadecamethyl-[1,4';1',1";4",1'"]quaterphenyl, 3,5,3"",5""-tetra-tert-butyl-[1,1';4',1";4",1'";4''',1""]quinquephenyl, (4-fluoro-phenyl)-diphenyl-methane, (4-fluoro-phenyl)-di-(3,5-dimethylphenyl)-methane, (4-fluoro-phenyl)-di-(3,5-diisopropylphenyl)-methane, (4-chloro-phenyl)-diphenyl-methane, (4-chloro-phenyl)-di-(3,5-dimethylphenyl)-methane, (4-chloro-phenyl)-di-(3,5-diisopropylphenyl)-methane, (4-bromo-phenyl)-diphenyl-methane, (4-bromo-phenyl)-di-(3,5-dimethylphenyl)-methane, (4-bromo-phenyl)-di-(3,5-diisopropylphenyl)-methane, 4-[diphenyl-methyl]-benzaldehyde, 4-[bis-(3,5-dimethyl-phenyl)-methyl]-benzaldehyde, 4-[bis-(3,5-diisopropyl-phenyl)-methyl]-benzaldehyde, 4-[diphenyl-methyl]-phenol, 4-[bis-(3,5-dimethyl-phenyl)-methyl]-phenol, 4-[bis-(3,5-diisopropyl-phenyl)-methyl]-phenol, 4-[diphenyl-methyl]-thiophenol, 4-[bis-(3,5-dimethyl-phenyl)-methyl]-thiophenol, 4-[bis-(3,5-diisopropyl-phenyl)-methyl]-thiophenol, 4-[diphenyl-methyl]-benzoic acid, 4-[bis-(3,5-dimethyl-phenyl)-methyl]-benzoic acid, 4-[bis-(3,5-diisopropyl-phenyl)-methyl]-benzoic acid, 4-[diphenyl-methyl]-nitro-benzene, 4-[bis-(3,5-dimethyl-phenyl)-methyl]-nitro-benzene, 4-[bis-(3,5-diisopropyl-phenyl)-methyl]-nitro-benzene, 4-[diphenyl-methyl]-benzenamine, 4-[bis-(3,5-dimethyl-phenyl)-methyl]-benzenamine, 4-[bis-(3,5-diisopropyl-phenyl)-methyl]-benzenamine, diphenyl-ether, bis-(3,5-dimethyl-phenyl)-ether, bis-(3,5-diisopropyl-phenyl)-ether, diphenyl-amine, bis-(3,5-dimethyl-phenyl)-amine, bis-(3,5-diisopropyl-phenyl)-amine, diphenyl-phosphine, bis-(3,5-dimethyl-phenyl)-phosphine, bis-(3,5-diisopropyl-phenyl)-phosphine, diphenyl sulfide, bis-(3,5-dimethyl-phenyl)-sulfide, bis-(3,5-diisopropyl-phenyl)-sulfide, methyl-diphenyl-borane, methyl-bis-(3,5-dimethyl-phenyl)-borane, methyl-bis-(3,5-diisopropyl-phenyl)-borane, methyl-diphenyl-aluminium, methyl-bis-(3,5-dimethyl-phenyl)-aluminium, methyl-bis-(3,5-diisopropyl-phenyl)-aluminium, dimethyl-diphenyl-silane, dimethyl-bis-(3,5-dimethyl-phenyl)-silane, dimethyl-bis-(3,5-diisopropyl-phenyl)-silane, 2,5-diphenyl-pyrrole, 2,5-bis-(3,5-dimethyl-phenyl)-pyrrole, 2,5-bis-(3,5-diisopropyl-phenyl)-pyrrole, 2,5-diphenyl-furan, 2,5-bis-(3,5-dimethyl-phenyl)-furan, 2,5-bis-(3,5-diisopropyl-phenyl)-furan, 2,6-diphenyl-pyridine, 2,6-bis-(3,5-dimethyl-phenyl)-pyridine, 2,6-bis-(3,5-diisopropyl-phenyl)-pyridine diphenylferrocene, Bis-(imino)-pyridin-iron-dichloride, Bis-(imino)-pyridin-iron-dibromide, [2,2';6',2"]terpyridine-iron-dichloride, [2,2';6',2"]terpyridine-iron-dibromide, Bis-(imino)-pyridin-cobalt-dichloride, Bis-(imino)-pyridin-cobalt-dibromide, [2,2';6',2"]terpyridine-cobalt-dichloride, [2,2';6',2"]terpyridine-cobalt-dibromide, ethane-1,2-diylidenediamine-nickel-dichloride, ethane-1,2-diylidenediamine-nickel-dibromide, ethane-1,2-diylidenediamine-palladium-dichloride, ethane-1,2-diylidenediamine-palladium-dibromide, ethane-1,2-diylidenediamine-copper-dichloride, ethane-1,2-diylidenediamine-copper-dibromide, ethane-1,2-dimethyl-1,2-diylidenediamine-nickel-dichloride, ethane-1,2-dimethyl-1,2-diylidenediamine-nickel-dibromide, ethane-1,2-dimethyl-1,2-diylidenediamine-palladium-dichloride, ethane-1,2-dimethyl-1,2-diylidenediamine-palladium-dibromide, ethane-1,2-dimethyl-1,2-diylidenediamine-copper-dichloride, and ethane-1,2-dimethyl-1,2-diylidenediamine-copper-dibromide.

63. The compound of claim 46 where M and M' are Ni or M and M' are Pd and L is selected from the group consisting of phenyl, 2,5-dimethylphenyl, 2,3,5,6-tetramethylphenyl, naphtalenyl, anthracenyl, phenantracenyl, chrysenelyl, triphenylenyl, 1,1'-(1,2-ethanediyl)bis-benzene, 3,5,3',5'-tetramethyl-1,1'-(1,2-ethanediyl)bis-benzene, 3,5,3',5'-tetraisopropyl-1,1'-(1,2-ethanediyl)bis-benzene, 1,1'-(1,3-propanediyl)bis-benzene, 3,5,3',5'-tetramethyl-1,1'-(1,2-ethanediyl)bis-benzene, 3,5,3',5'-tetraisopropyl-1,1'-(1,3-propanediyl)bis-benzene, 1,1'-(1,2-ethenediyl)bis-benzene, 3,5,3',5'-tetramethyl-(1,2-ethenediyl)bis-benzene, 3,5,3',5'-tetraisopropyl-(1,2-ethenediyl)bis-benzene, 1,1'-(1,2-ethynediyl)bis-benzene, 3,5,3',5'-tetramethyl-1,1'-(1,2-ethynediyl)bis-benzene, 3,5,3',5'-tetraisopropyl-1,1'-(1,2-ethynediyl)bis-benzene, 1,6-diphenyl-naphthalene, 1,6-di-(3,5-dimethylphenyl)-naphthalene, 1,6-di-(3,5-diisopropylphenyl)-naphthalene, 3,6-diphenyl-phenanthrene, 3,6-di-(3,5-dimethylphenyl)-phenanthrene, 3,6-di-(3,5-diisopropyl)-phenanthrene, 1,1'-biphenyl, 3,5,3',5'-tetramethyl-1,1'-biphenyl, 3,5,3',5'-tetraisopropyl-1,1'-biphenyl, [1,1';4',1"]terphenyl, 2,3,5",6"-tetramethyl-[1,1';4',1"]terphenyl, 2,3,5",6"-tetraisopropyl-[1,1';4',1"]terphenyl, 2,3,5,6,2',3',5',6',2",3",5",6"-dodecamethyl-[1,1';4',1"]terphenyl, [1,4';1',1";4",1"']quaterphenyl, 2,3,5"',6"'-tetradecamethyl-[1,4';1',1";4",1"']quaterphenyl, 2,3,5"',6"'-tetraisopropyl-[1,4';1',1";4",1"']quaterphenyl, 2,3,5,6,2',3',5',6',2", 3",5",6",2"',3"',5"',6"'-hexadecamethyl-[1,4';1',1";4",1"'] quaterphenyl, 3,5,3"",5""-tetra-tert-butyl-[1,1';4',1";4",1"'; 4"',1""]quinquephenyl, (4-fluoro-phenyl)-diphenyl-methane, (4-fluoro-phenyl)-di-(3,5-dimethylphenyl)-methane, (4-fluoro-phenyl)-di-(3,5-diisopropylphenyl)-methane, (4-chloro-phenyl)-diphenyl-methane, (4-chloro-phenyl)-di-(3,5-dimethylphenyl)-methane, (4-chloro-phenyl)-di-(3,5-diisopropylphenyl)-methane, (4-bromo-phenyl)-diphenyl-methane, (4-bromo-phenyl)-di-(3,5-dimethylphenyl)-methane, (4-bromo-phenyl)-di-(3,5-diisopropylphenyl)-methane, 4-[diphenyl-methyl]-benzaldehyde, 4-[bis-(3,5-dimethyl-phenyl)-methyl]-benzaldehyde, 4-[bis-(3,5-diisopropyl-phenyl)-methyl]-benzaldehyde, 4-[diphenyl-methyl]-phenol, 4-[bis-(3,5-dimethyl-phenyl)-methyl]-phenol, 4-[bis-(3,5-diisopropyl-phenyl)-methyl]-phenol, 4-[diphenyl-methyl]-thiophenol, 4-[bis-(3,5-dimethyl-phenyl)-methyl]-thiophenol, 4-[bis-(3,5-diisopropyl-phenyl)-methyl]-thiophenol, 4-[diphenyl-methyl]-benzoic acid, 4-[bis-(3,5-dimethyl-phenyl)-methyl]-benzoic acid, 4-[bis-(3,5-diisopropyl-phenyl)-methyl]-benzoic acid, 4-[diphenyl-methyl]-nitro-benzene, 4-[bis-(3, 5-dimethyl-phenyl)-methyl]-nitro-benzene, 4-[bis-(3,5-diisopropyl-phenyl)-methyl]-nitro-benzene, 4-[diphenyl-methyl]-benzenamine, 4-[bis-(3,5-dimethyl-phenyl)-methyl]-benzenamine, 4-[bis-(3,5-diisopropyl-phenyl)-methyl]-benzenamine, diphenyl-ether, bis-(3,5-dimethyl-phenyl)-ether, bis-(3,5-diisopropyl-phenyl)-ether, diphenyl-amine, bis-(3,5-dimethyl-phenyl)-amine, bis-(3,5-diisopropyl-phenyl)-amine, diphenyl-phosphine, bis-(3,5-dimethyl-phenyl)-phosphine, bis-(3,5-diisopropyl-phenyl)-phosphine, diphenyl sulfide, bis-(3,5-dimethyl-phenyl)-sulfide, bis-(3,5-diisopropyl-phenyl)-sulfide, methyl-diphenyl-borane, methyl-bis-(3,5-dimethyl-phenyl)-borane, methyl-bis-(3,5-diisopropyl-phenyl)-borane, methyl-diphenyl-aluminium, methyl-bis-(3,5-dimethyl-phenyl)-aluminium, methyl-bis-(3,5-diisopropyl-phenyl)-aluminium, dimethyl-diphenyl-silane, dimethyl-bis-(3,5-dimethyl-phenyl)-silane, dimethyl-bis-(3,5-diisopropyl-phenyl)-silane, 2,5-diphenyl-pyrrole, 2,5-bis-(3,5-dimethyl-phenyl)-pyrrole, 2,5-bis-(3,5-diisopropyl-phenyl)-pyrrole, 2,5-diphenyl-furan, 2,5-bis-(3,5-dimethyl-phenyl)-furan, 2,5-bis-(3,5-diisopropyl-phenyl)-furan, 2,6-diphenyl-pyridine, 2,6-bis-(3, 5-dimethyl-phenyl)-pyridine, 2,6-bis-(3,5-diisopropyl-phenyl)-pyridine diphenylferrocene, Bis-(imino)-pyridin-iron-dichloride, Bis-(imino)-pyridin-iron-dibromide, [2,2'; 6',2"]terpyridine-iron-dichloride, [2,2';6',2"]terpyridine-iron-dibromide, Bis-(imino)-pyridin-cobalt-dichloride, Bis-(imino)-pyridin-cobalt-dibromide, [2,2';6',2"]terpyridine-cobalt-dichloride, [2,2';6',2"]terpyridine-cobalt-dibromide, ethane-1,2-diylidenediamine-nickel-dichloride, ethane-1,2-diylidenediamine-nickel-dibromide, ethane-1,2-diylidenediamine-palladium-dichloride, ethane-1,2-diylidenediamine-palladium-dibromide, ethane-1,2-diylidenediamine-copper-dichloride, ethane-1,2-diylidenediamine-copper-dibromide, ethane-1,2-dimethyl-1,2-diylidenediamine-nickel-dichloride, ethane-1,2-dimethyl-1,2-diylidenediamine-nickel-dibromide, ethane-1,2-dimethyl-1,2-diylidenediamine-palladium-dichloride, ethane-1,2-dimethyl-1,2-diylidenediamine-palladium-dibromide, ethane-1,2-dimethyl-1,2-diylidenediamine-copper-dichloride, and ethane-1,2-dimethyl-1,2-diylidenediamine-copper-dibromide.

\* \* \* \* \*